US010896756B2

(12) United States Patent
Cook et al.

(10) Patent No.: US 10,896,756 B2
(45) Date of Patent: Jan. 19, 2021

(54) ENVIRONMENTAL SENSOR-BASED COGNITIVE ASSESSMENT

(71) Applicants: Diane J. Cook, Pullman, WA (US); Maureen E. Edgecombe, Pullman, WA (US); Prafulla N. Dawadi, Foster City, CA (US)

(72) Inventors: Diane J. Cook, Pullman, WA (US); Maureen E. Edgecombe, Pullman, WA (US); Prafulla N. Dawadi, Foster City, CA (US)

(73) Assignee: Washington State University, Pullman, WA (US)

( * ) Notice: Subject to any disclaimer, the term of this patent is extended or adjusted under 35 U.S.C. 154(b) by 1134 days.

(21) Appl. No.: 15/135,390

(22) Filed: Apr. 21, 2016

(65) Prior Publication Data

US 2016/0314255 A1 Oct. 27, 2016

Related U.S. Application Data

(60) Provisional application No. 62/150,794, filed on Apr. 21, 2015.

(51) Int. Cl.
G06F 16/25 (2019.01)
G06F 16/906 (2019.01)
(Continued)

(52) U.S. Cl.
CPC .......... *G16H 50/20* (2018.01); *G06F 16/254* (2019.01); *G06F 16/906* (2019.01); *G06F 19/00* (2013.01);
(Continued)

(58) Field of Classification Search
CPC ........ G06F 19/00; G06N 20/00; G06N 20/10; G06N 20/20; G16H 50/20
See application file for complete search history.

(56) References Cited

U.S. PATENT DOCUMENTS

| 2005/0113703 A1* | 5/2005 | Farringdon | .......... | A61B 5/0428 600/509 |
| 2013/0238538 A1* | 9/2013 | Cook | ..................... | G05B 15/02 706/20 |

OTHER PUBLICATIONS

Schmitter-Edgecombe, M. et al., "Assessment of Functional Change and Cognitive Correlates in the Progression from Healthy Cognitive Aging to Dementia," Neuropsychology, vol. 28, No. 6, pp. 881-893, Nov. 2014, retrieved at https://www.ncbi.nlm.nih.gov/pubmed/24933485.

(Continued)

*Primary Examiner* — Taelor Kim
(74) *Attorney, Agent, or Firm* — Ellen M. Bierman; Lowe Graham Jones PLLC

(57) ABSTRACT

Methods, systems, and techniques for facilitating cognitive assessment are provided. Example embodiments provide a Cognitive Assessment Facilitator System CAFS, which facilitates the gathering and prediction of cognitive assessment of individuals using machine learning and sensors placed in the home of a resident. These predictive assessments can then be used by a clinician to further diagnose and/or provide health intervention. In one embodiment, the CAFS comprises a sensor input module, a machine learning engine (or algorithm as part of another component), a CAAB tool, and activity curve change engine (activity tools), and a reporting module 308. These components cooperate to process and transform smart home based sensor data into activity performance features and statistical activity features which are then processing through a machine learning engine to predict clinical cognitive assessment values.

19 Claims, 21 Drawing Sheets
(12 of 21 Drawing Sheet(s) Filed in Color)

(51) Int. Cl.
G16H 50/20 (2018.01)
G06N 20/00 (2019.01)
G06F 19/00 (2018.01)
G06N 20/10 (2019.01)
G06N 20/20 (2019.01)

(52) U.S. Cl.
CPC .............. *G06N 20/00* (2019.01); *G06N 20/10* (2019.01); *G06N 20/20* (2019.01)

(56) References Cited

OTHER PUBLICATIONS

Schmitter-Edgecombe, M. et al., "Cognitive Correlates of Functional Performance in Older Adults: Comparison of Self-Report, Direct Observation, and Performance-Based Measures," J. of the International Neuropsychological Society JINS, vol. 17, No. 5, pp. 853-864, 2011, retrieved at https://eecs.wsu.edu/~cook/pubs/jins11.pdf.
Schmitter-Edgecombe, M. et al., "Development and Psychometric Properties of the Instrumental Activities of Daily Living: Compensation Scale," Archives of Clinical Neuropsychology, J. of the National Academy of Neuropsychologists, vol. 29, No. 8, pp. 776-792, Dec. 2014, retrieved at https://www.ncbi.nlm.nih.gov/pubmed/25344901.
Schmutte, T. et al., "The Relation Between Cognitive Functioning and Self-Reported Sleep Complaints in Nondemented Older Adults: Results From the Bronx Aging Study," Behav. Sleep Med. 5 (1) (2007) 39-56, retrieved at https://www.ncbi.nlm.nih.gov/pubmed/17313323.
Sriperumbudur, B et al., "The effect of kernel choice of RKHS based statistical tests," in: Representations and Inference on Probability Distributions Workshop, NIPS, Vancouver, B.C, Canada, 2007.
Sugiyama, M. et al., "Least-Squares Two-Sample Test," Neural Networks, 24 (7) (2011) 735-751.
Sun, F. et al., "Nonparametric Discovery of Human Routines from Sensor Data," in: 2014 IEEE International Conference on Pervasive Computing and Communications, PerCom, IEEE, 2014, pp. 11-19.
Suzuki, T. et al., "Influence of Outdoor Activity and Indoor Activity on Cognition Decline: Use of an Infrared Sensor to Measure Activity," Telemedicine journal and e-health, journal of the American Telemedicine Association, vol. 16, No. 6, pp. 686-690, 2010, retrieved at https://www.ncbi.nlm.nih.gov/pubmed/20575611.
Wang, S. et al., "Activity Density Map Visualization and Dissimilarity Comparison for Eldercare Monitoring," IEEE Transactions on Information Technology in Biomedicine, vol. 16, No. 4, pp. 607-614, Jul. 2012, retrieved at https://www.ncbi.nlm.nih.gov/pubmed/22547460.
Zheng, J. et al., "Effective Routine Behavior Pattern Discovery from Sparse Mobile Phone Data via Collaborative Filtering," in: 2013 IEEE International Conference on Pervasive Computing and Communications, PerCom, IEEE, 2013, pp. 29-37.
Albert, M. et al., "The diagnosis of mild cognitive impairment due to Alzheimer's disease: Recommendations from the National Institute on Aging-Alzheimer's Association workgroups on diagnostic guidelines for Alzheimer's disease," Alzheimer's & dementia, the journal of the Alzheimer's Association, vol. 7, No. 3, pp. 270-279, May 2011, retrieved at https://www.ncbi.nlm.nih.gov/pubmed/21514249.
Artero, S. et al., "Disability and mild cognitive impairment: A longitudinal population-based study," Int. J. Geriatr. Psychiatry 16 (11) (2001) 1092-1097.
Benjamini, Y. et al., "Controlling the False Discovery Rate: A Practical and Powerful Approach to Multiple Testing," J. R. Stat. Soc. Ser. B Stat. Methodol. 57 (1) (1995) 289-300.
Chaytor, N. et al., "Improving the ecological validity of executive functioning assessment," Archives of Clinical Neuropsychology, vol. 21, No. 3, pp. 217-227, Apr. 2006, retrieved at https://www.ncbi.nlm.nih.gov/pubmed/16554143.

Chen, C. et al., "CASASviz: Web-based Visualization of Behavior Patterns in Smart Environments," in 2011 IEEE International Conference on Pervasive Computing and Communications Workshops (PERCOM Workshops), IEEE, Mar. 2011, pp. 301-303, retrieved at http://eecs.wsu.edu/~cook/pubs/percom11p2.pdf.
Cook, D. et al., "Activity Discovery and Activity Recognition: A New Partnership," IEEE Trans. Syst. Man Cybern. B 43 (3) (2013) 820-828, retrieved at https://eecs.wsu.edu/~cook/pubs/smc12.pdf.
Cook, D. et al., "CASAS: A Smart Home in a Box," Computer, vol. 46, No. 7, pp. 62-69, Jul. 2013, retrieved at https://eecs.wsu.edu/~cook/pubs/computer12.pdf. Dakos, V. et al., Methods for Detecting Early Warnings of Critical Transitions.
Dakos, V. et al., "Methods for Detecting Early Warnings of Critical Transitions in Time Series Illustrated Using Simulated Ecological Data," PLoS ONE, vol. 7, No. 7, p. e41010, Jan. 2012, retrieved at http://journals.plos.org/plosone/article?id=10.1371/journal.pone.0041010.
Dawadi, P. et al., "Automated Assessment of Cognitive Health Using Smart Home Technologies," Technol. Health Care 21 (4) (2013) 323-343, retrieved at https://eecs.wsu.edu/~cook/pubs/thc13.pdf.
Dawadi, P. et al., "Automated Cognitive Health Assessment Using Smart Home Monitoring of Complex Tasks," IEEE Transactions on Systems, Man, and Cybernetics: Systems, vol. 43, No. 6, pp. 1302-1313, 2013, retrieved at https://eecs.wsu.edu/~cook/pubs/thms12.pdf.
Deschenes, C. et al., "Current Treatments for Sleep Disturbances in Individuals With Dementia," Curr Psychiatry Rep., vol. 11, No. 1, pp. 20-26, Feb. 2009, retrieved at https://www.ncbi.nlm.nih.gov/pmc/articles/PMC2649672/.
Dodge, H. et al., "In-home walking speeds and variability trajectories associated with mild cognitive impairment," Neurology, vol. 78, No. 24, pp. 1946-1952, Jun. 2012, retrieved at https://www.ncbi.nlm.nih.gov/pubmed/22689734.
Driscoll, H. et al., "Sleeping Well, Aging Well: A Descriptive and Cross-Sectional Study of Sleep in 'Successful agers' 75 and Older," Am. J. Geriatr. Psychiatry 16 (1) (2008) 74-82.
Eeles, E., "Sleep and its management in dementia," Rev. Clin. Geront. 16 (01) (2007) 59-70.
Farias, S. et al., "MCI is Associated With Deficits in Everyday Functioning," Alzheimer Dis Assoc Disord., vol. 20, No. 4, pp. 217-223, 2006, retrieved at https://www.ncbi.nlm.nih.gov/pubmed/17132965.
Farrahi, K. et al., "Discovering Routines from Large-Scale Human Locations using Probabilistic Topic Models," ACM Trans. Intell. Syst. Technol. 2 (1) (2011) 1-27, retrieved at http://www.idiap.ch/~gatica/publications/FarrahiGatica-tist11.pdf.
Farrahi, K. et al., "What Did You Do Today? Discovering Daily Routines from Large-Scale Mobile Data," in: Proceeding of the 16th ACM International Conference on Multimedia, MM '08, ACM Press, New York, New York, USA, 2008, pp. 849-852, retrieved at http://www.idiap.ch/~gatica/publications/FarrahiGatica-mm08.pdf.
Galambos, C. et al., "Management of Dementia and Depression Utilizing In-Home Passive Sensor Data," Gerontechnology, vol. 11, No. 3, pp. 457-468, 2013, retrieved at https://www.ncbi.nlm.nih.gov/pubmed/24049513.
Gretton, A. et al., "A Kernel Two-Sample Test," J. Mach. Learn. Res. 13 (1) (2012) 723-773.
Gross, A. et al., "Cognitive Predictors of Everyday Functioning in Older Adults: Results From the ACTIVE Cognitive Intervention Trial," J. Gerontol. B Psychol. Sci. Soc. Sci. 66 (5) (2011) 557-566, retrieved at https://www.ncbi.nlm.nih.gov/pubmed/21558167.
Hayes, T. et al., "Unobtrusive assessment of activity patterns associated with mild cognitive impairment," Alzheimer's Dement. 4 (6) (2008) 395-405, retrieved at https://www.ncbi.nlm.nih.gov/pubmed/19012864.
Hodges, M. et al., "Automatic Assessment of Cognitive Impairment Through Electronic Observation of Object Usage," in: P. Floréen, A. Krüger, M. Spasojevic (Eds.), Proc. International Conference on Pervasive Computing, in: Lecture Notes in Computer Science, vol. 6030, Springer Berlin Heidelberg, Berlin, Heidelberg, 2010, pp. 192-209, retrieved at http://www.mwnewman.people.si.umich.edu/pubs/pervasive10-hodges.pdf.

(56) References Cited

OTHER PUBLICATIONS

Hope, T. et al., "Predictors of Institutionalization for People with Dementia Living at Home with a Carer," Int. J. Geriat. Psychiatry, vol. 13, No. 10, pp. 682-690, Oct. 1998, retrieved at https://www.ncbi.nlm.nih.gov/pubmed/9818303.
Hotelling, H., "The Generalization of Student's Ratio," The Annals of Mathematical Statistics, vol. 2, No. 3, pp. 360-378, Aug. 1931.
Huynh, T. et al., "Discovery of Activity Patterns using Topic Models," in: Proceedings of the 10th International Conference on Ubiquitous Computing, UbiComp '08, ACM Press, New York, New York, USA, 2008, pp. 10-19, retrieved at http://citeseerx.ist.psu.edu/viewdoc/download?doi=10.1.1.232.1932&rep=rep1&type=pdf.
Jelicic, M. et al., "Subjective sleep problems in later life as predictors of cognitive decline. Report from the Maastricht Ageing Study (MAAS)," Int J Geriatr Psychiatry, vol. 17, No. 1, pp. 73-77, Jan. 2002, retrieved at https://www.ncbi.nlm.nih.gov/pubmed/11802234.
Kanis, M. et al., "Sensor Monitoring in the Home: Giving Voice to Elderly People," in Pervasive Computing Technologies for Healthcare (PervasiveHealth), 2013 7th International Conference on, Venice, Italy, 2013, pp. 97-100.
Kanis, M. et al., Sensor Monitoring in the Home: Giving Voice to Elderly People,: in: 2013 7th International Conference on Pervasive Computing Technologies for Healthcare, PervasiveHealth, Venice, Italy, 2013, pp. 97-100.
Krishnan, N. et al., "Activity Recognition on Streaming Sensor Data," Pervasive and mobile computing, vol. 10, pp. 138-154, Feb. 2014, retrieved at https://eecs.wsu.edu/~cook/pubs/pmc12b.pdf.
LeBellego, G. et al., "A Model for the Measurement of Patient Activity in a Hospital Suite," IEEE Transactions on Information Technology in Biomedicine, vol. 10, No. 1, pp. 92-99, Jan. 2006.
Luck, T. et al., Impact of impairment in instrumental activities of daily living and mild cognitive impairment on time to incident dementia: results of the Leipzig Longitudinal Study of the Aged, Psychol. Med. 41 (5) (2011) 1087-1097, retrieved at https://www.ncbi.nlm.nih.gov/pubmed/20667169.
Martin, J. et al., "Sleep Quality in Residents of Assisted Living Facilities: Effect on Quality of Life, Functional Status, and Depression," J Am Geriatr Soc., vol. 58, No. 5, pp. 829-836, May 2010, retrieved at https://www.ncbi.nlm.nih.gov/pubmed/20722819.
McAlister, C. et al., "Naturalistic Assessment of Executive Function and Everyday Multitasking in Healthy Older Adults," Neuropsychology, development, and cognition. Section B, Aging, neuropsychology and cognition, vol. 20, No. 6, pp. 735-756, Jan. 2013, retrieved at https://www.ncbi.nlm.nih.gov/pubmed/23557096.
Noury, N. et al., "Building an Index of Activity of Inhabitants From Their Activity on the Residential Electrical Power Line," IEEE transactions on information technology in biomedicine, a publication of the IEEE Engineering in Medicine and Biology Society, vol. 15, No. 5, pp. 758-766, Sep. 2011, retrieved at https://www.ncbi.nlm.nih.gov/pubmed/21896382.
Ohayon, M. et al., "Meta-Analysis of Quantitative Sleep Parameters From Childhood to Old Age in Healthy Individuals: Developing Normative Sleep Values Across the Human Lifespan," Sleep, vol. 27, No. 7, pp. 1255-1273, Nov. 2004, retrieved at https://www.ncbi.nlm.nih.gov/pubmed/15586779.
Ojala, M. et al., "Permutation Tests for Studying Classifier Performance," J. of Machine Learning Research, vol. 11, pp. 1833-1863, Mar. 2010.
Ouchi, Y. et al., "Impaired instrumental activities of daily living affect conversion from mild cognitive impairment to dementia: the Osaki-Tajiri Project," Psychogeriatrics, vol. 12, No. 1, pp. 34-42, Mar. 2012, retrieved at https://www.ncbi.nlm.nih.gov/pubmed/22416827.
Paavilainen, P. et al., "Circadian activity rhythm in demented and non-demented nursing-home residents measured by telemetric actigraphy," J. Sleep Res., vol. 14, No. 1, pp. 61-68, Mar. 2005, retrieved at https://www.ncbi.nlm.nih.gov/pubmed/15743335.
Paavilainen, P. et al., "Telemetric activity monitoring as an indicator of long-term changes in health and well-being of older people," Gerontechnology, vol. 4, No. 2, pp. 77-85, 2005.
Pedrosa, H. et al., "Functional Evaluation Distinguishes MCI Patients From Healthy Elderly People—The ADCS/MCI/ADL Scale," J. Nutr. Health Aging 14 (8) (2010) 703-709, retrieved at https://www.ncbi.nlm.nih.gov/pubmed/20922349.
Pérès, K. et al., "Restriction in complex activities of daily living in MCI, Impact on outcome," Neurology, vol. 67, No. 3, pp. 461-466, Aug. 2006, retrieved at https://www.ncbi.nlm.nih.gov/pubmed/16894108.
Podsiadlo, D. et al., "The Timed "Up & Go": A Test of Basic Functional Mobility for Frail Elderly Persons." JAGS, vol. 39, No. 2, pp. 142-148,1991, retrieved at https://www.ncbi.nlm.nih.gov/pubmed/1991946.
Rashidi, P. et al., "Keeping the Resident in the Loop: Adapting the Smart Home to the User," IEEE Trans. Syst. Man Cybern. A 39 (5) (2009) 949-959, retrieved at https://eecs.wsu.edu/~cook/pubs/smca09.pdf.
Rashidi, P. et al., "Mining Sensor Streams for Discovering Human Activity Patterns Over Time," in: 2010 IEEE International Conference on Data Mining, IEEE, 2010, pp. 431-440, retrieved at https://eecs.wsu.edu/~cook/pubs/icdm10.pdf.
Riboni, D. et al., "Fine-grained Recognition of Abnormal Behaviors for Early Detection of Mild Cognitive Impairment," Proc. PerCom (2015) 149-154.
Robben, S. et al., "How is Grandma Doing? Predicting Functional Health Status from Binary Ambient Sensor Data," in: 2012 AAAI Fall Symposium Series, Washington D.C, 2012, pp. 26-31, retrieved at https://www.aaai.org/ocs/index.php/FSS/FSS12/paper/view/5605.
Robben, S. et al., "Identifying and Visualizing Relevant Deviations in Longitudinal Sensor Patterns for Care Professionals," in: 7th International Conference on Pervasive Computing Technologies for Healthcare, PervasiveHealth, Venice, Italy, 2013, pp. 416-419.
Robben, S. et al., "Longitudinal Ambient Sensor Monitoring for Functional Health Assessments: A Case Study," in Proceedings of the 2014 ACM International Joint Conference on Pervasive and Ubiquitous Computing Adjunct Publication—UbiComp '14 Adjunct, New York, New York, USA, ACM Press, Sep. 2014, pp. 1209-1216.
Scherder, E. et al., "Gait in ageing and associated dementias; its relationship with cognition," Neuroscience and Biobehavioral Reviews, vol. 31, No. 4, pp. 485-497, Jan. 2007, retrieved at https://www.ncbi.nlm.nih.gov/pubmed/17306372.
Schmitter-Edgecombe, M. et al, "Naturalistic Assessment of Everyday Functioning in Individuals with Mild Cognitive Impairment: The Day-Out Task," Neuropsychology 26 (5) (2012) 631-641, retrieved at https://www.ncbi.nlm.nih.gov/pubmed/22846035.
Stopping elderly accidents, deaths & injuries, Center for Disease Control and Prevention, 2017, page available online at https://www.cdc.gov/steadi/pdf/TUG_Test-print.pdf.

* cited by examiner

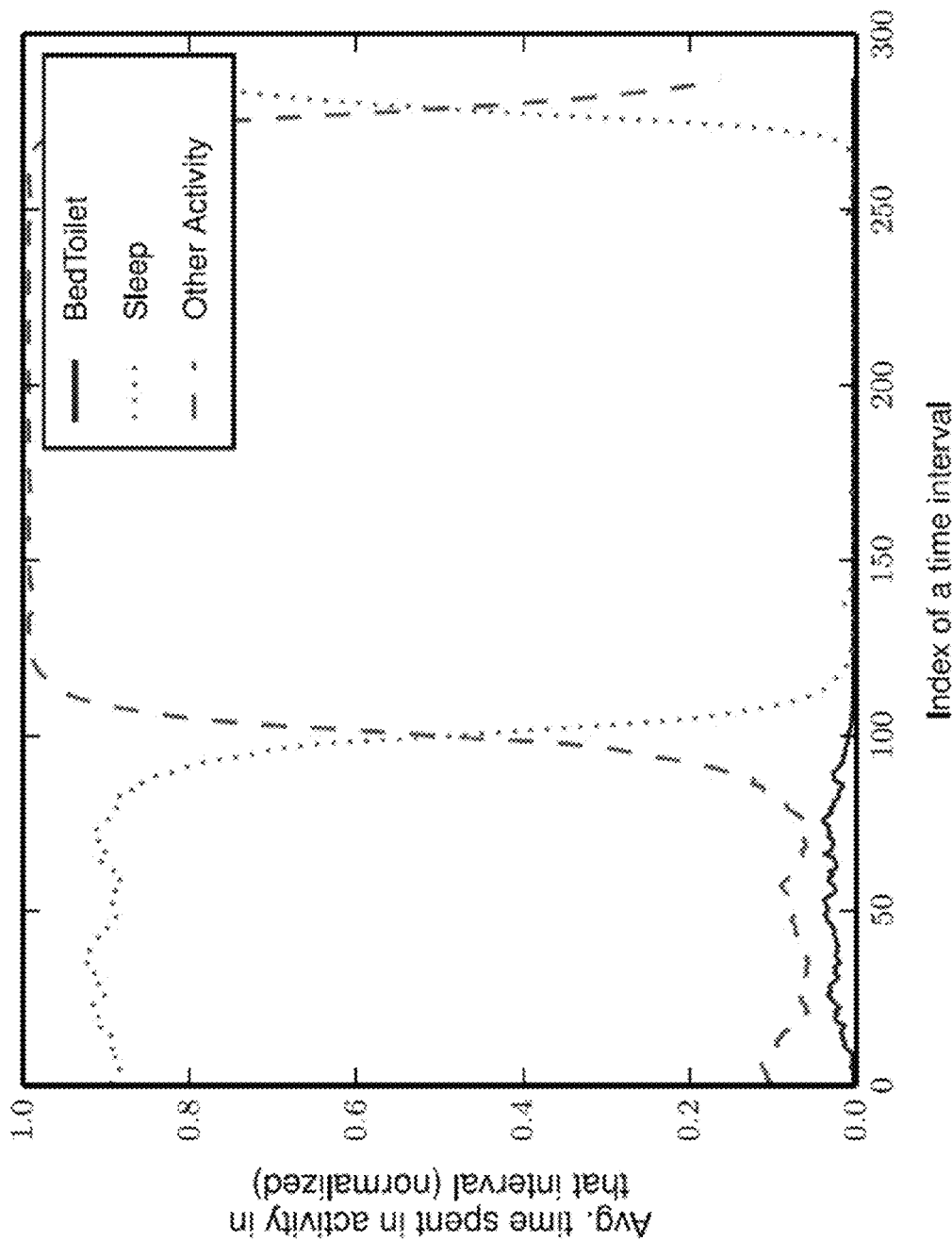

Fig. 6

An example aggregated activity curve that models three different activities: sleep, bed toilet transition, and an "other" activity. This sample aggregated activity curve was derived using x = three months of actual smart home data. Aggregated activity distributions were calculated at 5 min time intervals. (m = 288). In this graph, the time interval at index 0 represents 12:00 AM.

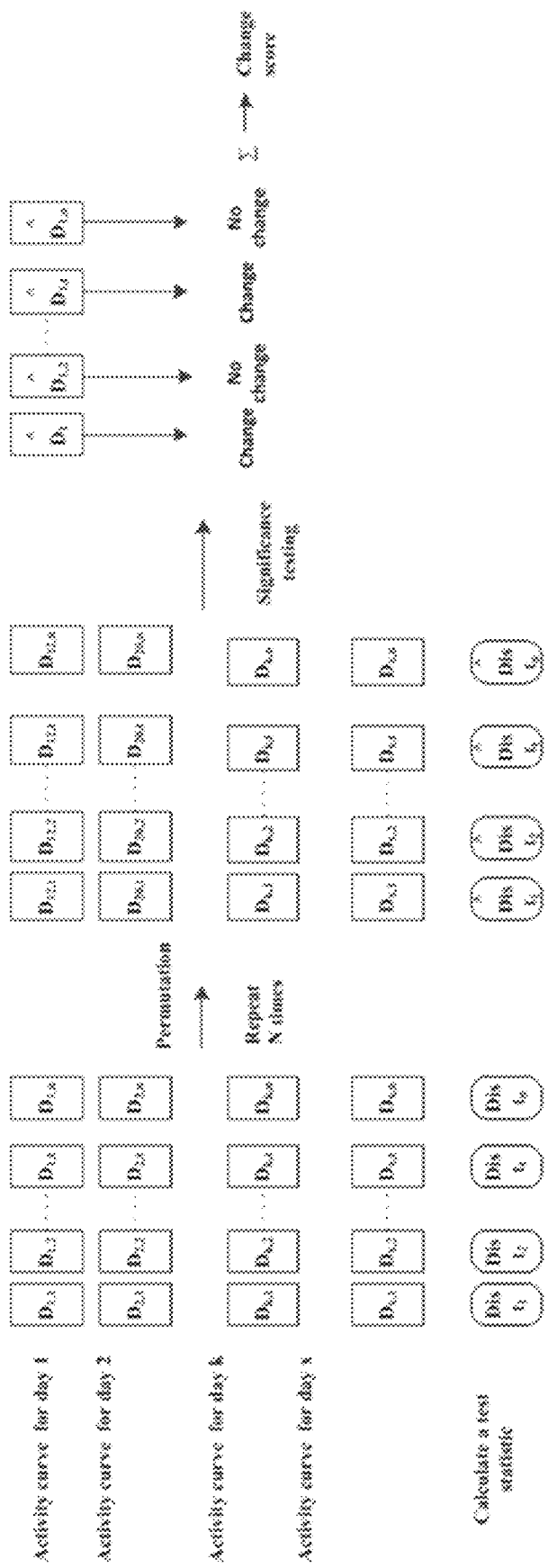

The permutation-based steps to detect changes in the activity curve. The first step is to compute the test statistic from the original samples. In the second step, the samples are rearranged N times and the test statistic is calculated for each arrangement. In the third step, significance testing is performed by comparing the test statistic obtained from the original (unpermuted) set of data with the test statistic obtained from the permuted data. Finally, a change score is calculated by counting the number of significant changes in activity distributions.

Fig. 7

Distribution of RBANS (left) and TUG (right) clinical assessment scores in the y-axis with respect to age in x-axis. The horizontal line represents a mean clinical score and the vertical line represents the mean age.

The correlation coefficients (top) and RMSE (bottom) between predicted and actual RBANS (left) and TUG (right) scores when different trend removal techniques and window sizes are used to train a SVR Correlation coefficients (top) and RMSE (bottom) between SVR predicted and actual RBANS (left) and TUG (right) scores when the SVR was trained using features derived from randomly-labeled and AR-labeled activities. The complete set of statistical features was used to train the SVR.

Classification performance (AUC and G-Mean) of the SVM with boosting in classifying the discretized RBANS (left) and TUG (right) scores. The RBANS score was discretized into two classes at different thresholds and trained the SVM using the complete feature set.

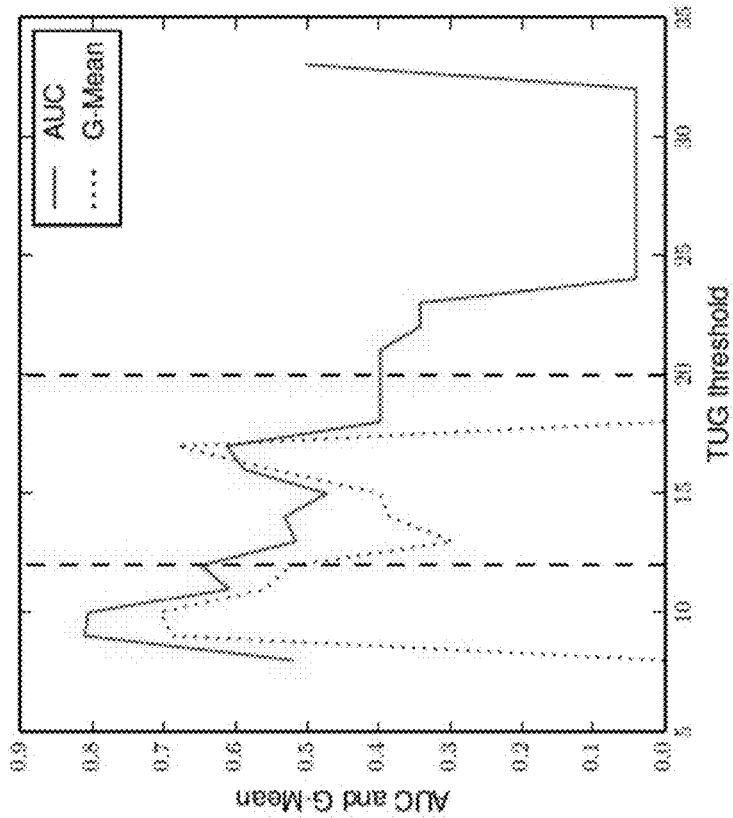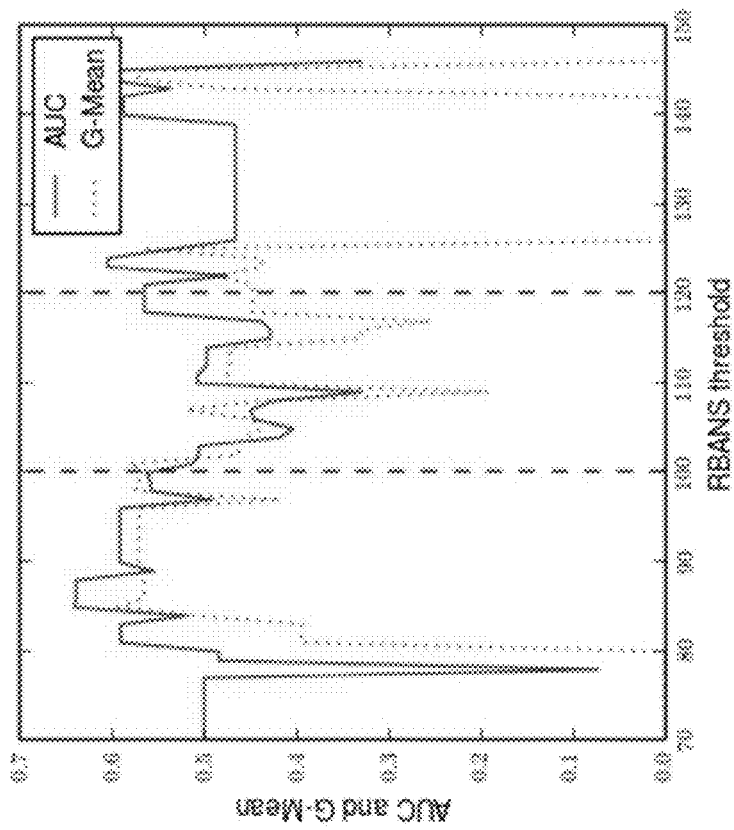
Fig. 13
Classification performance (AUC and G-Mean) of the SVM while classifying RBANS (left) and TUG (right) clinical scores when the SVM is trained using features that are derived from randomly-annotated activities. The complete feature set was used to train the SVMs and discretize the clinical assessment scores into two classes.

An example of aggregated activity curve that models eight different activities. This sample aggregated activity curve was derived using x = three months of actual smart home data. Aggregated activity distributions were calculated at 5 min time intervals. (m = 288).

Heat map of the pairwise distance matrix between activity distributions of an aggregated activity curve using KL distance. The size of the time interval is 5 min. Index 0 represents 12:00 AM.

Average intra-curve pairwise KL distance as a function of time interval size

Pearson (r) and Spearman rank (rho) correlations between activity change scores and RBANS scores.

| Interval size | Time interval change score | | DTW score | | Random scores | |
|---|---|---|---|---|---|---|
| | r-RBANS | rho-RBANS | r-RBANS | rho-RBANS | r-RBANS | rho-RBANS |
| 5 | 0.00 | −0.10 | 0.11 | −0.04 | 0.10 | 0.06 |
| 6 | −0.01 | −0.13 | 0.06 | −0.10 | 0.14 | 0.14 |
| 8 | −0.01 | −0.16 | 0.04 | −0.08 | −0.06 | 0.00 |
| 9 | −0.03 | −0.19 | 0.03 | −0.09 | 0.09 | 0.11 |
| 10 | −0.03 | −0.15 | −0.03 | −0.13 | −0.07 | −0.10 |
| 12 | −0.04 | −0.17 | −0.03 | −0.13 | −0.07 | −0.07 |
| 15 | −0.04 | −0.14 | −0.05 | −0.16 | 0.11 | 0.26 |
| 16 | −0.04 | −0.13 | −0.04 | −0.14 | −0.19 | −0.19 |
| 18 | −0.06 | −0.18 | −0.08 | −0.22 | −0.02 | 0.04 |
| 20 | −0.04 | −0.18 | −0.03 | −0.16 | −0.16 | −0.13 |
| 24 | −0.04 | −0.20 | −0.03 | −0.17 | −0.05 | −0.04 |
| 30 | −0.07 | −0.20 | −0.01 | −0.19 | −0.06 | −0.11 |
| 32 | −0.04 | | 0.01 | | 0.20 | 0.19 |
| 36 | −0.04 | −0.21 | 0.01 | −0.17 | 0.06 | 0.01 |

*Fig. 18A*

Pearson (r) and Spearman rank (rho) correlations between activity change scores and TUG scores.

| Interval size | Time interval change score | | DTW score | | Random scores | |
|---|---|---|---|---|---|---|
| | r-TUG | rho-TUG | r-TUG | rho-TUG | r-TUG | rho-TUG |
| 5 | 0.27* | 0.28* | 0.27* | 0.43† | −0.21 | −0.06 |
| 6 | 0.28* | 0.31* | 0.27* | 0.40† | −0.09 | −0.03 |
| 8 | 0.32* | 0.39† | 0.33* | 0.37† | −0.09 | −0.12 |
| 9 | 0.31* | 0.35* | 0.24 | 0.25 | −0.15 | −0.06 |
| 10 | 0.33* | 0.31* | 0.29* | 0.37† | 0.10 | 0.12 |
| 12 | 0.35† | 0.33* | 0.30* | 0.30* | 0.18 | 0.15 |
| 15 | 0.33* | 0.34* | 0.31* | 0.40† | 0.06 | −0.06 |
| 16 | 0.34* | 0.38† | 0.30* | 0.35* | −0.03 | −0.10 |
| 18 | 0.32* | 0.29* | 0.29* | 0.27* | −0.17 | −0.07 |
| 20 | 0.32* | 0.35* | 0.31* | 0.28* | 0.19 | 0.12 |
| 24 | 0.35* | 0.29* | 0.28* | 0.23 | −0.10 | −0.13 |
| 30 | 0.33* | 0.24 | 0.28* | 0.27* | −0.15 | −0.15 |
| 32 | 0.33* | 0.28* | 0.28* | 0.32* | −0.15 | −0.13 |
| 36 | 0.32* | 0.28* | 0.28* | 0.31* | 0.01 | 0.03 |

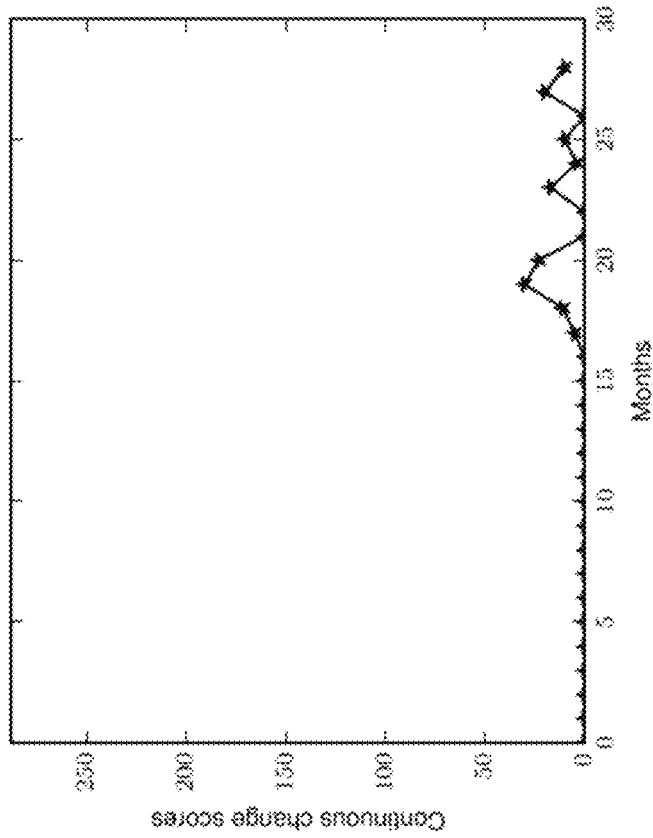
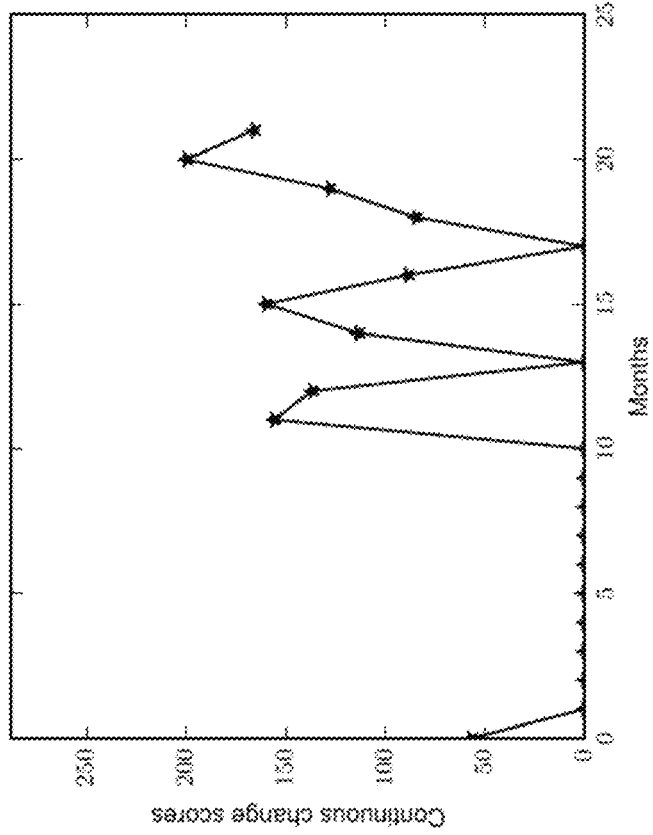
Fig. 19
The continuous change scores of two residents calculated by running PCAR algorithm on a sliding window of 6 months with an aggregation window size of 30 days

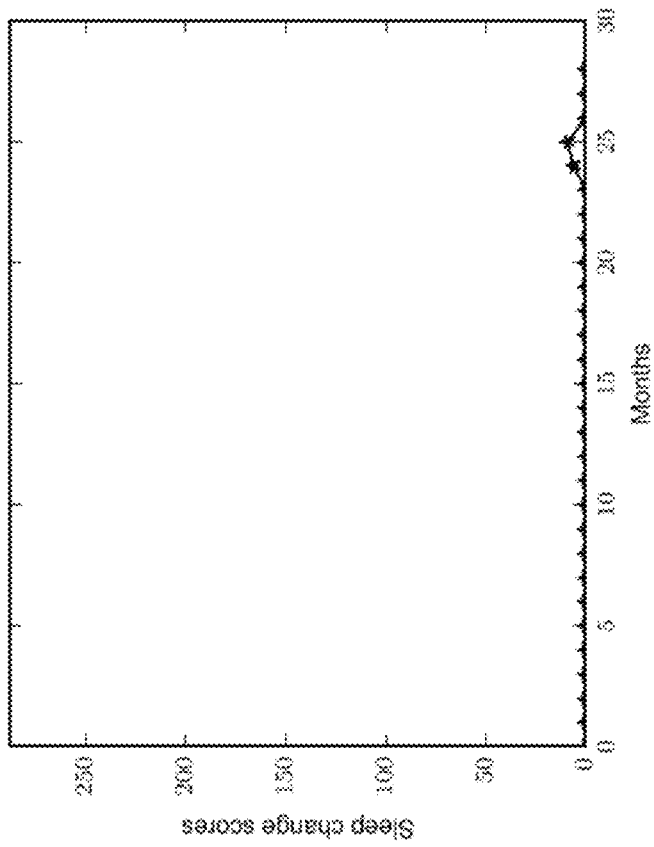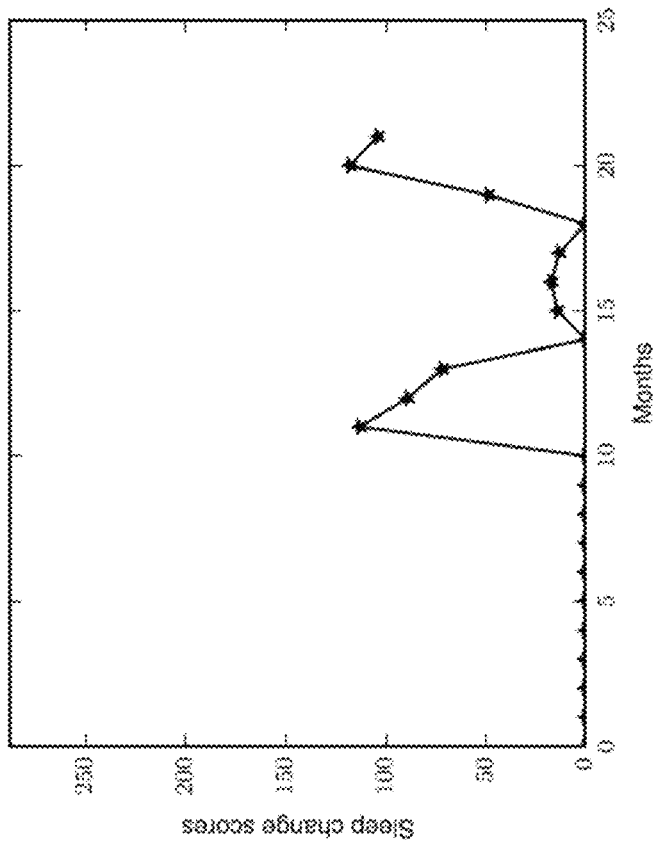
Fig. 20
The continuous sleep change scores of two residents calculated by running PCAR algorithm on a sliding window of 6 months with an aggregation window size of x = 30 days.

ENVIRONMENTAL SENSOR-BASED COGNITIVE ASSESSMENT

CROSS-REFERENCE TO RELATED APPLICATIONS

This application claims the benefit of U.S. Patent Application No. 62/150,794, entitled "MODELING PATTERNS OF ACTIVITIES USING ACTIVITY CURVES," filed Apr. 21, 2015, which is incorporated herein by reference in its entirety.

STATEMENT REGARDING FEDERALLY SPONSORED RESEARCH OR DEVELOPMENT

This work was supported in part by grants from the National Institutes of Health (R01EB015853 and R01EB009675) and by a grant from the National Science Foundation (1064628).

TECHNICAL FIELD

The present disclosure relates to methods, techniques, and systems for using environmental sensor-based data to provide insights into cognitive assessment and, in particular, to methods, techniques, and systems for using sensor-based data to determine and model activities of daily living, to predict cognitive assessment, and/or to detect change in functional cognitive abilities over time.

BACKGROUND

A decrease in cognitive and/or physical health may severely impact an individual's ability to function independently. Several clinical studies support a relationship between daily behavior and cognitive and physical health [1]. Everyday activities like cooking and eating are essential Activities of Daily Living (ADLs) that are required to maintain independence and quality of life. For example, some everyday behavior parameters affected by cognitive health include areas such as computer usage (keyboard and mouse usage, typing speed, computer game performance), mobility (ability to move around, climb stairs, stride length), gait (gait velocity, balance), and everyday activities (ability to initiate and complete ADL such as bathing, toileting, eating, etc.). Decline in the ability to independently perform ADLs has been associated with placement in long-term care facilities, shorter time to conversion to dementia, and a lower quality of life for both the functionally-impaired individuals and their caregivers [2].

The relationship between in-home sensor-based measurements of everyday abilities and corresponding clinical measurements has been explored using statistical tools and visualization techniques. Researchers have correlated sensor measurements of sleep patterns, gait, and mobility with standard clinical measurements and self-report data. In one such work, Paavilainen et al. [4] monitored the circadian rhythm of activities of older adults living in nursing homes using the IST Vivago WristCare system. In this study, they compared the changes in activity rhythms with clinical observations of subject health status. In a separate study, these researchers [5] studied the relationship between changes in the sleep pattern of demented and non-demented individuals over a 10-day period.

Several other researchers have considered the relationship between sensor-based activity performance and clinical health assessment. For example, Robben et al. [6] studied the relationship between different high-level features representing the location and transition patterns of an individual's indoor mobility behavior with the Assessment of Motor and Process Skills (AMPS) scores. Similarly, Suzuki and Murase [7] compared indoor activities and outings with Mini-Mental State Examination (MMSE) scores. Dodge et al. used latent trajectory modeling techniques to explore the relationship between gait parameters and cognition [8]. Similarly, LeBellego et al. [9] investigated the relationship between indicators such as mobility and agitation with patient health status in a hospital setting.

In other work, researchers such as Galambos et al. [10] developed techniques to visualize long-term monitoring of sensor data including activity level and time spent away from home [10], [11]. Similarly, other researchers have developed techniques to visualize activity and behavioral patterns by monitoring them with smart home sensors [12], [13], and by monitoring consumption of electricity usage [14].

In earlier work, we demonstrated a correlation between smart home sensor-based performance measurements of simple and complex ADLs and validated performance measures derived from direct observation of participants completing the ADLs in a smart home laboratory [15].

In addition, researchers have studied the problem of automated discovery and recognition of daily activity routines using the data collected from wearable sensors [39], [40], GPS signals [41] and mobile phones [42] using algorithms such as topic modeling [39] and collaborative filtering [43]. In these approaches, raw sensor data are converted to a bag-of-words representation which contains the histogram of activity label occurrences or histogram of location/proximity information. Data from wearable sensors can be used to discover daily routines such as having lunch and brushing teeth [39]. Similarly, data from mobile phones can be used to recognize routines such as commuting to office and working.

Researchers also have proposed visualization techniques to visualize daily activity patterns. For example, Galambos et al. [44], [45] developed methods to visualize activity level, time spent away from home, deviations in activities of daily living, and behavioral patterns. Similarly, other researchers have developed techniques to visualize deviations in activity routines and behavioral patterns using smart home sensors [46], [47]. These methods provide a tool to understand sensor-monitoring data and to study daily activity routines. However, these approaches rely on manual inspection of the data in order to make any higher-level conclusions regarding daily routines.

The two-sample test discussed below is a widely used statistical analysis tool to compare between two sample populations. Classical two-sample tests such as the t-test are used to compare the means of two populations having the same or different variances. However, the t-test is a parametric test that is limited to comparing between two Gaussian distributions. Other examples of non-parametric classical versions of two-sample tests are the Wald-Wolfowitz runs test, the Anderson-Darling test and the Kolmogorov-Smirnov test [48].

Recently, Maximum Mean Discrepancy (MMD) was proposed as another non-parametric two-sample test technique [49]. MMD compares the means of two distributions in a universal reproducing kernel Hilbert space and has superior performance to several of the classic two-sample tests. However, the superior performance of MMD relies on a valid choice of a kernel and kernel width, and recommendations have been made in the literature for obtaining optimal performance with MMD [50]. Similarly, the Least Squares Sample Test (LSTT) technique has been proposed in the literature to make use of permutation to perform two-sample tests [51]. In the LSTT based two-sample test, divergence is estimated using the density ratio estimation technique and the permutation-based technique is used to test the significance of the estimated divergence. Such permutation-based tests are preferable because they are data-centric approaches that make inferences directly from data.

Also, researchers have developed functional assessment algorithms based on different parameters of everyday abilities. These researchers have studied correlations between everyday abilities and corresponding standard clinical measurements. Researchers have correlated sensor measurements of sleep patterns, gait, activity rhythms, indoor activities and outings, and mobility with standard clinical measurements such as MMSE and self-report data. For example, Paavilainen et al. [54] compared the changes in circadian rhythm of activities of older adults living in nursing homes with clinical observations of the health status of subjects. In other work, Robben et al. [55], [56], [57] studied the relationship between different high-level features representing the location and transition patterns of an individual's indoor mobility behavior, namely the frequency, duration and times being carried out, with the Assessment of Motor and Process Skills (AMPS) scores [58]. Other researchers have studied the relationship between walking speed and the amount of in-home activity among healthy older adults and older adults with Mild Cognitive Impairment (MCI) [59]. These researchers found out that coefficient of variation in the median walking speed was higher in the MCI group as compared with the healthy group. However, none of these works considered parameters reflecting the performance of activities of daily living.

Other researchers have developed functional assessment algorithms based on performance of an individual in a fixed set of activities. They have correlated the performance in these activities with the direct observation of participants completing the ADLs. In one such work, Dawadi et al. [60], [61] proposed learning algorithms to obtain activity performance measures of simple and complex ADLs from sensor data and correlated them with validated performance measures derived from direct observation of participants completing the ADLs. They also studied the relationship between sensor-detected activity performance measures and overall cognitive health. In another work, Hodges et al. [62] correlated sensor events gathered during a coffee-making task with an individual's neuropsychological score. Similarly, in an another research effort by Riboni et al. [63] researchers developed a Fine-grained Abnormal BEhavior Recognition (FABER) algorithm to detect abnormal behavior using a statistical-symbolic technique. These researchers hypothesized that such abnormal activity routines may indicate the onset of early symptoms of cognitive decline.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 6 is an example aggregated activity curve used by activity curve tools in an example Cognitive Assessment Facilitator System.

FIG. 7 demonstrates the steps involved in detecting changes in an activity curve using a permutation-based method

FIG. 13 illustrates variations in performance of learning algorithms when trained with randomly labeled activities.

FIGS. 18A and 18B illustrate the correlations between activity change scores and clinical scores (of TUG and RBANS).

FIG. 19 illustrates different continuous change score for two different residents.

FIG. 20 illustrates different continuous sleep change score for the two different residents shown in FIG. 19.

DETAILED DESCRIPTION

Figure 1:
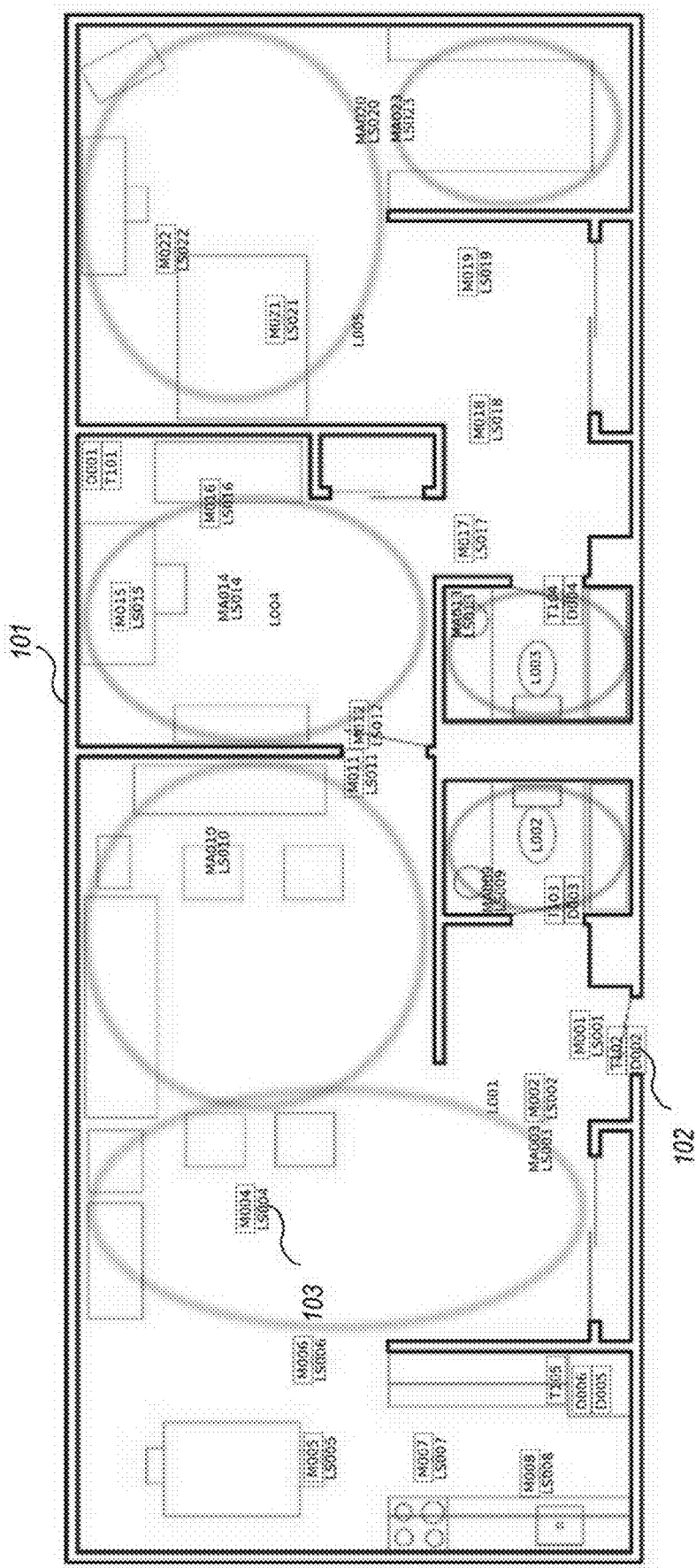
FIG. 1 is an example block diagram of a smart home sensor environment for providing continuous data regarding behavioral activities using an example CAFS.

Smart home technologies offer potential benefits for assisting clinicians by automating health monitoring and wellbeing assessment. The embodiments described herein provide enhanced computer- and network-based methods, techniques, and systems and tools for monitoring Activities of Daily Living (ADLs) using automatically collected (continuous) sensor-based data and, based upon such data, providing technology assisted cognitive assessments of individuals. The sensor-based data can be used to predict cognitive and physical health assessments that correlate to certain standard clinical assessments as well as to measure changes over time in an individual's cognitive health by modeling activity patterns. Using such tools, it is possible to help, for example, the aging population by prompting individuals to perform needed activities such as taking medication on time or to eat, perform home automation, monitor the health of an individual or even to provide preventive measures such as alerts to medical personnel.

Example embodiments provide a computer based Cognitive Assessment Facilitator System ("CAFS") which comprises tools that utilize statistical and machine learning techniques in conjunction with data received in real time from sensors placed in an individual's residence (home, apartment, and the like) to predict cognitive health and changes in a person's activities over time. These sensors are sometimes referred to hereinafter as "smart home sensors." The smart home sensors provide the capability of providing measurements, such as measuring activities in real-time (or near real-time), which can be stored and later analyzed or analyzed in real-time using streaming capabilities designed for capturing large amounts of data. In an example embodiment, the sensors are placed on the ceilings, walls, ingress and egresses such as doorways and windows, and/or associated with appliances, so that identification, duration and location of an activity can be measured. As the ability to provide sensors associated with appliances increases, for example via Internet Of Things (IoT) technologies or the like, the smart home sensors may improve in their capacities to measure activities of daily living beyond those discussed herein.

Example Cognitive Assessment Facilitator Systems provide a Clinical Assessment Using Activity Behavior tool (CAAB) to predict the cognitive and mobility scores of smart home residents by monitoring a set of basic and instrumental activities of daily living. CAAB may be implemented in a networked environment that receives data from the sensors, performs various measurements and uses various tools to quantify and convert the data and predicts cognitive assessments as output. In overview, CAAB first labels the raw data with activity labels and processes the activity-labeled sensor dataset to extract activity performance features. CAAB then extracts statistical activity features from the activity performance features to train machine learning algorithms that can predict the cognitive and mobility scores. Various machine learning algorithms can be incorporated.

Experiments were conducted to evaluate the performance of CAAB and to validate the results using data from 18 real-world smart homes with older adult residents. In the prediction-based experiments, a statistically significant correlation ($r=0:72$) between CAAB predicted and clinician-provided cognitive assessment scores was obtained and a statistically significant correlation ($r=0:45$) between CAAB predicted and clinician-provided mobility scores was obtained. Further, for the classification-based experiments, CAAB showed an accuracy of 72% while classifying cognitive assessment scores and 76% while classifying mobility scores. These prediction and classification results suggest that it is feasible to predict standard clinical scores using smart home sensor data and learning-based data analysis as performed by CAAB. These experiments and their results are presented in Appendix A, incorporated herein by reference in its entirety.

Example Cognitive Assessment Facilitator Systems also provide a set of Activity Curve (AC) tools that facilitate the modeling and analyzing of activity-based behavioral patterns to detect changes to the activity curves of individuals over a period of time. An "activity curve" represents an abstraction of an individual's normal daily routine based on automatically recognized activities. Changes to activity curves can be used to identify and quantify or even predict changes in cognitive and/or physical health so that improved healthcare such as activity aware interventions can be administered. In overview, the Activity Curve tools define and use a set of algorithms to compare activity curves generated using the smart-home sensor data collected as above in conjunction with statistical evaluation and machine learning techniques. Changes to the activity curves are analyzed to identify the possibility of changes to an individual's cognitive or physical health and to provide a functional health assessment. Experiments have been conducted to evaluate the performance of the Activity Curve tools and to validate the results using data from 18 real-world smart homes with older adult residents. These experiments and their results are presented in Appendix B, incorporated herein by reference in its entirety.

Smart Home-Based Sensor Environment

FIG. 1 is an example block diagram of a smart home sensor environment for providing continuous data regarding behavioral activities using an example CAFS. Floor plan 101 shows an example smart home environment as envisioned by the smart home laboratory used to develop and test CAAB. The example residence shown by floor plan 101 is a single resident apartment, with at least one bedroom, a kitchen, a dining area, and at least one bathroom, although many other variations of layout and rooms are contemplated. Here, the terms "residence" or "home" or "smart home" refers to any potential layout that could be enhanced with technology sensors including a single or multi-residence home, apartment, condominium, townhome, or the like. The homes are equipped with combination motion/light sensors throughout the environment, for example on the ceilings e.g., sensor 103, and combination door/temperature sensors on the cabinets and doors, e.g. sensor 102. The location of each sensor is indicated with the corresponding motion (M), light (LS), door (D), or temperature (T) sensor number. For example, sensor D002 T102 corresponds to a door/temperature sensor at location 102. Other types and locations of sensors are contemplated. The sensors are meant to unobtrusively and continuously monitor the daily activities of the residents without awareness or interference by the residents. The residents perform their normal activities in their smart residences, unobstructed by the smart home instrumentation Overview of a Cognitive Assessment Facilitator System (CAFS)

Figure 2:
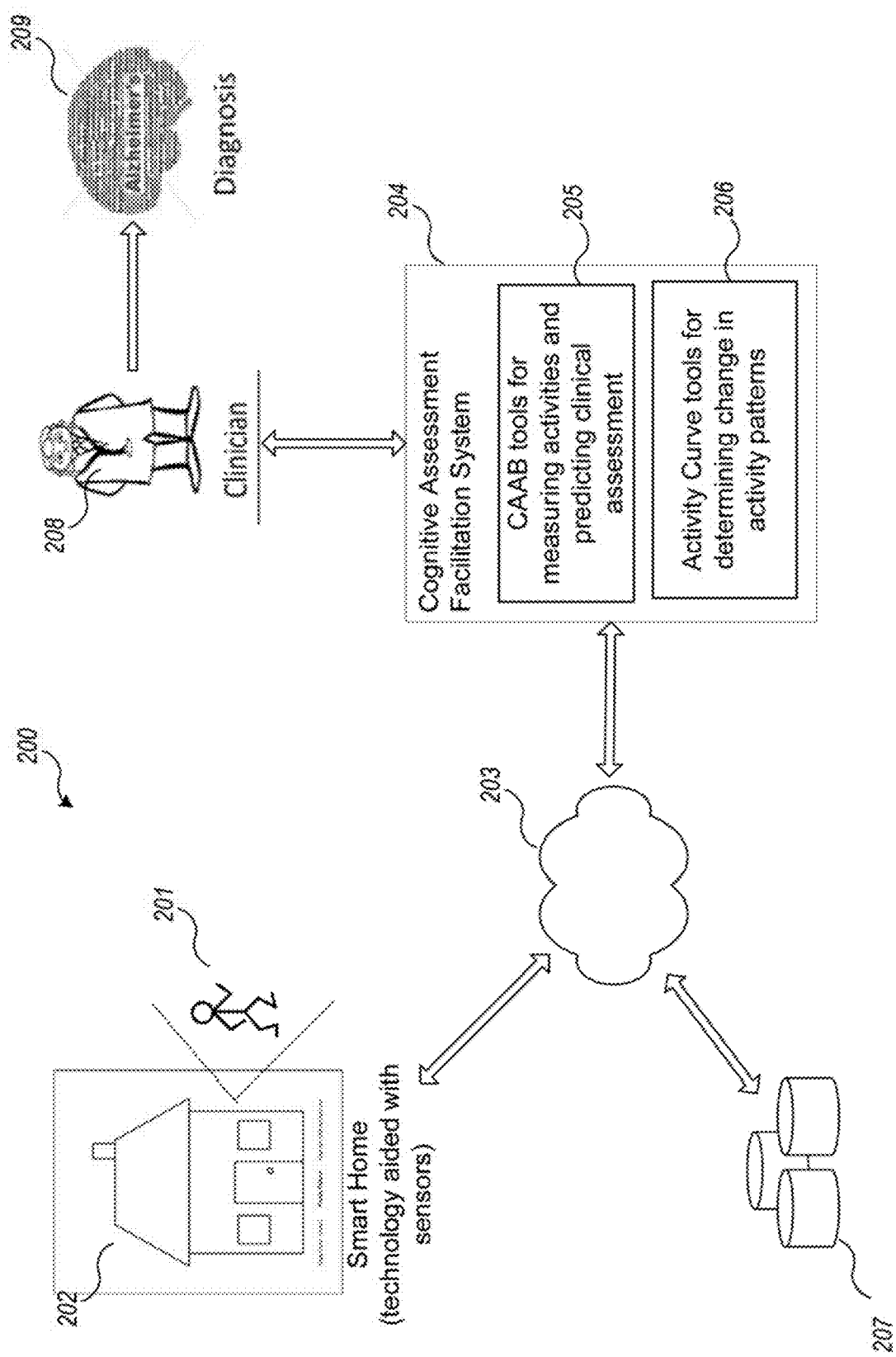
FIG. 2 is an example block diagram of the data flow in the smart home based sensor environment to predict assessment and change using an example Cognitive Assessment Facilitator System.

FIG. 2 is an example block diagram of the data flow in the smart home based sensor environment to predict assessment and change using an example Cognitive Assessment Facilitator System. Technology assisted assessment environment 200 comprises a residences 202 with smart sensor technology for measuring activities such as the Activities of Daily Living of resident 201. The data is collected on a continuous basis and stored somewhere over network 203. In some embodiments it is stored in cloud based server environments, such as cloud storage 207, others it is served on a streaming basis to other computer systems such as server computer system 204 that hosts the CAAB and AC tools. In other environments the data is collected elsewhere (e.g., onto another computer system or network storage device and pulled as needed by computer system 204). Other architectures for getting the data to computer system 204 are similarly incorporated. Once delivered, the raw sensor data is processed by the CAAB tools 205 on computer system 204 to be annotated by CAAB with activity labels. Thereafter, the CAAB tools 205 employ machine learning tools to predict clinical assessments which can be then forward to a human clinician 208 for further health purposes such as preemptive intervention, consultation with the resident, further interpretation or diagnosis 209, and the like. In some deployments, Activity Curve tools 206 are employed to provide further analysis and computation on the labeled data in order to detect change in activity patterns and produce a functional health assessment. This functional health assessment can also be forwarded to a clinician 208 to further act upon.

Figure 3:
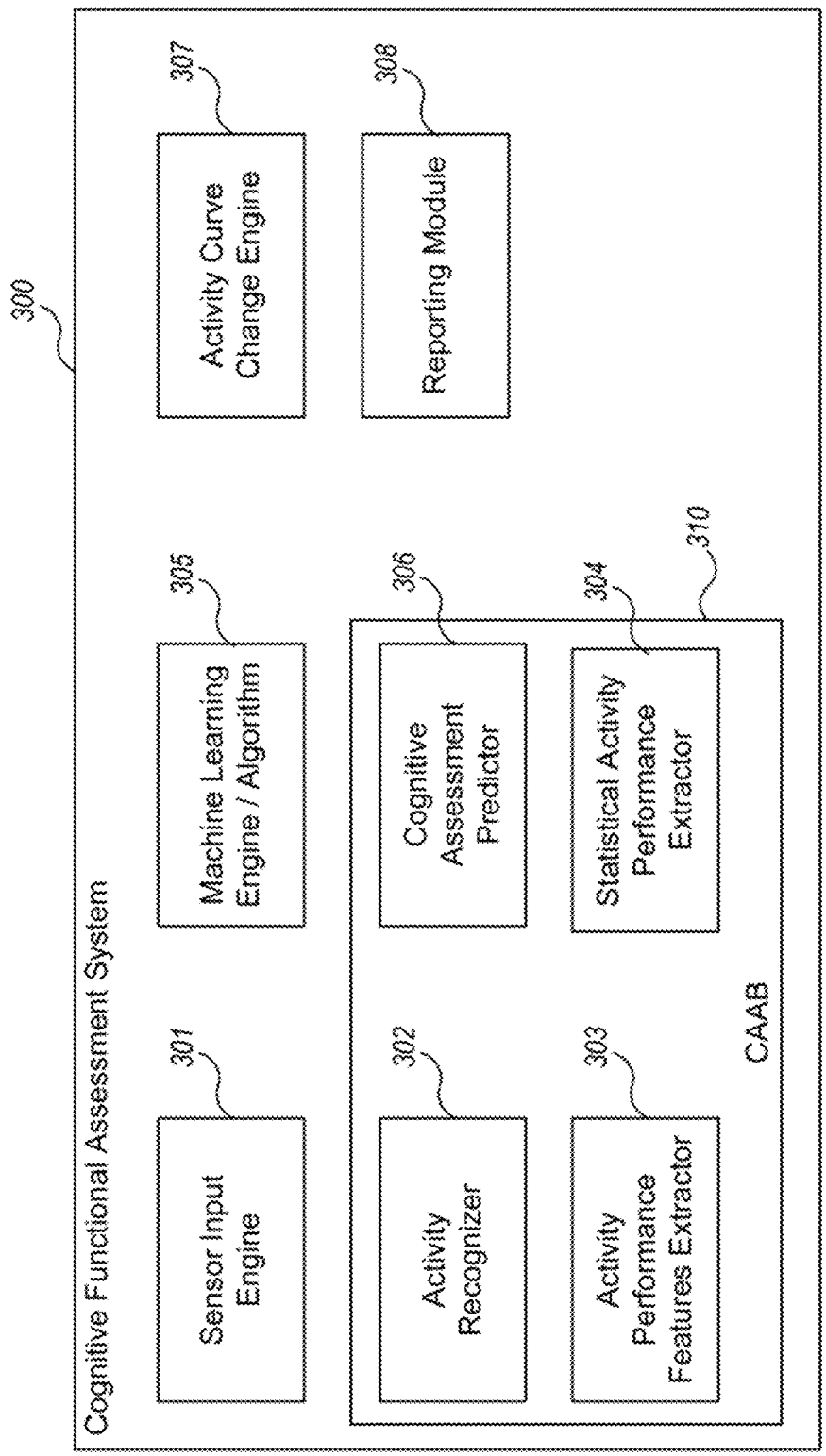
FIG. 3 is an example block diagram of components of an example Cognitive Assessment Facilitator System running one or more CAAB tools and/or activity curve tools for predicting cognitive assessment and/or for determining activity pattern changes.

FIG. 3 is an example block diagram of components of an example Cognitive Assessment Facilitator System running one or more CAAB tools and/or activity curve tools for predicting cognitive assessment and/or for determining activity pattern changes, respectively. In one example embodiment, CAFS comprises one or more functional components/modules that work together to predict cognitive assessment and/or to provide a functional assessment utilizing activity curve change analysis. For example, a Cognitive Assessment Facilitator System 300 may comprise a sensor input module 301, a machine learning engine (or algorithm as part of another component) 305, a CAAB tool 310, and activity curve change engine (activity tools) 307, and a reporting module 308. As described in FIG. 2, the CAFS receives sensor input monitoring a resident via sensor input engine 301. The CAAB then takes the input, transforms the ADL input into labeled activities via activity recognizer 302, extracts performance features from this input using activity performance features extractor 303, extracts statistical features from these activity performance features using statistical performance features extractor 304, and then primes and then uses the machine learning engine 305 via the cognitive assessment predictor 306 to predict clinic assessments which are forwarded to a clinician (or otherwise used) via reporting module 308. In some examples, the CAFS includes an activity change engine 307 which uses the activity recognize 302 (or another one) and extracts and compares change curve data to provide a functional cognitive assessment of the resident (have the characteristics of the activities changed over time). This functional assessment is then forward to a clinician (or otherwise used) via reporting module 308.

Although the techniques of smart sensor technology and the Cognitive Assessment Facilitator are generally applicable to any type of measurement of cognitive assessment, the phrase cognitive assessment is used generally to imply any type of assessment of cognitive abilities including the activities of daily living discussed herein. Also, although certain terms are used primarily herein, other terms could be used interchangeably to yield equivalent embodiments and examples. In addition, terms may have alternate spellings which may or may not be explicitly mentioned, and all such variations of terms are intended to be included.

Example embodiments described herein provide applications, tools, data structures and other support to implement a Cognitive Facilitator Assessment System to be used for predicting a clinical cognitive assessment and/or reporting functional changes in activities. Other embodiments of the described techniques may be used for other purposes. In the following description, numerous specific details are set forth, such as data formats and code sequences, etc., in order to provide a thorough understanding of the described techniques. The embodiments described also can be practiced without some of the specific details described herein, or with other specific details, such as changes with respect to the ordering of the logic, different logic, etc. Thus, the scope of the techniques and/or functions described are not limited by the particular order, selection, or decomposition of aspects described with reference to any particular routine, module, component, and the like.

Clinical Assessment Using Activity Behavior Tool (CAAB)

The Clinical Assessment using Activity Behavior tool(s) (CAAB) (such as CAAB tools 205) models a smart home resident's daily behavior and predicts the corresponding standard clinical assessment scores. In overview, CAAB extracts and uses statistical features that describe characteristics of a resident's daily activity performance to train machine learning algorithms that can then be used on the resident's further daily activity performance to predict the clinical assessment scores.

By way of introduction, the notations displayed in Table 1 below are defined and used as follows for describing functions in CAAB:

TABLE I

| | |
|---|---|
| n | Number of Activities |
| T | Total number of data collection days |
| A | Set of n activities being modeled |
| $P_i$ | Activity performance feature vector for activity i modeled over data collection period T |
| $P_{i, d, t}$ | Activity performance feature d for activity i activity on day t |
| j | Time point at which clinical measurements are made |
| $S_j$ | Clinical assessment score measured at time point j |
| W | Sliding window size |

Figure 4:
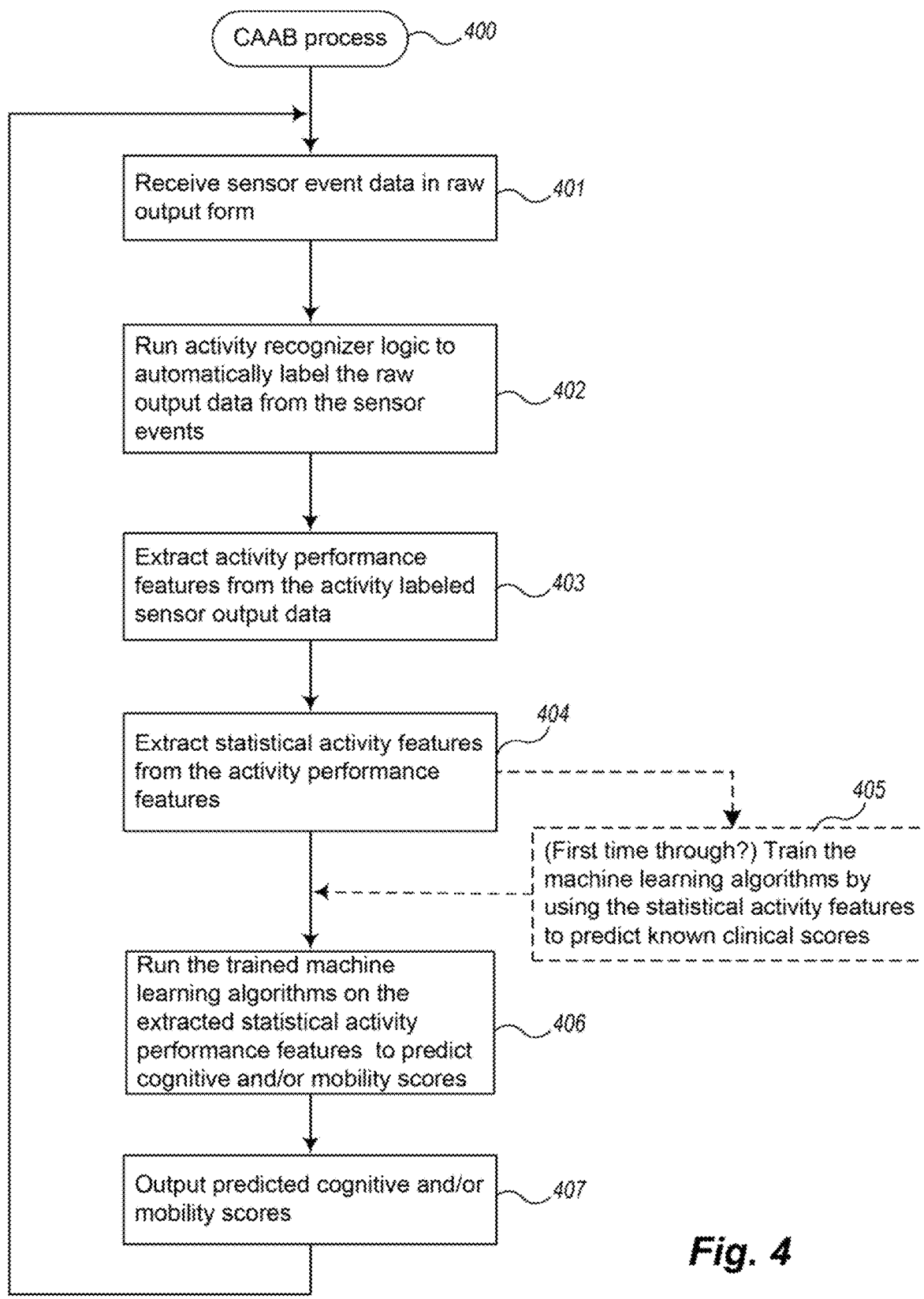
FIG. 4 is an example block diagram of an overview of an example CAAB tool process of an example Cognitive Assessment Facilitator System.

FIG. 4 is an overview block diagram of the process for providing a clinical assessment score by an example CAAB tool of an example Cognitive Assessment Facilitator System. The blocks shown in the logic of FIG. 4 may be processed by one or more components of a computing system or environment which communicate with each other over one or more networks. Smart home sensors produce a continuous sequence of time-stamped sensor readings, or sensor events. These sensors continuously generate raw sensor events while residents perform their routine activities of daily living. In block 401, the CAAB collects continuous raw output data from a set of sensors in the residence. In block 402, CAAB employs activity recognition logic or algorithms (as embodied by software, hardware, firmware or a combination or system element such as an "activity recognizer") to automatically annotate each of these sensor events with a corresponding activity label. As explained further below, the events may be streamed in, stored and forwarded, delivered in bursts, pulled from storage by the CAAB, etc. In some example CAAB tools, the activity labeling is performed in real-time (or near real-time). In some example CAAB tools, the activity recognition logic labels the raw output data from the sensor events using a sliding window as explained further below.

Activity recognition algorithms map a sequence of raw sensor events onto an activity label $A_i$, where the label is drawn from the predefined set of activities $A=\{A_1, A_2, \ldots, A_n\}$. Our activity recognition algorithm generates a label that corresponds to the last event in the sequence (i.e., the label indicates the activity that was performed when the last event was generated). Activities from set A can be recognized even when the resident interweaves them or multiple residents perform activities in parallel.

In block 403, CAAB extracts activity performance features from activity labeled smart home sensor data and utilizes these features to predict standard clinical assessment scores. Therefore, there are two steps involved in CAAB:

Modeling the ADL performance from the activity-labeled smart home sensor data; and Predicting the cognitive and mobility scores using a machine learning algorithm.

Activity Modeling:

The tool extracts a d-dimensional activity performance feature vector $P_i=<P_{i,1}, \ldots, P_{i,d}>$ to model the daily activity performance of an activity $A_i$. Observation $P_{i,d,t}$ provides a value for feature d of activity $A_i$ observed on day t ($1 \leq t \leq T$). The set of all observations in $P_i$ is used to model the performance of $A_i$ during an entire data collection period between day 1 and day T. For example, the activity "sleep" may involve features such as duration and number of sensor events detected while sleeping.

Additionally, during the same data collection period, standard clinical tests are administered for the resident every m time units, resulting in clinical assessment scores $S_1$, $S_2$, ..., $S_p$ (p=T/m). The clinical tests are administered biannually (m=180 days). Therefore, the clinical measurements are very sparse as compared to the sensor observations. The baseline clinical measurement, $S_1$, is collected after an initial 180 days of smart home monitoring.

Clinical Assessment/Clinical Assessment Scores Prediction:

CAAB's goal is to accurately predict clinical assessment scores at time k, or $S_k$, using activity performance data $P_i$ between time points j and k, j<k CAAB relies on an activity recognition (AR) algorithm to generate labeled data for the performance feature vector that is an integral component of activity modeling. The method for activity recognition is explained briefly below and explored in detail elsewhere [16].

In block 404, the CAAB extracts statistical activity features (certain statistical metrics based upon the extracted activity performance features), which are used to run a machine learning algorithm. In block 405, if this is the first time processing the activity data from a resident, the CAAB trains the machine learning algorithm (e.g., tool, system, function, etc.) using the extracted statistical activity features versus the actual clinical assessment measurement $S_1$. Then in block 406, the CAAB runs the trained machine learning algorithm on the extracted activity performance features and in block 407 outputs a predicted cognitive and/or mobility score. As shown in FIG. 2, this score can be provided, for example, to a clinician for further diagnosis or intervention.

A. Activity Recognition Algorithm

Figure 5:
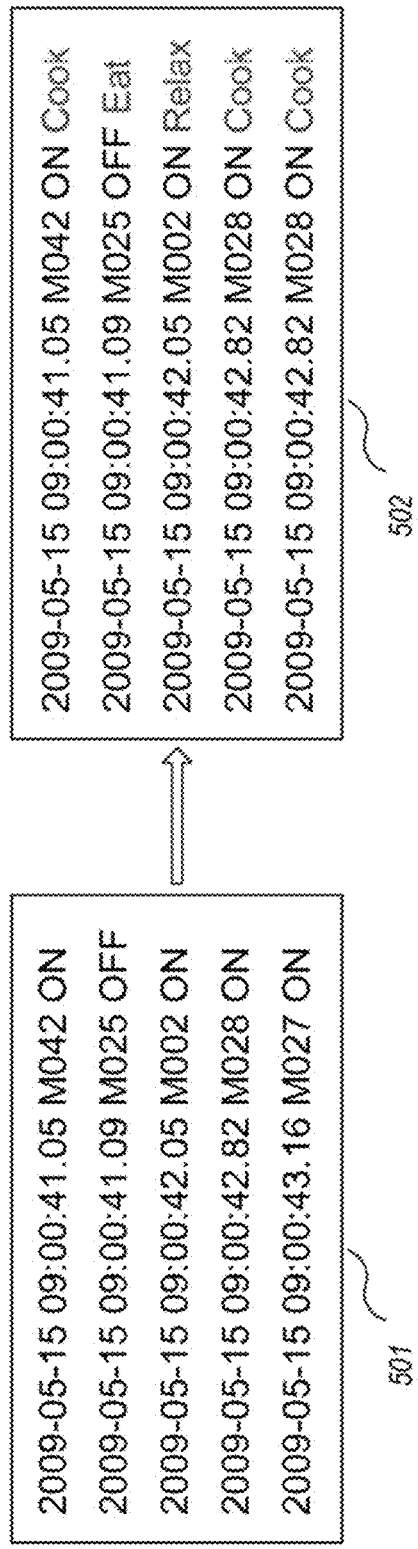
FIG. 5 is an example block diagram of activity labeling automatically performed by an activity recognition logic of an example CAFS.

FIG. 5 is an example block diagram of activity labeling automatically performed by an activity recognition logic of an example OAFS. Each sensor event is represented by four fields: date, time, sensor identifier, and sensor value. The raw sensor data does not contain activity labels. An activity recognition (AR) algorithm (running, for example, as part of CAAB or external to CAAB) labels collected raw sensor data (individual sensor events) with the corresponding activities. Data 501 shows sensor data collected prior to automatic labeling. Data 502 shows sensor data after the AR algorithm has automatically labeled the data. CAAB utilizes sensor data collected from the smart homes without altering the resident's routine and environment. Therefore, the AR approach offers an ecologically valid method to characterize the ADL parameters and assess the cognitive and physical health of a smart home resident [3].

Activity recognition algorithms label activities based on readings (or events) that are collected from smart environment sensors such as the smart home sensors shown in FIG. 1. As described earlier, the challenge of activity recognition is to map a sequence of sensor events onto a value from a set of predefined or predetermined activity labels. These activities may consist of simple ambulatory motion, such as walking and sitting, or complex basic or instrumental activities of daily living, depending upon what type of underlying sensor technologies and learning algorithms are used.

The activity recognition algorithm used by CAAB (AR) [22], recognizes activities of daily living, such as cooking, eating, and sleeping using streaming sensor data from environmental sensors such as the motion sensors and door sensors described with reference to FIG. 1. These motion and door sensors are discrete-event sensors with binary states (On/Off, Open/Closed). In an example CAAB, human annotators label one month of sensor data from each smart home with predefined activity labels to provide the ground truth activity labels for training and evaluating the algorithm. The inter-annotator reliability (Cohen's Kappa) values of the labeled activities in the sensor data ranged from 0:70 to 0:92, which is considered moderate to substantial reliability. The trained model was then used to generate activity labels for all of the unlabeled sensor data.

AR identifies activity labels in real time as sensor event sequences are observed. Thus, the algorithm can be employed on continuously streamed data. This is accomplished by moving a sliding window over the data and using the sensor events within the window to provide a context for labeling the most recent event in the window. The window size is dynamically calculated based on the current sensor. Each event within the window is weighted based on its time offset and mutual information value relative to the last event in the window. This allows the events to be discarded that are likely due to other activities being performed in an interwoven or parallel manner. A feature vector is calculated using accumulated sensor events in a window from the labeled sensor data collected over a month. The feature vector contains information such as time of the first and last sensor events, temporal span of the window, and influences of all other sensors on the sensor generating the most recent event based on mutual information. Currently, the AR used by an example CAAB embodiment recognizes the activities monitored with 95% accuracy based on 3-fold cross validation. An example of activity-labeled sensor data is presented in FIG. 2 of [22]. More details on this and other approaches to activity recognition can be found in the literature [16]. The CAAB tools can incorporate activity recognition algorithms in addition to that described here.

B. Modeling Performances of Activities and Mobility Performances

The first step of the CAAB tool once the data is annotated is to model the performance of the activities in set A (steps 403 of FIG. 4). CAAB models activity performance by extracting relevant features from the activity-labeled sensor data. For each activity $A_i \in A$, the CAAB can represent such performance features using the d-dimensional activity performance feature vector $P_i=<P_{i,1}, P_{i,2}, \ldots, P_{i,d}>$.

Depending upon the nature of the sensor data and the performance window we want to monitor, the CAAB can aggregate activity performance $P_i$ for activity $A_i$ over a day, week, or other time period. In one example CAAB, activity performance features were aggregated over a day period (the time unit is one day). For example, if the sleep activity performance $P_{i,1,t}$ is calculated as the time spent sleeping in the bedroom on day t, the observation $P_{i,1,t+1}$ occurs one day after observation $P_{i,1,t}$. For each individual, the CAAB calculates activity performance features for the entire data collection period T for all activities in the activity set A ($1 \le t \le T$).

Activity performance is modeled by an example CAAB using two (d=2) specific activity performance features: a time-based feature and a sensor-based feature $\{P_{i,1}, P_{i,2}\}$. Feature $P_{i,1}$ represents the duration of activity $A_i$ and $P_{i,2}$ represents the number of sensor events generated during activity $A_i$. These two features are generalizable to other activities, are easily interpretable, and can model how the residents perform their daily activities [15]. In addition to capturing activity performance, CAAB also represents and monitors a person's overall mobility. Mobility refers to movement generated while performing varied activities (as opposed to representing a single activity of its own) and is therefore represented using two different types of features: the number of sensor events triggered throughout the home and the total distance that is covered by movement throughout the course of a single day (Table 2 below).

TABLE 2

| Group | Variable | Activity Performance Features |
|---|---|---|
| Mobility | Mobility | Total distance traveled, # Total sensor events |
| Sleep | Sleep | Sleep duration, # Sleep sensor events |
| | Bed toilet transition | Bed toilet transition duration |
| ADL | Cook | Cook Duration |
| | Eat | Eat Duration |
| | Relax | Relax Duration |
| | Personal Hygiene | Personal Hygiene Duration |
| | Leave Home | Leave Home Duration |

C. Selection of ADLs

In an example CAAB, a subset of automatically-labeled resident daily activities is modeled. These activities are sleep, bed to toilet (a common type of sleep interruption), cook, eat, relax, and personal hygiene. The CAAB also captures and model a resident's total mobility in the home.

1) Sleep: The effects of aging include changes in sleep patterns that may influence cognitive and functional status. For example, individuals over the age of 75 have been found to experience greater fragmentation in nighttime sleep (e.g., [23]), which concurrently causes decreased total sleep time and sleep efficiency. Sleep problems in older adults can affect cognitive abilities [24] and have been associated with decreased functional status and quality of life. Moreover, individuals with dementia often experience significant disruption of the sleep wake cycle. Thus, the effects of sleep on the health of older adults are important clinical construct that both clinicians and caregivers are interested in understanding [25].

Using activity recognition, the CAAB recognizes sensor events that correspond to sleep (in the bedroom, as opposed to naps taken outside the bedroom) and bed-to-toilet activities. The CAAB then extracts the time spent and number of sensor events features that correspond to these two activities. As listed in Table 2, four features model a smart home resident's sleep activity. The value for the time-based sleep feature is calculated as the total number of minutes spent in sleep on a particular day and the value for the sensor-based sleep feature is calculated as the number of sensor events that are triggered over the course of one day while the resident slept. Similarly, the time-based bed to toilet feature is calculated as the total number of minutes spent in bed to toilet activity on a particular day. An example CAAB excludes the sensor based feature that calculates the number of times sensor events are triggered on bed to toilet activity because the data shows that the number of sensor events generated when performing the bed to toilet activity is often very low. Because of the known importance of sleep and its relationship with physical and cognitive health, CAAB conducts a separate analysis of sleep and bed to toilet parameters from the other activities that are analyzed as a group [25], [26].

2) Mobility: Mobility is the ability of an individual to move around the individual's home environment and the community. Mobility impairments limit an individual's ability to maintain independence and quality of life and are common predictors of institutionalization among older adults [27]. Evidence supports a close connection between executive brain function and walking speed [28]. Therefore, CAAB separately models mobility as an everyday behavioral feature. CAAB models the mobility of a smart home resident based on the number of sensor events they trigger and the total distance they cover in a day while in the home (estimated based on known distances between motion sensors placed in the home). As listed in Table 2, the value for the distance-based mobility feature is calculated as the total distance covered by a resident in one day (the example aggregation time period) while inside the home. Similarly, the value for the sensor-based mobility feature is calculated as the number of sensor events that a resident triggers over the course of one day while moving around in the home.

3) Activities of Daily Living: Basic activities of daily living (e.g., eating, grooming) and the more complex instrumental activities of daily living (IADLs; e.g., cooking, managing finances) are fundamental to independent living. Data indicate that increased difficulties in everyday activity completion (e.g., greater task inefficiencies, longer activity completion times) occur with older age [29], [30]. Clinical studies have also demonstrated that individuals diagnosed with MCI experience greater difficulties (e.g., increased omission errors) completing everyday activities when compared with healthy controls [31], [32]. Therefore, clinicians argue the importance of understanding the course of functional change given the potential implications for developing methods for both prevention and early intervention [30]. The example CAAB considers five activities of daily living (in addition to sleep): cook, eat, personal hygiene, leave home, and relax. Of note the "relax" activity represents a combination of watching TV, reading, and napping that typically takes place in a single location other than the bedroom where the resident spends time doing these activities, such as a favorite chair. The example CAAB focuses on these activities because they are activities of daily living that are important for characterizing daily routines and assessing functional independence. For each of these activities, CAAB calculates the total activity duration. Our data shows the number of sensor events generated when performing these activities is often very low. Thus, for these activities, features were excluded that calculate number of times sensor events are triggered. As listed in Table 2, CAAB calculates the value for the time-based ADL feature as the total number of minutes spent in an activity on a particular day.

D. Activity Feature Extraction

The second step of the CAAB tool after sensor event annotation (e.g., step 404 of FIG. 4) is to extract statistical features from the activity performance vector generated in the prior step (e.g., step 403 of FIG. 4). CAAB extracts features from the time series-based representation of activity performance and uses these to train a machine-learning algorithm (e.g., step 405 of FIG. 4). Namely, CAAB extracts four standard time series features and one new change feature. These five features will be referred to as "statistical activity features." Table 3 lists an example set of statistical activity features. In Table 3, μ is the mean of the activity performance features p of size n.

TABLE 3

| 1 | Variance | Variance is the measure of spread. | $Var(p) = \Sigma_{k=1}^{n}(p_i - \mu)^2$ |
|---|---|---|---|
| 2 | Auto-correlation | Auto-correlation(AC) is the similarity between observations that are displaced in time. Calculate autocorrelation at lag 1. | $AC-lag1(p) = \left( \dfrac{\sum_{i=1}^{n-1}(p_i - \mu)(p_{i+1} - \mu)}{\sum_{n=1}^{n}(p_i - \mu)^2} \right)$ |
| 3 | Skewness | Skewness measures the degree of asymmetry in the distribution of values. | $skewness(p) = \dfrac{\frac{1}{n}\sum_{i=1}^{n}(p_i - \mu)^3}{\left(\frac{1}{n}\sum_{i=1}^{n}(p_i - \mu)^2\right)^{\frac{3}{2}}}$ |
| 4 | Kurtosis | Kurtosis measures the amount of peakedness of the distribution toward the mean. | $kurtosis(p) = \dfrac{\frac{1}{n}\sum_{i=1}^{n}(p_i - \mu)^4}{\left(\frac{1}{n}\sum_{i=1}^{n}(p_i - \mu)^2\right)^{3}}$ |
| 5 | Change | Change characterizes the amount of change in an individual's activity performance over time. | See Algorithm 1 |

1) Statistical activity features: To calculate the first four features, CAAB runs a sliding window (e.g., window size, W=30 days) over each of the activity performance features listed in Table 2 and calculates the statistical activity features (e.g., variance, autocorrelation, skewness, and kurtosis) using the observations from data that falls within the sliding window. The sliding window starts at one clinical assessment time point and ends at the next assessment time point, thus capturing all of the behavior data that occurred between two subsequent assessments. For example, CAAB can calculate the variance, autocorrelation, skewness, and kurtosis of the duration feature for each activity based on duration observations that fall inside each W sized data window. CAAB repeats the process and calculates these four statistical activity features for all other activity performance features for all of the activities in set A. Before calculating these features, CAAB first removes the time series trend from the sliding window observations in order to remove the effect of non-stationary components (e.g. periodic components) in the time series [33]. For this step, CAAB fits a Gaussian or a linear trend to the data within the sliding window. CAAB then detrends the data by subtracting the fitted trend from the data. CAAB slides the window by one day (skip size=1) and re-computes all of the statistical activity features. For each feature, CAAB slides a window through the sensor home data and computes the final feature values as an average over all of the windows. Algorithm 1 can be utilized to compute these steps.

Algorithm 1
ALGORITHM 1 Extracting statistical activity features

```
1:   Input: Activity performance features
2:   Output: Statistical activity features
3:   Initialize: Feature vector
4:   // T_1 and T_2 are two consecutive clinical testing time points
5:   Given: T_1; T_2
6:   Given: skip size = 1
7:   while T_1 < (T_2 - W) do
8:      for each activity performance feature do:
9:         Place a window of size W at T_1;
10:        Remove missing observations and detrend based on
           the observations that fall into this window;
11:        Calculate the variance, autocorrelation, skewness,
           kurtosis and change features (Algorithm 2) using the
           observations in the window;
12:        Append these values to the feature vector;
13:        T_2 = T_1 + skip size;
14:     end foreach
15:  end while
16:  return average (Feature matrix)
```

In addition to these four different time series features, CAAB uses a fifth feature, a change-based feature, to characterize the amount of change in an individual's activity performance. Algorithm 2 details the steps in calculating this new feature. In order to compute this feature, CAAB uses a sliding window of size W days and divides the activity performance feature observations that fall in W into two different groups. The first group contains feature observations that fall in the first half of W and second group contains feature observations that fall in the other half. CAAB then compares between these two groups of feature observations using a change detection algorithm. For example, in one example CAAB the Hotelling-T test algorithm [34] is used. However, different CAAB implementations can also apply other change detection algorithms. CAAB then slides the window by one day (skip size=1) and re-computes the change feature. CAAB calculates the final change value as the average over all windows. Similar to the other four statistical activity features computed, CAAB computes the value of the change feature for each of the activity performance features listed in Table 2.

Algorithm 2
ALGORITHM 2 Calculation of change feature

```
1:   Input: Activity performance features
2:   Initialize: CH = [ ]
3:   // T_1 and T_2 are two consecutive clinical testing time points
4:   Given: T_1; T_2
5:   Given: skip size = 1
6:   while T_1 < (T_2 - W) do
7:      for each activity performance feature do:
8:         Place a window of size W at T_1;
9:         Remove missing values that fall into this window;
10:        Put first half of W in the group A and second half in
           the group B;
11:        // Returns True or False;
12:        change = Hotelling T-test (A, B);
13:        append (CH, change)
13:        T_1 = T_1 + skip size;
14:     end foreach;
15:  end while;
16:  return average(CH).
```

Of note, the change feature is different from the variance feature that CAAB calculates earlier. While variance measures the variability of samples around its mean, the change feature empirically calculates the "chance" of observing a change when two sample groups each of size n from the given activity performance features are compared with each other. Here, a higher amount of detected change indicates a greater chance of detecting changes in the activity performance feature.

E. Clinical Assessment

In the final steps of the CAAB tool (e.g., steps 405-407 of FIG. 4), CAAB predicts the clinical assessment scores of the residents being monitored using the smart home sensors using the activity performance features computed from the activity labeled sensor data. CAAB first aligns the sensor-based data collection date with the clinical assessment-based data collection date before extracting statistical activity features (in step 404 of FIG. 4). After extracting features and aligning the data, CAAB then trains a supervised machine learning algorithm and predicts the clinical assessment scores (step 405 of FIG. 4). To accomplish this goal, CAAB extracts statistical activity features from the activity performance features that lie between any given two consecutive clinical testing points, t1 and t2. Similarly, it obtains the clinical score S2 (or S1) at time point t2 (or t1). It considers the pair, statistical activity features and clinical score S2, as a point in the dataset and repeats the process for each of resident that it is monitoring and for every pair of the consecutive clinical testing points. Algorithm 3 summarizes the steps involved to prepare the dataset to train the supervised machine learning algorithm.

| Algorithm 3 |
|---|
| ALGORITHM 3 Training Set Creation |
| 1: Input: Activity performance features for all residents |
| 2: Output: Training set to train the learning algorithm |
| 3: Initialize: Empty training set TrSet |
| 4: for each resident do: |
| 5:   for each consecutive clinical testing point $T_1$ and $T_2$ do: |
| 6:     F = CAAB (statistical activity performance features between $T_1$ and $T_2$); |
| 7:     S = clinical score ($T_1$, $T_2$) and $T_2$; |
| 8:     Append (F, S, TrSet); |
| 9:   end for each; |
| 10: end for each. |

The CAAB is then able to predict the clinical assessment scores (see step 406 of FIG. 4) using the machine learning algorithm (tool, system, etc.). As explained above, CAAB trains a learning algorithm to learn a relationship between statistical activity features and the clinical assessment scores using the dataset that is initially constructed. (Block 405 of FIG. 4 shown in dashed lines as it is only performed initially or when the machine learning tool is updated). Then in the final step (block 406 of FIG. 4) for each resident, at each time point (except the first one), CAAB predicts the clinical assessment scores using a machine learning algorithm such as an SVM (support vector machine). The machine learning algorithm may be part of the CAAB, a separate computing system, a call, for example, to an algorithm provided by a software library of functions, or the like.

Of note the CAAB predicts clinical assessment scores based on the relationship that the learning algorithm models between the clinical assessment scores and behavior features. This approach is followed because there are very few clinical observations for a resident. Furthermore, the CAAB computes activity performance features by temporally following an individual over a period and computes statistical activity features by comparing past observations with current observations. In this way, CAAB uses an individual as their own baseline for predictive assessment.

Modeling and Evaluating Patterns of Activities Using Activity Curve Tools

Many pervasive computing applications (also known as ubiquitous computing applications) such as home automation, activity aware interventions, and health assessment require analyzing and understanding activity-based behavioral patterns. The performance of such applications depends on the ability to correctly learn a model of general daily activity behavior from a large amount of data and be able to predict when such daily behavior is likely to continue or change. These big data-based approaches to activity modeling can then in turn be used to provide effective activity-aware services such as improved healthcare.

Activity recognition lies at the heart of any pervasive computing approach to modeling behavioral routines. As described above, an activity recognition algorithm maps a sensor reading or sequence of readings to a corresponding activity label. In order to answer general questions related to daily activity patterns, such information needs to be transformed to a higher-level representation. For example, questions such as how average daily activity patterns have changed over a year, or generally what hours did a particular individual sleep last month are difficult to answer using raw output from activity recognition algorithms. However, many pervasive computing applications such as home automation and health assessment require answering such questions.

Obtaining higher-level representations or models of activities has several additional advantages. Higher-level representations can abstract variations in day-to-day activity routines. For example, wake-up times in the morning may be slightly different each day even if the overall routine is fairly stable. Additionally, such representations simplify the task of modeling an individual's daily routine and at the same time make visualization and interpretation of daily activity routines easy. Collecting big datasets over long periods of time allows us to abstract activity models over such daily variations. Such representations aid with the process of identifying long-term changes in a behavioral routine.

For example, consider the following description highlighting aspects of an individual's routine at two different points in time:

Month of March 2012: Sleep at 10:00 PM, get up at 6:00 AM, eat breakfast at 7:00 AM, eat lunch at 12:00 PM, go out for a walk at 4:00 PM, and dine at 8:00 PM.

Month of September 2013: Sleep at 8:00 PM, wake up frequently during the night, get up at 10:00 AM, no breakfast, eat lunch at 11 AM, no going out for a walk, and dine at 7:00 PM.

Note that each of these sample activity-based descriptions is aggregated over a one-month period and therefore describes a general routine that is maintained over a prolonged period of time. Based on these descriptions we also note changes in the routine from the first observation to the second. From this example, we can infer that by September 2013 the observed individual was experiencing disturbances in sleep, was skipping meals, and stopped exercising. Determining if the overall daily activity patterns has changed may be difficult based only on the raw sensor data or even based on event-by-event labels from an activity recognition algorithm. Such questions can be more easily answered by comparing two higher-level representations of these activity patterns.

Example embodiments provide an Activity Curve tool, such as the Activity Curve Change Engine 307 of FIG. 3 to model an individual's generalized daily activity routines. The activity curve modeling algorithm (for example, as implemented by code logic) employed by the Activity Curve tool uses activity-labeled sensor events to learn a higher-level representation of the individual's regular routine. These activity labels are automatically-recognized using an activity recognition algorithm.

The Activity Curve tools use a Permutation-based Change detection in Activity Routine (PCAR) algorithm as implemented for example by code logic to compare activity curves between different time points in order to detect changes in an activity routine. The tools and algorithms have been validated using longitudinal smart home sensor data collected by monitoring everyday behavior of residents over two years. The activity curve modeling algorithm and the PCAR algorithm can be used to perform important pervasive computing tasks such as automated assessment of an individual's functional health.

The activity curve modeling algorithm implemented by the Activity Curve tool provides a generic activity curve model that can be calculated both from the output of an activity recognition algorithm as well as using other algorithms from prior studies. The activity curve model facilitates answering more complex questions related to activity routines such as whether changes in an activity routine have occurred or not. In an example embodiment, activity curve tool uses the output from an activity recognition algorithm to calculate the activity curves.

The PCAR algorithm detects significant changes in activity curves based on a permutation-based two-sample test using symmetric Kullback-Leibler divergence as a distance metric. The Activity Curve (AC) tool for detecting changes in activity routines has some similarities with activity tracking algorithms that have been previously proposed [52], [53]. However, these previously proposed activity-tracking algorithms discover and track changes in sensor sequence patterns for the purpose of adapting home automation strategies. In contrast, the Activity Curve tool tracks changes in the distribution of automatically-recognized activity patterns.

Activity Curve

An activity curve is a model that represents an individual's generalized activity routine. The AC tool models activity routines for a day-long period but the time period can be changed as needed. The activity curve uses automatically recognized activity labels to express daily behavioral characteristics based on the timing of recognized activities. Typically, a continuous sequence of time-stamped sensor events is available.

In summary, the AC tool first uses an activity recognition algorithm to annotate each of these sensor events with an activity label. Activity recognition algorithms map a sequence of sensor events $\{e_1\ e_2, \ldots, e_n\}$ onto the corresponding activity label $A_i$, where the label is drawn from the predefined set of activity classes $A_i = \{A_1\ A_2, \ldots, A_n\}$.

We note that prevalence of common activities differs by the time of day. For example, the "sleep" activity dominates the prevalent distribution of activities at midnight and the "cook breakfast" and "eat breakfast" activities dominate the early morning hours. To capture such differences in activity patterns throughout the day, the AC tool segments the day-long observation period into m equal-size consecutive windows, or time intervals, and define probability distributions over activities, or activity distributions, for each of these time intervals (see FIG. 1 for an example). An activity curve is a compilation of these activity distributions for the entire day-long period.

In general, activity routines tend to vary from one day to the next. For example, we may wake up at 6:30 AM and eat breakfast at 7:15 AM one day while we might wake up at 7:30 AM and eat breakfast at 8:00 AM the next day. In order to generalize the activity curve model over such day-to-day variations in activity routines, we define the notion of an aggregated activity curve that is calculated over an aggregation window of x days.

Definition 1.

Given a time interval t, an activity distribution models the daily routine based on the predefined set of activities A as a probability distribution over activities in A. The probability distribution can be estimated from sample data based on the normalized time an individual spends on a predefined set of n activities during time intervals t as observed during one or more days.

An activity distribution for time interval t is a n-element set $D_t = \{d_{t,1}, d_{t,2}, \ldots, d_{t,n}\}$ whose length is equal to that of the activity set A. The i-th element in an activity distribution, $d_{t,i}$, represents the probability of performing activity $A_i$ during time interval t.

To model a person's overall daily activity routine, the AC tool uses m activity distributions corresponding to each of the m time intervals. The AC tool can then construct an activity curve by collecting activity distributions that model daily activity patterns at all different times of the day.

Definition 2.

An activity curve C is the compilation of activity distributions $D_t$ ordered by time interval t.

The length of an activity curve is m. The model that compiles activity distributions is referred to as an "activity curve," because if we consider the activity distribution of activity $A_i$ for all time intervals 1, 2, ..., m, these activity distributions form a curve that represents the "fraction of a time" that an individual is likely to perform activity $A_i$ over successive time intervals.

The AC tool calculates an aggregated activity distribution $\hat{D}_t$ for time interval t by aggregating activity distributions $D_{k,t}$ (1≤k≤x) over an aggregation window of x days. If $D_{1,t}$, $D_{2,t}$, ... $D_{x,t}$ are activity distributions for the t-th time interval aggregated over a window of x days and follow normal distributions, then we can define an aggregated activity distribution as follows.

Definition 3.

An aggregated activity distribution $\hat{D}_t$ at time interval t is the maximum likelihood estimate of the mean that is obtained from activity distributions $D_{k,t}$ (1≤k≤x) that fall within an aggregation window of size x.

We can write the aggregated activity distribution $\hat{D}_t$ at time interval t as shown in Eq. (1):

$$\hat{D}_t = \sum_{k=1}^{x} \frac{D_{k,t}}{x}. \quad (1)$$

Definition 4.

An aggregated activity curve is the compilation of aggregated activity distributions obtained over an aggregation window of size x.

If $\Sigma = \{C_1, C_2, C_3, \ldots, C_x\}$ is a set of activity curves over an aggregation window of size=x days, we can represent an aggregated activity curve over $\Sigma$ as $C^\Sigma$. The aggregated activity curve $C^\Sigma$ compiles the aggregated activity distributions, $\hat{D}_t$. FIG. 6 illustrates an example of an aggregated activity curve that models three different activities: sleep, bed toilet transition, and other.

Activity Distribution Distance

We calculate the distance between two activity distributions using the Kullback-Leibler (KL) divergence measure. We assume that the activity distributions model the same activity set A for the same time interval size and aggregation window size. The KL divergence between two activity distributions
$D_1 = \{d_{1,1}, d_{1,2}, \ldots d_{1,i}, \ldots, d_{1,n}\}$ and $D_2 = \{d_{2,1}, d_{2,2}, \ldots, d_{2,i}, \ldots, d_{2,n}\}$ is defined as shown in Eq. (2):

$$D_{KL}(D_1 \| D_2) = \sum_{i=1}^{n} d_{1,i} \log \frac{d_{1,i}}{d_{2,i}}. \quad (2)$$

We note that the standard KL distance metric is a non-symmetric measure of the differences between two probability distributions $D_1$ and $D_2$. Therefore, we use a symmetric version of the Kullback-Leibler divergence between activity distributions $D_1$ and $D_2$, which is defined as shown in Eq. (3). Throughout the remainder of the paper, our discussion of KL divergence will refer to this symmetric version of the KL divergence measure.

$$SD_{KL}(D_1 \| D_2) = D_{KL}(D_1 \| D_2) + (D_2 \| D_1) \quad (3)$$

Before defining the distance between two activity curves $C_1$ and $C_2$ of length m, we first need to align the activity distributions in the activity curves (as described later). As a result of the alignment step, we obtain a vector of alignment pairs $\Gamma = (p, q)$ of length $l = |\Gamma|$ that aligns an activity distribution at time interval p ($1 \le p \le m$) of activity curve $C_1$ with activity distribution at time interval q ($1 \le q \le m$) of activity curve $C_2$. We calculate the total distance, $SD_{KL}(C_1 \| C_2)$, between two activity curves, $C_1$ and $C_2$, as the sum of distances between each aligned activity distribution for the two activity curves, as shown in Eq. (4).

$$SD_{KL}(C_1 \| C_2) = \sum_{\alpha=1}^{l} SD_{KL}(D_{1,p} \| D_{2,q}) \quad (4)$$

such that $\Gamma_\alpha = (p, q)$ where $D_{1,p}$ and $D_{1,q}$ are the activity distributions that belong to activity curves $C_1$ and $C_2$ at time intervals p and q, respectively.

Determining the Size of an Aggregation Window

Daily activity routines are performed differently from one day to the next. As a result, the daily activity curve that models these activity routines will vary from one day to the next. The activity curve tools want to calculate an aggregated activity curve that generalizes over minor day-to-day variations while still capturing the typical routine behavior. When determining the appropriate size of an aggregation window, the goal is to find the smallest possible number of days that is considered stable. The tool determine that an aggregated activity curve is stable if the shape of the curve remains mostly unchanged when more days are added to the aggregation window. By keeping the aggregation window small, the model can be more sensitive to significant changes in routine behavior. If the window is too small it will not be general enough to encompass normal variations in daily routines. Algorithm 1 is used to determine the minimum length of an aggregate window that is required to calculate a stable, representative aggregated activity curve for a particular time interval. A minimum aggregate window size $x_{min}$ is chosen such that no smaller window would ensure the stability criterion.

To determine the ideal aggregation window size, the algorithm starts with a window of size x=2 and considers the corresponding aggregated activity curve $C^\Sigma$, aggregated from the set of individual activity curves $\Sigma = \{C_1, \ldots, C_x\}$. We estimate the distance between $C_x^\Sigma$ and $C_{x+1}^\Sigma$. If the distance is greater than a predefined threshold T, we increase the window size. Therefore, if $SD_{KL}(C_x^\Sigma \| C_{x+1}^\Sigma) < T$ and $SD_{KL}(C_{x+1}^\Sigma \| C_{x+2}^\Sigma) < T$, then x is selected as the representative aggregation window size, otherwise the size of the aggregation window is increased by one and the process repeated. This process is shown in Algorithm 4.

Algorithm 4
ALGORITHM 4 Aggregation Size ($\Sigma$, T)

1: // Calculate the minimum size of an aggregation window
2: $\Sigma = \{C_1, C_2, \ldots, C_N\}$ for each of the N days in the input data.
3: // Return the minimum aggregation window size.
4: initialize x = 2;
5: repeat:
6:    Create $C_x^\Sigma$, aggregated activity curve for window size x;
7:    Create $C_{x+1}^\Sigma$, aggregated activity curve for window size x + 1;
8:    Create $C_{x+2}^\Sigma$, aggregated activity curve for window size x + 2;
9:    Compute $d_1$ = distance between two aggregated activity curves $SD_{KL}(C_x^\Sigma \| C_{x+1}^\Sigma)$;
10:    Compute $d_2$ = distance between two aggregated activity curves $SD_{KL}(C_{x+1}^\Sigma \| C_{x+2}^\Sigma)$;
12:    If $d_1 > T$ and $d_2 > T$, then x = x + 1;
13:    else return x;
14: until x < N;

Activity Curve Alignment

In order to compute similarity (or distance) between two activity curves, we need to compare each of the activity distributions that belong to these two activity curves. However, we first need to determine which pairs of distributions to compare by considering alternative distribution alignment techniques. Activity curve alignment can be performed based on aligning the same time of day between two curves. Alternatively, we can try to maximally align the activity occurrences between two curves before performing such a comparison. Here we provide details for these two alignment techniques.

Time Interval-Based Activity Curve Alignment

The time interval-based activity curve alignment technique presumes that distributions between two curves should be aligned based on time of day and thus aligns activity distributions between two activity curves if the time intervals are the same. In essence, this method does not make any extra effort to align activities that occur at different times in the distribution, but simply compares the activity distributions based on time of day alone. If $C_1$ and $C_2$ are two activity curves of length m, the time interval-based activity distribution alignment method aligns the corresponding activity distributions using a vector of alignment pairs, $\Gamma = (r, r)$. This technique aligns an activity distribution at time interval r ($1 \le r \le m$) of activity curve $C_1$ with activity distribution at time interval r($1 \le r \le m$) of activity curve $C_2$.

Dynamic Time Warping-Based Activity Curve Alignment

A person's routine may be relatively stable, even though there are minute changes in the time an activity occurs or the duration of a particular activity. For example, an individual may sleep at 10:00 PM one day, an hour earlier at 9:00 PM the next day, an hour later at 11:00 PM a few days later, and eventually go back to sleeping at 10:00 PM. Aligning activity distributions using dynamic time warping allows the tool to maximally align common activities before comparing two activity curves. Such an alignment accommodates activity time changes that are shifted temporally backward (for example, an hour earlier), forward (for example, an hour later), expanded (longer duration), compressed (shorter duration), or not changed at all from one day to another. The tool optimizes activity alignment using Dynamic Time Warping(DTW) to align distributions between two activity curves. Dynamic time warping finds an optimal alignment or warping path between activity curves. This optimal warping path has minimal total cost among all possible warping paths. The tool uses the symmetric KL distance metric that we previously mentioned to compute this warping path. The warping path has the following three main properties:

Boundary property: The first and last elements (activity distributions) from the two activity curves are always aligned with each other.

Monotonicity property: Paths are not allowed to move backwards.

Step size property: No activity distributions are omitted from the curve alignment.

We also note that due to the monotonicity property, DTW does not allow backward alignments. However, as we have seen in practice, activity distributions can be shifted temporally backward and/or temporally forward. Therefore, the standard approach is modified to perform two independent iterations of DTW:

In forward dynamic time warping, we start from the first activity distribution and move forward in time toward the last activity distribution to find an optimal alignment between activity curves that are similar in the forward time direction.

In backward dynamic time warping, we start from the last activity distribution and move backward in time toward the first activity distribution to find an optimal alignment between activity curves that are similar in the backward time direction.

If $C_1$ and $C_2$ are two activity curves of length m, the DTW-based activity distribution alignment outputs two alignment vectors, $\Gamma_{forward}=(u, v)$ of length $l_{toward}$, and $\Gamma_{backward}=(r, s)$ of length $l_{backward}$, respectively. The forward DTW aligns an activity distribution from curve $C_1$ at time interval u ($1 \leq u \leq m$) with an activity distribution from curve $C_2$ at time interval v ($1 \leq v \leq m$). Similarly, the backward DTW aligns an activity distribution from curve $C_1$ at time interval r ($1 \leq r \leq m$) with an activity distribution from curve $C_2$ at time interval s ($1 \leq s \leq m$). The DTW method outputs whichever vector, $\Gamma_{forward}$ or $\Gamma_{backward}$, that results in the maximal alignment between the two distributions and thus minimizes the difference. The activity curve tool will utilize these two different alignment techniques in the PCAR algorithm to detect changes between two aggregated activity curves and calculate change scores.

PCAR

Based on this notion of an activity curve, we now introduce our Permutation-based Change Detection in Activity Routine (PCAR) algorithm. This algorithm, which is used by the activity curve tool, identifies and quantifies changes in an activity routine. PCAR operates on the assumption that daily activities are scheduled according to a routine and are not scheduled randomly. For example, we regularly "wake up", "bathe" and "have breakfast" in the morning and "dine" and "relax" in the evening. In contrast, we rarely dine in the middle of night. Such regularities are useful, for example, to determine if there are significant changes in lifestyle behavior that might indicate changes in cognitive or physical health.

Permutation-Based Two-Sample Test

PCAR identifies significant changes in an activity routine using a two-sample permutation test [64]. The permutation based technique provides a data-driven approach to calculate an empirical distribution of a test statistic. The empirical distribution of a test statistic is obtained by calculating the test statistic after randomly shuffling (rearranging) the data a specified number of times. The permutation-based test is exact if the joint distributions of rearranged samples are the same as the joint distribution of the original samples. In other words, the samples are exchangeable when the null hypothesis is true. This type of test allows us to determine the significant difference between two aggregated activity curves. We use a permutation-based test to perform a two-sample homogeneity test. In a two-sample homogeneity test, we test the null hypothesis that the two samples come from the same probability distribution versus the alternate hypothesis that they come from different probability distributions.

Changes in Activity Distributions

We use the permutation-based two-sample test to determine whether there is a significant change among a set of activity distributions at a particular time interval. We formulate the null hypothesis that the set of activity distributions comprising two activity curves are identical versus the alternative hypothesis that the set of activity distributions is significantly different between the two aggregated activity curves. We test the hypothesis of a significant change between two aggregated activity distributions, $\hat{D}_{1,t}$ and $\hat{D}_{2,t}$.

Calculate the test statistic: Calculate the test statistic $\text{Dist}_t = SD_{KL}(\hat{D}_{1,t} \| \hat{D}_{2,t})$ between the two aggregated activity distributions.

Permutation: Randomly shuffle individual activity distributions between the two aggregated distributions and recalculate the aggregated distributions $\hat{D}_{1,t}$ and $\hat{D}_{2,t}$. Calculate the KL divergence between the new aggregated activity distributions $\hat{\text{Dist}}_t = SD_{KL}(\hat{D}_{1,t} \| \hat{D}_{2,t})$. Repeat the process a specified number of times to obtain an empirical distribution of KL divergence (the test statistic), $\hat{\text{Dist}}_t$.

Significance testing: To test if a significant difference exists between $\hat{D}_{1,t}$ and $\hat{D}_{2,t}$, calculate the p-value by calculating the number of times the test statistic from the permuted sample is equal to or greater than the original test statistic $\text{Dist}_t$, in the empirical distribution $\hat{\text{Dist}}_t$. If a small p-value is obtained, reject the null hypothesis in favor of alternative hypothesis. This is shown in Eq. (5).

$$p_{perm} = \frac{\#\hat{\text{Dist}}_t > \text{Dist}_t}{\# \text{permutations}} \quad (5)$$

where $\hat{\text{Dist}}_t$ is the empirical distribution of the test statistic at the t-th time interval. We reject the null hypothesis that no changes have occurred at a significance level of $\alpha = 0.01$.

Changes in Activity Curves

We now extend the technique of detecting significant changes between activity distributions to quantify the difference in activity routine observed from two separate aggregation windows, $W_1$ and $W_2$, each of size x days. To do this, PCAR counts the total number of significant differences between the individual activity distributions within window $W_1$ and the distributions within window $W_2$ to output a change score that quantifies the significant changes observed among the activity curves. FIG. 7 demonstrates the three main steps involved in detecting changes in an activity curve using the permutation-based method.

PCAR calculates a sum, S, over changes that are detected between activity curve distributions for each individual time interval. In order to identify the time intervals at which changes in the activity distributions comprising the aggregated activity curves are deemed significant, PCAR performs the following steps:

Permutation: Calculate the empirical distributions of the test statistic (KL divergence) by permuting and comparing the individual activity distributions within the two aggregation windows $W_1$ and $W_2$ at each time interval using the method summarized in Algorithm 5.

Alignment: Calculate the two aggregated activity curves $C_1$ and $C_2$ using the activity distributions aggregated for each time interval over windows $W_1$ and $W_2$. Align curves $C_1$ and $C_2$ using one of the alignment techniques described in the previous section to generate the alignment vector $\Gamma=(u, v)$.

Calculate the test statistic: For each alignment pair $u, v)=\Gamma$, calculate the test statistic $Dist_{u,v}$ between the aggregated activity distribution at time interval u of activity curve $C_1$ and the aggregated activity distribution at time interval v of $C_2$.

Significance testing: To test if there is a significant change between activity distributions at time intervals u and v, calculate the p-value based on the number of times the test statistic from the permuted sample is equal to or greater than the original test statistic. The steps are summarized in Algorithm 6.

Algorithm 5
ALGORITHM 5 EmpiricalDistribution ($\Sigma_1, \Sigma_2 \cdot N_p$)

1: // Build empirical distribution of the test statistic.
2: $\Sigma_1, \Sigma_2$ - two sets of activity curves
3: $N_p$ - number of permutations
4: Initialize $Dist_t$ as $N_p \times$ m matrix;
   // m is # activity distributions in the activity curves
5: initialize i = 0;
6: while i < $N_p$ do:
7:    Shuffle the activity curves;
8:    Generate aggregated activity curves $C^{\Sigma_1}$ and $C^{\Sigma_2}$ by aggregating the distributions in $\Sigma_1, \Sigma_2$;
9:    Using the time interval-based alignment technique, align the two aggregated activity curves to obtain an alignment vector $\Gamma$;
10:    for all alignment pairs (u, u) in $\Gamma$ do:
11:       Find a distance $SD_{KL} (D_{1,u} \| D_{2,u})$ between uth activity distributions in two activity curves;
12:       Insert $\widehat{SD}_{KL} (D_{1,u} \| D_{2,u})$ to empirical distribution $\widehat{Dist}$ at location [i, u];
13:    end for;
14:    i = i+1;
15: end while;
16: return $\widehat{Dist}$ Algorithm 6
ALGORITHM 6 PCAR ($\Sigma_1, \Sigma_2 \cdot N_p$)

1: $\Sigma_1, \Sigma_2$ - two sets of activity curves
2: // Return a change score S
3: $C_1$ – AggregateActivityCurves ($\Sigma_1$)
4: $C_2$ – AggregateActivityCurves ($\Sigma_2$)
5: $\Gamma$ - AlignCurves ($C_1, C_2$)
6: for all alignment pairs (u, v) in $\Gamma$ do:
7:    Calculate $SD_{KL} (D_{1,u} \| D_{2,v})$ between activity distribution $D_{1,u} \in C_1$ and $D_{2,v} \in C_2$;
8:    Perform significance testing of estimated distance by querying $\widehat{Dist}$;
9:    if change is significant:

Algorithm 6
ALGORITHM 6 PCAR ($\Sigma_1, \Sigma_2 \cdot N_p$)

10:       S = S + 1;
11:    end for;
12:    return S;

We note that we compare at least m activity distributions during this process where m is the number of aggregated activity distributions in an activity curve. To control the False Discovery Rate (FDR) at level $\alpha^*(\alpha^*=0.01)$, we apply the Benjamini-Hochberg (BH) method [65]. The BH method first orders the p-values, $p_1, p_2, \ldots, p_k, \ldots, p_m$, in ascending order and for a given value of $\alpha^*$, the BH method finds the largest k such that $$p(k) \leq k \times \frac{\alpha^*}{m}.$$

The BH algorithm rejects the null hypothesis corresponding to $p_i$ if i≤k. If a significant change is detected between aligned activity distributions, PCAR increments its change score, S, by one. PCAR generates two different change scores based on the alignment techniques that are employed: either the same index alignment or the DTW-based alignment.

Example Computing System

Figure 8:
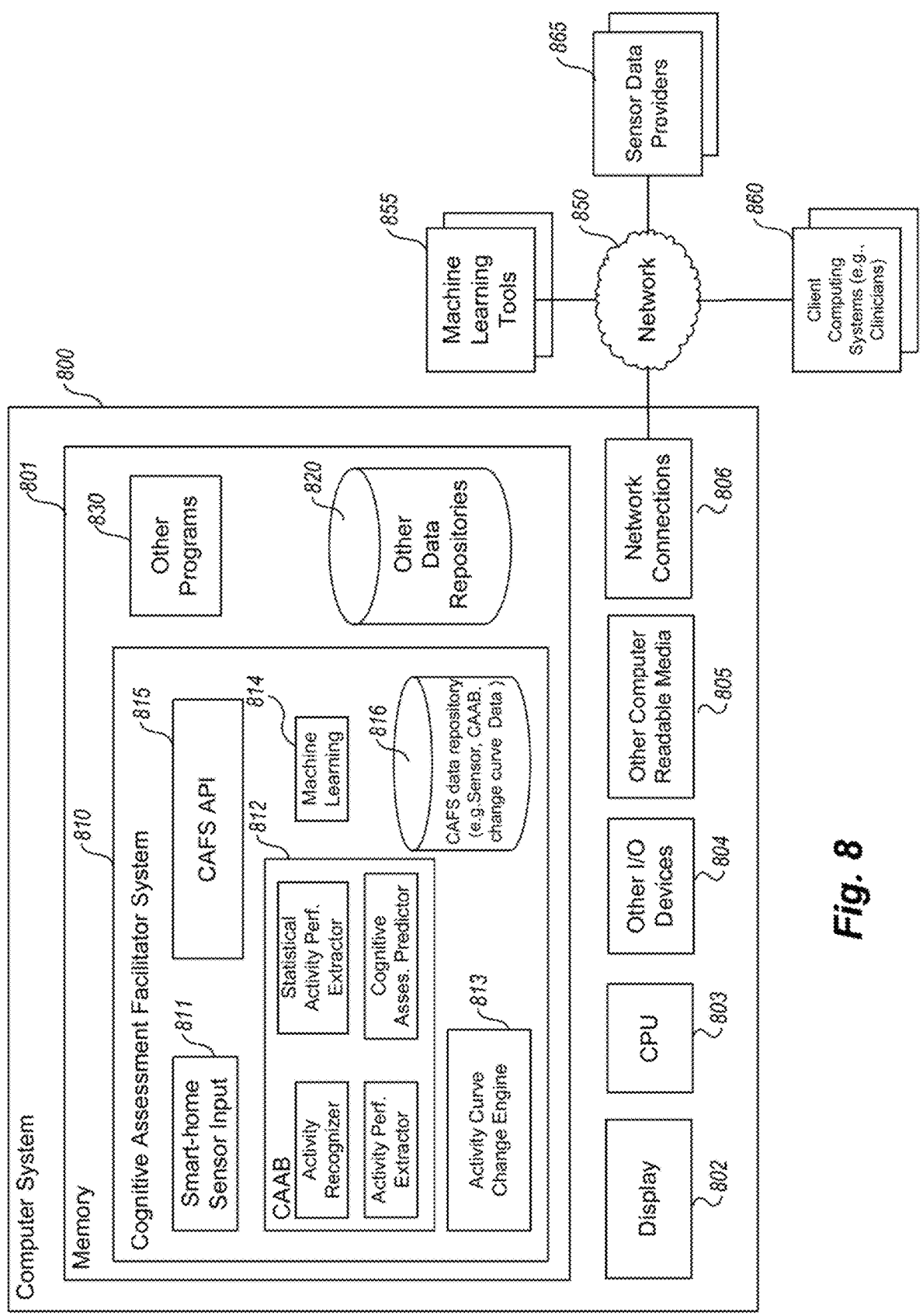
FIG. 8 is an example block diagram of an example computing system that may be used to practice embodiments of an example Cognitive Assessment Facilitator System.

FIG. 8 is an example block diagram of an example computing system that may be used to practice embodiments of a Cognitive Assessment Facilitator System described herein. Note that one or more general purpose virtual or physical computing systems suitably instructed or a special purpose computing system may be used to implement an OAFS. Further, the OAFS may be implemented in software, hardware, firmware, or in some combination to achieve the capabilities described herein.

The computing system 800 may comprise one or more server and/or client computing systems and may span distributed locations. In addition, each block shown may represent one or more such blocks as appropriate to a specific embodiment or may be combined with other blocks. Moreover, the various blocks of the Cognitive Assessment Facilitator System 810 may physically reside on one or more machines, which use standard (e.g., TCP/IP) or proprietary interprocess communication mechanisms to communicate with each other.

In the embodiment shown, computer system 800 comprises a computer memory ("memory") 801, a display 802, one or more Central Processing Units ("CPU") 803, Input/Output devices 804 (e.g., keyboard, mouse, CRT or LCD display, etc.), other computer-readable media 805, and one or more network connections 806. The OAFS 810 is shown residing in memory 801. In other embodiments, some portion of the contents, some of, or all of the components of the OAFS 810 may be stored on and/or transmitted over the other computer-readable media 805. The components of the Cognitive Assessment Facilitator System 810 preferably execute on one or more CPUs 803 and manage the generation and use of predictive cognitive assessments and functional assessments, as described herein. Other code or programs 830 and potentially other data repositories, such as data repository 806, also reside in the memory 801, and preferably execute on one or more CPUs 803. Of note, one or more of the components in FIG. 8 may not be present in any specific implementation. For example, some embodiments embedded in other software may not provide means for user input or display.

In a typical embodiment, the OAFS 810 includes one or more smart-home sensor input logic 811, one or more CAAB logic components 812, and one or more activity curve change logic components (or engines) 813, and one or more machine learning engines 814 that operate as described herein. In at least some embodiments, the machine learning logic is provided external to the OAFS such as machine learning tools 855 and is available, potentially, over one or more networks 850. Other and/or different modules may be implemented. In addition, the OAFS may interact via a network 850 with application or client code 860 that uses results computed by the OAFS 810, and/or one or more third-party information provider systems 865, such as smart home sensor data providers. Also, of note, the OAFS data repository 816, which may include sensor CAAB, and change curve data, may be provided external to the OAFS as well, for example in a knowledge base accessible over one or more networks 850.

In an example embodiment, components/modules of the OAFS 810 are implemented using standard programming techniques. For example, the OAFS 810 may be implemented as a "native" executable running on the CPU 103, along with one or more static or dynamic libraries. In other embodiments, the OAFS 810 may be implemented as instructions processed by a virtual machine. In general, a range of programming languages known in the art may be employed for implementing such example embodiments, including representative implementations of various programming language paradigms, including but not limited to, object-oriented, functional, procedural, scripting, and declarative.

The embodiments described above may also use well-known or proprietary, synchronous or asynchronous client-server computing techniques. Also, the various components may be implemented using more monolithic programming techniques, for example, as an executable running on a single CPU computer system, or alternatively decomposed using a variety of structuring techniques known in the art, including but not limited to, multiprogramming, multithreading, client-server, or peer-to-peer, running on one or more computer systems each having one or more CPUs. Some embodiments may execute concurrently and asynchronously and communicate using message passing techniques. Equivalent synchronous embodiments are also supported.

In addition, programming interfaces to the data stored as part of the OAFS 810 (e.g., in the data repositories 816) can be available by standard mechanisms such as through C, C++, C#, and Java APIs; libraries for accessing files, databases, or other data repositories; through scripting languages such as XML; or through Web servers, FTP servers, or other types of servers providing access to stored data. The data repositories may be implemented as one or more database systems, file systems, or any other technique for storing such information, or any combination of the above, including implementations using distributed computing techniques.

Also the example OAFS 810 may be implemented in a distributed environment comprising multiple, even heterogeneous, computer systems and networks. Different configurations and locations of programs and data are contemplated for use with techniques of described herein. In addition, the [server and/or client] may be physical or virtual computing systems and may reside on the same physical system. Also, one or more of the modules may themselves be distributed, pooled or otherwise grouped, such as for load balancing, reliability or security reasons. A variety of distributed computing techniques are appropriate for implementing the components of the illustrated embodiments in a distributed manner including but not limited to TCP/IP sockets, RPC, RMI, HTTP, Web Services (XML-RPC, JAX-RPC, SOAP, etc.) and the like. Other variations are possible. Also, other functionality could be provided by each component/module, or existing functionality could be distributed amongst the components/modules in different ways, yet still achieve the functions of an OAFS.

Furthermore, in some embodiments, some or all of the components of the OAFS 810 may be implemented or provided in other manners, such as at least partially in firmware and/or hardware, including, but not limited to one or more application-specific integrated circuits (ASICs), standard integrated circuits, controllers executing appropriate instructions, and including microcontrollers and/or embedded controllers, field-programmable gate arrays (FPGAs), complex programmable logic devices (CPLDs), and the like. Some or all of the system components and/or data structures may also be stored as contents (e.g., as executable or other machine-readable software instructions or structured data) on a computer-readable medium (e.g., a hard disk; memory; network; other computer-readable medium; or other portable media article to be read by an appropriate drive or via an appropriate connection, such as a DVD or flash memory device) to enable the computer-readable medium to execute or otherwise use or provide the contents to perform at least some of the described techniques. Some or all of the components and/or data structures may be stored on tangible, non-transitory storage mediums. Some or all of the system components and data structures may also be stored as data signals (e.g., by being encoded as part of a carrier wave or included as part of an analog or digital propagated signal) on a variety of computer-readable transmission mediums, which are then transmitted, including across wireless-based and wired/cable-based mediums, and may take a variety of forms (e.g., as part of a single or multiplexed analog signal, or as multiple discrete digital packets or frames. Such computer program products may also take other forms in other embodiments. Accordingly, embodiments of this disclosure may be practiced with other computer system configurations.

All of the above U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 62/150,794, entitled "MODELING PATTERNS OF ACTIVITIES USING ACTIVITY CURVES," filed Apr. 21, 2015, are incorporated herein by reference in its entirety.

From the foregoing it will be appreciated that, although specific embodiments have been described herein for purposes of illustration, various modifications may be made without deviating from the spirit and scope of the invention. For example, the methods and systems for performing facilitating cognitive assessment discussed herein are applicable to other architectures other than a client-server architecture. Also, the methods and systems discussed herein are applicable to differing protocols, communication media (optical, wireless, cable, etc.) and devices (such as wireless handsets, electronic organizers, personal digital assistants, portable email machines, game machines, pagers, navigation devices such as GPS receivers, embedded systems, etc.).

REFERENCES

[1] M. Schmitter-Edgecombe, C. Parsey, and R. Lamb, "Development and sychometric properties of the instrumental activities of daily living: compensation cale." Archives of clinical neuropsychology: Journal of the National Academy of Neuropsychologists, vol. 29, no. 8, pp. 776-92, December 2014.

[2] Y. Ouchi, K. Akanuma, M. Meguro, M. Kasai, H. Ishii, and K. Meguro, "Impaired instrumental activities of daily living affect conversion from mild cognitive impairment to dementia: the Osaki-Tajiri Project." Psychogeriatrics, vol. 12, no. 1, pp. 34-42, March 2012.

[3] N. Chaytor, M. Schmitter-Edgecombe, and R. Burr, "Improving the ecological validity of executive functioning assessment." Archives of clinical neuropsychology, vol. 21, no. 3, pp. 217-27, April 2006.

[4] P. Paavilainen, I. Korhonen, J. Lötjönen, L. Cluitmans, M. Jylhä, A. Sârelâ, and M. Partinen, "Circadian activity rhythm in demented and non-demented nursing-home residents measured by telemetric actigraphy." Journal of sleep research, vol. 14, no. 1, pp. 61-68, March 2005.

[5] P. Paavilainen, I. Korhonen, and M. Partinen, "Telemetric activity monitoring as an indicator of long-term changes in health and well-being of older people." Gerontechnology, vol. 4, no. 2, pp. 77-85, 2005.

[6] S. Robben, M. Pol, and B. Kröse, "Longitudinal ambient sensor monitoring for functional health assessments." in Proceedings of the 2014 ACM International Joint Conference on Pervasive and Ubiquitous Computing Adjunct Publication—UbiComp '14 Adjunct. New York, N.Y., USA: ACM Press, September 2014, pp. 1209-1216.

[7] T. Suzuki and S. Murase, "Influence of outdoor activity and indoor activity on cognition decline: use of an infrared sensor to measure activity." Telemedicine journal and e-health: journal of the American Telemedicine Association, vol. 16, no. 6, pp. 686-690, 2010.

[8] H. H. Dodge, N. C. Mattek, D. Austin, T. L. Hayes, and J. A. Kaye, "Inhome walking speeds and variability trajectories associated with mild cognitive impairment." Neurology, vol. 78, no. 24, pp. 1946-1952, June 2012.

[9] G. LeBellego, N. Noury, G. Virone, M. Mousseau, and J. Demongeot, "A Model for the Measurement of Patient Activity in a Hospital Suite." IEEE Transactions on Information Technology in Biomedicine, vol. 10, no. 1, pp. 92-99, January 2006.

[10] C. Galambos, M. Skubic, S. Wang, and M. Rantz, "Management of dementia and depression utilizing in-home passive sensor data." Gerontechnology, vol. 11, no. 3, pp. 457-468, 2013.

[11] Wang, M. Skubic, and Y. Zhu, "Activity density map visualization and dissimilarity comparison for eldercare monitoring." IEEE Transactions on Information Technology in Biomedicine, vol. 16, no. 4, pp. 607-614, July 2012.

[12] C. Chen and P. Dawadi, "CASASviz: Web-based visualization of behavior patterns in smart environments." in 2011 IEEE International Conference on Pervasive Computing and Communications Workshops (PERCOM Workshops). IEEE, March 2011, pp. 301-303.

[13] M. Kanis, S. Robben, J. Hagen, A. Bimmerman, N. Wagelaar, and B. Kröse, "Sensor Monitoring in the Home: Giving Voice to Elderly People." in Pervasive Computing Technologies for Healthcare (PervasiveHealth), 2013 7th International Conference on, Venice, Italy, 2013, pp. 97-100.

[14] N. Noury, M. Berenguer, H. Teyssier, M.-J. Bouzid, and M. Giordani, "Building an index of activity of inhabitants from their activity on the residential electrical power line." IEEE transactions on information technology in biomedicine: a publication of the IEEE Engineering in Medicine and Biology Society, vol. 15, no. 5, pp. 758-66, September 2011.

[15] P. Dawadi, D. Cook, and M. Schmitter-Edgecombe, "Automated cognitive health assessment using smart home smart monitoring of complex tasks." IEEE Transactions on Systems, Man, and Cybernetics: Systems, vol. 43, no. 6, pp. 1302-1313, 2013.

[16] D. J. Cook and N. C. Krishnan, Activity Learning: Discovering, Recognizing, and Predicting Human Behavior from Sensor Data. New York: Wiley, 2015.

[17] D. J. Cook, A. S. Crandall, B. L. Thomas, and N. C. Krishnan, "CASAS: A Smart Home in a Box." Computer, vol. 46, no. 7, pp. 62-69, July 2013.

[18] A. P. Association, Diagnostic and statistical manual of mental disorders: DSM-IV-TR., 4th ed., ser. Diagnostic and statistical manual of mental disorders. Washington, D.C.: American Psychiatric Association, 2000, vol. 4th, no. 2.

[19] M. S. Albert, S. T. DeKosky, D. Dickson, B. Dubois, H. H. Feldman, N. C. Fox, A. Gamst, D. M. Holtzman, W. J. Jagust, R. C. Petersen, P. J. Snyder, M. C. Carrillo, B. Thies, and C. H. Phelps, "The diagnosis of mild cognitive impairment due to Alzheimer's disease: recommendations from the National Institute on Aging-Alzheimer's Association workgroups on diagnostic guidelines for Alzheimer's disease." Alzheimer's & dementia: the journal of the Alzheimer's Association, vol. 7, no. 3, pp. 270-9, May 2011.

[20] C. Randolph, Repeatable Battery for the Assessment of Neuropsychological Status Update. San Antonio, Tex.: Psychological Corporation., 1998.

[21] D. Podsiadlo and S. Richardson, "The timed "Up & Go": a test of basic functional mobility for frail elderly persons." Journal of the American Geriatrics Society, vol. 39, no. 2, pp. 142-148, 1991.

[22] N. C. Krishnan and D. J. Cook, "Activity Recognition on Streaming Sensor Data." Pervasive and mobile computing, vol. 10, pp. 138-154, February 2014.

[23] M. M. Ohayon, M. A. Carskadon, C. Guilleminault, and M. V. Vitiello, "Meta-analysis of quantitative sleep parameters from childhood to old age in healthy individuals: developing normative sleep values across the human lifespan." Sleep, vol. 27, no. 7, pp. 1255-1273, November 2004.

[24] M. Jelicic, H. Bosma, R. W. H. M. Ponds, M. P. J. Van Boxtel, P. J. Houx, and J. Jolles, "Subjective sleep problems in later life as predictors of cognitive decline. Report from the Maastricht Ageing Study (MAAS)." International journal of geriatric psychiatry, vol. 17, no. 1, pp. 73-77, January 2002.

[25] C. L. Deschenes and S. M. McCurry, "Current treatments for sleep disturbances in individuals with dementia." Current psychiatry reports, vol. 11, no. 1, pp. 20-26, February 2009.

[26] J. L. Martin, L. Fiorentino, S. Jouldjian, K. R. Josephson, and C. A. Alessi, "Sleep quality in residents of assisted living facilities: effect on quality of life, functional status, and depression." Journal of the American Geriatrics Society, vol. 58, no. 5, pp. 829-36, May 2010.

[27] T. Hope, J. Keene, K. Gedling, C. G. Fairburn, and R. Jacoby, "Predictors of institutionalization for people with dementia living at home with a carer." International journal of geriatric psychiatry, vol. 13, no. 10, pp. 682-690, October 1998.

[28] E. Scherder, L. Eggermont, D. Swaab, M. van Heuvelen, Y. Kamsma, M. de Greef, R. van Wijck, and T. Mulder, "Gait in ageing and associated dementias; its relationship with cognition." Neuroscience and biobehavioral reviews, vol. 31, no. 4, pp. 485-97, January 2007.

[29] C. McAlister and M. Schmitter-Edgecombe, "Naturalistic assessment of executive function and everyday multitasking in healthy older adults." Neuropsychology, development, and cognition. Section B, Aging, neuropsychology and cognition, vol. 20, no. 6, pp. 735-56, January 2013.

[30] M. Schmitter-Edgecombe, C. Parsey, and D. J. Cook, "Cognitive correlates of functional performance in older adults: comparison of self report, direct observation, and performance-based measures." Journal of the International Neuropsychological Society JINS, vol. 17, no. 5, pp. 853-864, 2011.

[31] S. T. Farias, D. Mungas, B. R. Reed, D. Harvey, D. Cahn-Weiner, and C. Decarli, "MCI is associated with deficits in everyday functioning." Alzheimer disease and associated disorders, vol. 20, no. 4, pp. 217-223, 2006.

[32] M. Schmitter-Edgecombe and C. M. Parsey, "Assessment of functional change and cognitive correlates in the progression from healthy cognitive aging to dementia." Neuropsychology, vol. 28, no. 6, pp. 881-893, November 2014.

[33] V. Dakos, S. R. Carpenter, W. A. Brock, A. M. Ellison, V. Guttal, A. R. Ives, S. Kéfi, V. Livina, D. A. Seekell, E. H. van Nes, and M. Scheffer, "Methods for detecting early warnings of critical transitions in time series illustrated using simulated ecological data." PloS one, vol. 7, no. 7, p. e41010, January 2012.

[34] H. Hotelling, "The Generalization of Student's Ratio." The Annals of Mathematical Statistics, vol. 2, no. 3, pp. 360-378, August 1931.

[35] I. H. Witten and E. Frank, Data Mining: Practical Machine Learning Tools and Techniques, Second Edition (Morgan Kaufmann Series in Data Management Systems). Morgan Kaufmann Publishers Inc., June 2005.

[36] K. Pérès, V. Chrysostome, C. Fabrigoule, J. M. Orgogozo, J. F. Dartigues, and P. Barberger-Gateau, "Restriction in complex activities of daily living in MCI: impact on outcome." Neurology, vol. 67, no. 3, pp. 461-466, August 2006.

[37] "Stopping elderly accidents, deaths & injuries. Center for Disease Control and Prevention." [Online]. Available: http://www.cdc.gov/homeandrecreationalsafety/pdf/steadi/timed up and go test.pdf.

[38] M. Ojala and G. C. Garriga, "Permutation Tests for Studying Classifier Performance," The Journal of Machine Learning Research, vol. 11, pp. 1833-1863, March 2010.

[39] T. Huynh, M. Fritz, B. Schiele, Discovery of activity patterns using topic models, in: Proceedings of the 10th International Conference on Ubiquitous Computing, UbiComp '08, ACM Press, New York, N.Y., USA, 2008, pp. 10-19.

[40] F.-T. Sun, H.-T. Cheng, C. Kuo, M. Griss, Nonparametric discovery of human routines from sensor data, in: 2014 IEEE International Conference on Pervasive Computing and Communications, PerCom, IEEE, 2014, pp. 11-19.

[41] K. Farrahi, D. Gatica-Perez, Discovering routines from large-scale human locations using probabilistic topic models, ACM Trans. Intell. Syst. Technol. 2 (1) (2011) 1-27.

[42] K. Farrahi, D. Gatica-Perez, What did you do today? discovering daily routines from large-scale mobile data, in: Proceeding of the 16th ACM International Conference on Multimedia, MM '08, ACM Press, New York, N.Y., USA, 2008, pp. 849-852.

[43] J. Zheng, S. Liu, L. M. Ni, Effective routine behavior pattern discovery from sparse mobile phone data via collaborative filtering, in: 2013 IEEE International Conference on Pervasive Computing and Communications, PerCom, IEEE, 2013, pp. 29-37.

[44] C. Galambos, M. Skubic, S. Wang, M. Rantz, Management of dementia and depression utilizing in-home passive sensor data, Gerontechnology 11 (3) (2013) 457-468.

[45] S. Wang, M. Skubic, Y. Zhu, Activity density map visualization and dissimilarity comparison for eldercare monitoring, IEEE Trans. Inf. Technol. Biomed. 16 (4) (2012) 607-614.

[46] C. Chen, P. Dawadi, CASASviz: Web-based visualization of behavior patterns in smart environments, in: 2011 IEEE International Conference on Pervasive Computing and Communications Workshops, PERCOM Workshops, IEEE, 2011, pp. 301-303.

[47] M. Kanis, S. Robben, J. Hagen, A. Bimmerman, N. Wagelaar, B. Kröse, Sensor monitoring in the home: Giving voice to elderly people, in: 2013 $7^{th}$ International Conference on Pervasive Computing Technologies for Healthcare, PervasiveHealth, Venice, Italy, 2013, pp. 97-100.

[48] D. J. Sheskin, Handbook of Parametric and Nonparametric Statistical Procedures, third ed., Chapman & Hall/CRC, New York, 2007.

[49] A. Gretton, K. M. Borgwardt, M. J. Rasch, B. Schölkopf, A. Smola, A kernel two-sample test, J. Mach. Learn. Res. 13 (1) (2012) 723-773.

[50] B. K. Sriperumbudur, A. Gretton, F. K., B. Schölkopf, The effect of kernel choice of RKHS based statistical tests, in: Representations and Inference on Probability Distributions Workshop, NIPS, Vancouver, B. C, Canada, 2007.

[51] M. Sugiyama, T. Suzuki, Y. Itoh, T. Kanamori, M. Kimura, Least-squares two-sample test, Neural Netw. 24 (7) (2011) 735-751.

[52] P. Rashidi, D. Cook, Keeping the resident in the loop: Adapting the smart home to the user, IEEE Trans. Syst. Man Cybern. A 39 (5) (2009) 949-959.

[53] P. Rashidi, D. J. Cook, Mining sensor streams for discovering human activity patterns over time, in: 2010 IEEE International Conference on Data Mining, IEEE, 2010, pp. 431-440.

[54] P. Paavilainen, I. Korhonen, J. Lötjönen, L. Cluitmans, M. Jylhä, A. Särelä, M. Partinen, Circadian activity rhythm in demented and non-demented nursing-home residents measured by telemetric actigraphy, J. Sleep Res. 14 (1) (2005) 61-68.

[55] S. Robben, G. Englebienne, M. Pol, B. Kröse, How is grandma doing? predicting functional health status from binary ambient sensor data, in: 2012 AAAI Fall Symposium Series, Washington D.C., 2012, pp. 26-31.

[56] S. Robben, M. Boot, M. Kanis, B. Kr, Identifying and visualizing relevant deviations in longitudinal sensor patterns for care professionals, in: $7^{th}$ International Conference on Pervasive Computing Technologies for Healthcare, PervasiveHealth, Venice, Italy, 2013, pp. 416-419.

[57] S. Robben, M. Pol, B. Kröse, Longitudinal ambient sensor monitoring for functional health assessments, in: Proceedings of the 2014 ACM International Joint Conference on Pervasive and Ubiquitous Computing Adjunct Publication, UbiComp '14 Adjunct, ACM Press, New York, N.Y., USA, 2014, pp. 1209-1216.

[58] A. G. Fisher, B. Jones, Assessment of Motor and Process Skills. User Manual, seventh ed., Three Star Press, Fort Collins, Colo., 2012.

[59] T. L. Hayes, F. Abendroth, A. Adami, M. Pavel, T. A. Zitzelberger, J. A. Kaye, Unobtrusive assessment of activity patterns associated with mild cognitive impairment, Alzheimer's Dement. 4 (6) (2008) 395-405.

[60] P. Dawadi, D. Cook, M. Schmitter-Edgecombe, Automated cognitive health assessment using smart home smart monitoring of complex tasks, IEEE Trans. Syst. Sci. Cybern. 43 (6) (2013) 1302-1313.

[61] P. Dawadi, D. J. Cook, M. Schmitter-Edgecombe, C. Parsey, Automated assessment of cognitive health using smart home technologies, Technol. Health Care 21 (4) (2013) 323-343.

[62] M. R. Hodges, N. L. Kirsch, M. W. Newman, M. E. Pollack, Automatic assessment of cognitive impairment through electronic observation of object usage, in: P. Floréen, A. Krüger, M. Spasojevic (Eds.), Proc. International Conference on Pervasive Computing, in: Lecture Notes in Computer Science, vol. 6030, Springer Berlin Heidelberg, Berlin, Heidelberg, 2010, pp. 192-209.

[63] D. Riboni, C. Bettini, G. Civitarese, Z. H. Janjua, R. Helaoui, Finegrained recognition of abnormal behaviors for early detection of mild cognitive impairment, Proc. PerCom (2015) 149-154.

[64] B. Efron, R. Tibshirani, An Introduction to the Bootstrap, Chapman & Hall, New York, 1994.

[65] Y. Benjamini, Y. Hochberg, Controlling the false discovery rate: A practical and powerful approach to multiple testing, J. R. Stat. Soc. Ser. B Stat. Methodol. 57 (1) (1995) 289-300.

[66] T. Luck, M. Luppa, M. C. Angermeyer, A. Villringer, H.-H. König, S. G. Riedel-Heller, Impact of impairment in instrumental activities of daily living and mild cognitive impairment on time to incident dementia: results of the Leipzig longitudinal study of the aged, Psychol. Med. 41 (5) (2011) 1087-1097.

[67] D. Marson, K. Hebert, Geriatric neuropsychology assessment and intervention, in: Geriatric Neuropsychology Assessment and Intervention, The Guilford Press, New York, USA, 2006, pp. 158-189. Ch. Functional.

[68] Y. Ouchi, K. Akanuma, M. Meguro, M. Kasai, H. Ishii, K. Meguro,
Impaired instrumental activities of daily living affect conversion from mild cognitive impairment to dementia: the Osaki-Tajiri project, Psychogeriatrics 12 (1) (2012) 34-42.

[69] D. J. Cook, N. C. Krishnan, P. Rashidi, Activity discovery and activity recognition: a new partnership, IEEE Trans. Syst. Man Cybern. B 43 (3) (2013) 820-828.

[70] N. C. Krishnan, D. J. Cook, Activity recognition on streaming sensor data, pervasive Mobile Comput. 10 (2014) 138-154.

[71] D. J. Cook, A. S. Crandall, B. L. Thomas, N. C. Krishnan, CASAS: A smart home in a box, Computer 46 (7) (2013) 62-69.

[72] A. P. Association, Diagnostic and Statistical Manual of Mental Disorders: DSM-IV-TR, fourth ed., in: Diagnostic and Statistical Manual of Mental Disorders, vol. 4, American Psychiatric Association, Washington, D C, 2000.

[73] M. S. Albert, S. T. DeKosky, D. Dickson, B. Dubois, H. H. Feldman, N. C. Fox, A. Gamst, D. M. Holtzman, W. J. Jagust, R. C. Petersen, P. J. Snyder, M. C. Carrillo, B. Thies, C. H. Phelps, The diagnosis of mild cognitive impairment due to Alzheimer's disease: recommendations from the National Institute on Aging-Alzheimer's Association workgroups on diagnostic guidelines for Alzheimer's disease, Alzheimer's Dement. 7 (3) (2011) 270-279.

[74] C. L. Deschenes, S. M. McCurry, Current treatments for sleep disturbances in individuals with dementia, Curr. Psychiatry Rep. 11 (1) (2009) 20-26.

[75] M. Jelicic, H. Bosma, R. W. H. M. Ponds, M. P. J. Van Boxtel, P. J. Houx, J. Jolles, Subjective sleep problems in later life as predictors of cognitive decline. Report from the Maastricht ageing study (MAAS), Int. J. Geriatr. Psychiatry 17 (1) (2002) 73-77.

[76] T. Schmutte, S. Harris, R. Levin, R. Zweig, M. Katz, R. Lipton, The relation between cognitive functioning and self-reported sleep complaints in nondemented older adults: results from the Bronx aging study, Behav. Sleep Med. 5 (1) (2007) 39-56.

[77] H. C. Driscoll, L. Serody, S. Patrick, J. Maurer, S. Bensasi, P. R. Houck, S. Mazumdar, E. A. Nofzinger, B. Bell, R. D. Nebes, M. D. Miller, C. F. Reynolds, Sleeping well, aging well: a descriptive and cross-sectional study of sleep in "successful agers" 75 and older, Am. J. Geriatr. Psychiatry 16 (1) (2008) 74-82.

[78] J. L. Martin, L. Fiorentino, S. Jouldjian, K. R. Josephson, C. A. Alessi, Sleep quality in residents of assisted living facilities: effect on quality of life, functional status, and depression, J. Am. Geriatr. Soc. 58 (5) (2010) 829-836.

[79] E. Eeles, Sleep and its management in dementia, Rev. Clin. Geront. 16 (01) (2007) 59-70.

[80] M. Schmitter-Edgecombe, C. Parsey, D. J. Cook, Cognitive correlates of functional performance in older adults: comparison of self-report, direct observation, and performance-based measures, J. Int. Neuropsychol. Soc. 17 (5) (2011) 853-864.

[81] S. Artero, J. Touchon, K. Ritchie, Disability and mild cognitive impairment: a longitudinal populationbased study, Int. J. Geriatr. Psychiatry 16 (11) (2001) 1092-1097.

[82] S. T. Farias, D. Mungas, B. R. Reed, D. Harvey, D. Cahn-Weiner, C. Decarli, MCI is associated with deficits in everyday functioning, Alzheimer Dis. Assoc. Disord. 20 (4) (2006) 217-223.

[83] H. Pedrosa, A. De Sa, M. Guerreiro, J. Maroco, M. R. Simoes, D. Galasko, A. de Mendonca, Functional evaluation distinguishes MCI patients from healthy elderly people—the ADCS/MCI/ADL scale, J. Nutr. Health Aging 14 (8) (2010) 703-709.

[84] M. Schmitter-Edgecombe, C. M. Parsey, Assessment of functional change and cognitive correlates in the progression from healthy cognitive aging to dementia, Neuropsychology 28 (6) (2014) 881-893.

[85] A. L. Gross, G. W. Rebok, F. W. Unverzagt, S. L. Willis, J. Brandt, Cognitive predictors of everyday functioning in older adults: Results from the ACTIVE cognitive intervention trial, J. Gerontol. B Psychol. Sci. Soc. Sci. 66 (5) (2011) 557-566.

[86] M. Schmitter-Edgecombe, C. McAlister, A. Weakley, Naturalistic assessment of everyday functioning in individuals with mild cognitive impairment: the day-out task, Neuropsychology 26 (5) (2012) 631-641.

[87] D. Podsiadlo, S. Richardson, The timed "Up & Go": a test of basic functional mobility for frail elderly persons, J. Am. Geriatr. Soc. 39 (2) (1991) 142-148.

[88] C. Randolph, Repeatable Battery for the Assessment of Neuropsychological Status Update, Psychological Corporation, San Antonio, Tex., 1998.

APPENDIX A—EXPERIMENTAL VALIDATION OF CAAB

CASAS Smart Home Test Bed

The CAAB approach was tested in CASAS smart homes (see http://casas.wsu.edu), with test single residence apartments [17] with smart home sensors laid out as in FIG. 1. Each apartment included at least one bedroom, a kitchen, a dining area, and at least one bathroom. The homes were equipped with combination motion/light sensors on the ceilings and combination door/temperature sensors on cabinets and doors. These sensors in the smart home test beds unobtrusively and continuously monitored the daily activities of its residents. The CASAS middleware collected these sensor events and stored the data on a database server.

Dataset

The CASAS middleware collected sensor data while monitoring the daily behavior of 18 smart home senior residents for approximately 2 years. We used the AR activity recognition algorithm to automatically label the sensor events with the corresponding activity labels. By running CAAB on the (activity-labeled) sensor data, the activity performance features were computed and statistical activity features were extracted from them. CAAB then created a training set by combining the statistical activity features and the corresponding clinical assessment scores (RBANS and TUG) to train a machine learning algorithm.

Residents

Residents included 18 community-dwelling seniors (5 females, 13 males) from a retirement community. All participants were 73 years of age or older (M=84:71, SD=5:24, range 73-92) and have a mean education level of 17:52 years (SD=2:15, range 12-20). At baseline 51, participants were classified as either cognitively healthy (N=7), at risk for cognitive difficulties (N=6) or experiencing cognitively difficulties (N=5). One participant in the cognitively compromised group met the Diagnostic and Statistical Manual of Mental Disorders (DSM-IV-TR) criteria for dementia [18], while the other four individuals met criteria for mild cognitive impairment (MCI) as outlined by the National Institute on Aging-Alzheimer's Association workgroup [19]. Participants in the risk group had data suggestive of lowered performance on one or more cognitive tests (relative to an estimate of premorbid abilities), along with sensory and/or mobility difficulties.

Clinical Tests

Figure 9:
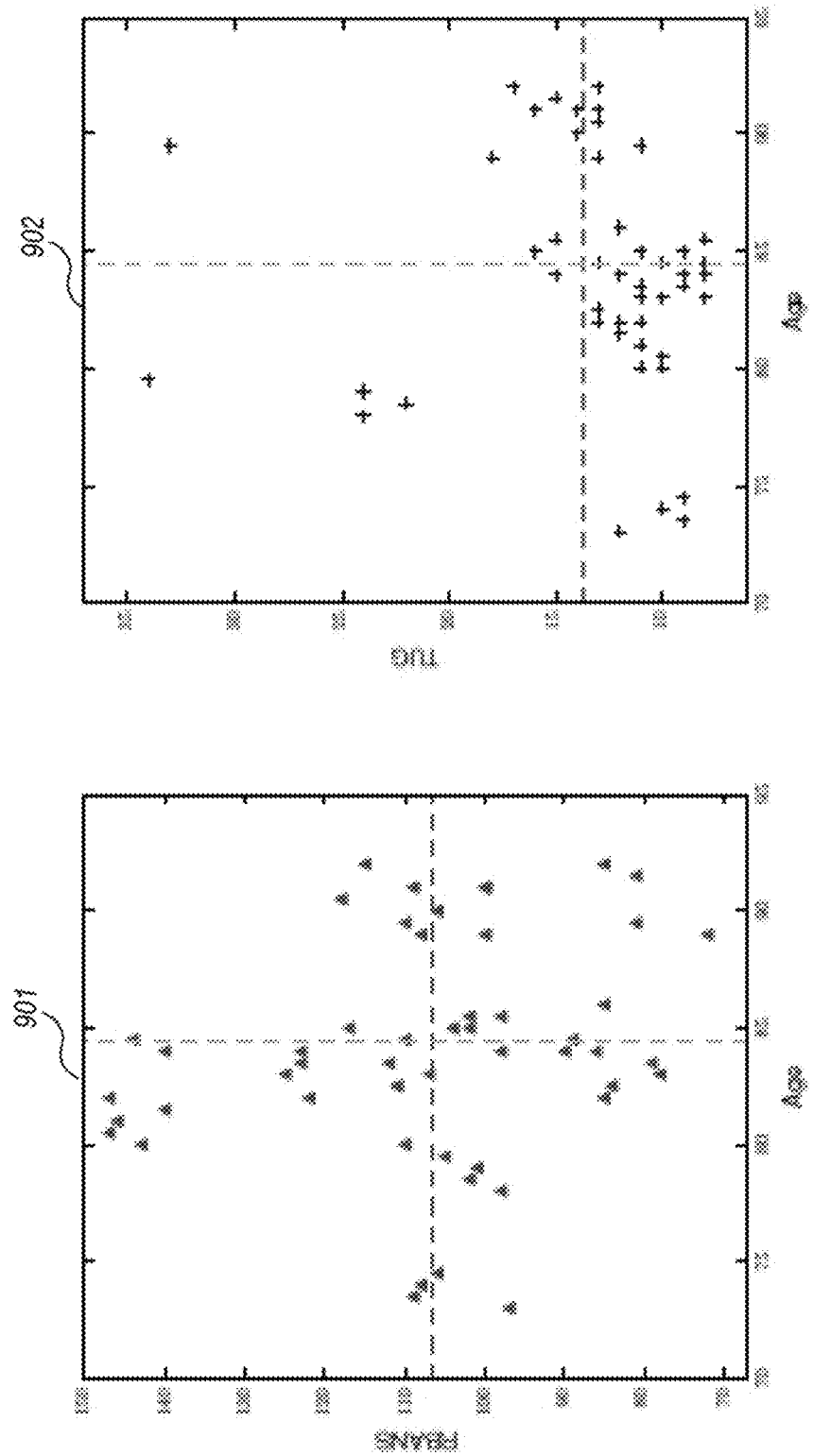
FIG. 9 plots the distribution of TUG and RBANS clinical assessment scores against the ages of the participants.

Clinicians biannually administered standardized clinical, cognitive, and motor tests to the residents. The tests included the Timed Up and Go mobility measure (TUG) as well as the Repeatable Battery for the Assessment of Neuropsychological Status measure of cognitive status (RBANS). The Timed Up and Go (TUG) measure [21] is a test that measures basic mobility skills. Participants are tasked with rising from a chair, walking 10 feet, turning around, walking back to the chair, and sitting down. The TUG measure represents the time required for participants to complete the task at a comfortable pace. The RBANS [20] is a global measure of cognitive status identifiers and characterizes cognitive decline in older adults. A clinical dataset was created using TUG and RBANS scores obtained from biannual clinical tests. FIG. 9 plots the distribution of these two scores against the ages of the participants. Chart 901 measures RBANS scores against age. Chart 902 measures TUG scores against age.

Prediction

We performed the following four different prediction-based experiments to evaluate the performance of CAAB approach and its components: 1) We first evaluate the overall CAAB performance in predicting clinical assessment scores. Here, we trained CAAB using the complete set of available features. We compared results from several representative supervised learning algorithms. 2) We then investigated the importance of different activity feature subsets by observing the resulting performance of CAAB in predicting the clinical assessment scores. 3) Next, we investigated the influence of parameter choices on performance by varying CAAB parameter values and analyzing the impact on prediction performance. 4) In the final experiment, we compared CAAB performance utilizing AR-labeled activities with a baseline method that utilized random activity labels.

We evaluated all of the above experiments using linear correlation coefficient (r) and mean squared error (RMSE). All performance values were generated using leave-one-out cross validation. The data for each participant was used for training or held out for testing, but was not used for both to avoid biasing the model. We used the following methods to compute our performance measures.

Correlation coefficient(r): The correlation coefficient between two continuous variables X and Y is given as:

$$r_{x,y} = \frac{\text{cov}(x, y)}{\sigma_x \sigma_y}$$

where $\sigma_x$ and $\sigma_y$ are the standard deviations of X and Y and coy (X, Y) is the covariance between X and Y In our experiments, we evaluate the correlation between the learned behavior model and clinical assessment scores. We end up interpreting the experimental results based on the absolute value of the correlation coefficient because our learning algorithm finds a nonlinear relationship between statistical activity features and the clinical assessment scores.

Root Mean Squared Error (RMSE): If $\hat{y}$ is a size-n vector of predictions and y is the vector of true values, the RMSE of the predictor is:

$$\text{RMSE} = \sqrt{\frac{1}{n}\sum_{i=1}^{n}(\hat{y}_i - y_i)^2}$$

1) Overall CAAB prediction performance: To validate the overall performance of CAAB performance, we computed correlations between the CAAB-predicted clinical assessment scores and the provided clinical assessment scores using the complete set of activity features and three different supervised learning algorithms:

Support Vector Regression (SVR): Support vector regression uses a support vector machine algorithm to make numeric predictions. The learning model can be expressed in term of support vectors and kernel functions can be used to learn a non-linear function. SVR uses the epsilon insensitive loss function that ignores errors that are smaller than threshold ∈>0. We used a linear kernel to generate all our prediction-based performance results [35].

Linear Regression (LR): Linear regression models the relationship between the class and the features as the weighted linear combination of the features. The weights are calculated from the training data often using the least square approach.

Random Forest (RF): Random forest builds an ensemble learner by creating multiple decision trees on different bootstrap samples of the dataset. It averages the predictions from these decision trees to make the prediction [35].

As listed in Table 4, we observed that the performances of the machine learning algorithms in predicting the clinical assessment scores were similar. We also observed that the correlation values were all statistically significant. Because SVR performed best overall, we conducted all of the remaining experiments using this approach. Additionally, we observed that the overall correlation between the predicted TUG scores and the actual TUG scores were weaker than the predicted RBANS and actual RBANS scores. The weaker correlation was likely due to the fact that there were only two activity performance features (mobility and leave home) that represent the mobility of an individual. Other activities such as cook, bed to toilet, and relax do not adequately represent the mobility of a resident.

TABLE 4

Overall Prediction Performance of the Different Learning Algorithms

| Score Type | Measure | SVR | LR | RF |
|---|---|---|---|---|
| RBANS | r | 0.72** | 0.64** | 0.52** |
|  | RMSE | 14.90 | 20.25 | 13.66 |
| TUG | r | 0.45** | 0.41* | 0.41** |
|  | RMSE | 5.87 | 7.62 | 5.22 |

(*p < 0.05, **p < 0.005)

2) CAAB prediction performance based on activity feature subsets: We performed a second set of prediction-based experiments using different subsets of statistical activity features to study and find the important sets of features as listed as follows:

1) We evaluated the prediction performances of the learning algorithm when it was trained using different subsets of statistical activity features.
2) We evaluated the result of using statistical activity features that belong to various subsets of ADLs.

In the first experiment, we studied the significance of five major types of statistical activity features (autocorrelation, skewness, kurtosis, variance, and change) that CAAB extracts from the activity performance features. To perform this experiment, we created five different training sets, each of which contains a subset of the statistical activity features. For example, the first training set contained all of the variance based features; the second training set contained all of the autocorrelation-based features etc. Using these training sets, we trained five separate support vector machines. As listed in Table 5, we note that the performance of the SVR in predicting clinical assessment scores using the variance of the activity features is strong as compared to other major types of statistical activity features. Therefore, we hypothesized that the variance of activity performance is an important predictor. Additionally, we observed that skewness-based feature is important for predicting TUG clinical scores while it was slightly weaker for RBANS predictions.

TABLE 5

Correlation Coefficient (R) and RMSE Values between SVR predicted RBANS and TUG Scores when SVR is trained using different types of Statistical Activity Features

| Score Type | Measure | Change | ACF | Skewness | Kurtosis | Variance | All Features |
|---|---|---|---|---|---|---|---|
| RBANS | r | 0.29 | 0.17 | 0.30* | 0.21 | 0.49** | 0.72** |
|  | RMSE | 25.77 | 21.39 | 19.90 | 25.19 | 17.76 | 14.94 |
| TUG | r | 0.06 | 0.05 | 0.43** | 0.06 | 0.31* | 0.45* |
|  | RMSE | 6.05 | 6.12 | 5.23 | 6.60 | 5.56 | 5.87 |

(*p < 0.05, **p < 0.005)

For the second CAAB feature-based experiment, we studied the relationship between the clinical assessment scores and the statistical activity features subsets that belong to various groups of ADLs. We created nine different ADL groups, each of which contains a combination of one or more activities (out of seven activities) and/or mobility. For each combination, we created a training set containing all statistical activity features belonging to the activities in that combination. In total, we create nine different training sets. As listed in Table 6, we make the following three observations:

1) In terms of single variables, sleep had the highest correlation with RBANS (r=0.51). In contrast, mobility showed little correlation with either clinical score.
2) We observed that correlation is higher when we combined variables. Specifically, including automatically recognized ADLs improved the correlation further for both RBANS (r=0.61) and TUG (r=0.48). RBANS showed highest correlation when all features are used (r=0.72).
3) In the case of TUG, the only two variable combinations that lacked a significant correlation included mobility. Once again, adding automatically-recognized activities generally increases the correlation.

TABLE 6

Correlation Coefficient (R) and RMSE Values between SVR-predicted RBANS and TUG Scores when SVR is Trained Using Features from Different Activities

| Score Type | Measure | Sleep | Mobility | ADL | Mobility + Leave Home |
|---|---|---|---|---|---|
| RBANS | r | 0.51** | 0.08 | 0.35* | 0.18 |
|  | RMSE | 17.53 | 21.66 | 20.15 | 24.49 |
| TUG | r | 0.26 | 0.05 | 0.35 | 0.34* |
|  | RMSE | 6.19 | 6.18 | 5.48 | 5.48 |

TABLE 6-continued

Correlation Coefficient (R) and RMSE Values between
SVR-predicted RBANS and TUG Scores when SVR is Trained
Using Features from Different Activities

| ADL + Leave Home | Sleep + Mobility | Sleep + ADL | Sleep + ADL + Leave Home | Mobility + ADL | All Features |
|---|---|---|---|---|---|
| 0.27 | 0.41* | 0.61** | 0.57* | 0.50** | 0.72** |
| 22.01 | 19.55 | 17.51 | 19.14 | 19.47 | 14.94 |
| 0.43* | 0.20 | 0.48** | 0.41 | 0.13 | 0.45* |
| 5.50 | 6.57 | 5.55 | 6.01 | 6.79 | 5.87 |

(*p < 0.05, **p < 0.005)

These results show that a relationship exists between RBANS and TUG clinical assessment scores with combined smart home-based parameters of sleep and ADLs. Our observations are interesting and align with results from prior clinical studies that have found relationships between sleep and ADL performance with cognitive and physical health [24], [36]. Furthermore, we also note that our observations are computed by making use of automated smart home sensor data and actual clinical assessment scores. The smart home sensor data are ecologically valid because the smart home collects data from the real world environment and CAAB extracts features without governing, changing, or manipulating the individual's daily routines.

3) CAAB performance using different parameters: We performed two different experiments to study the effect of parameter choices on CAAB. In these two experiments, we trained the learning algorithm using the complete set of features. We first studied how the activity features extracted at different window sizes affected the final performances of the learning algorithm. Second, we repeated the steps of the first experiment to study the effect of using different trend removal techniques.

Figure 10:
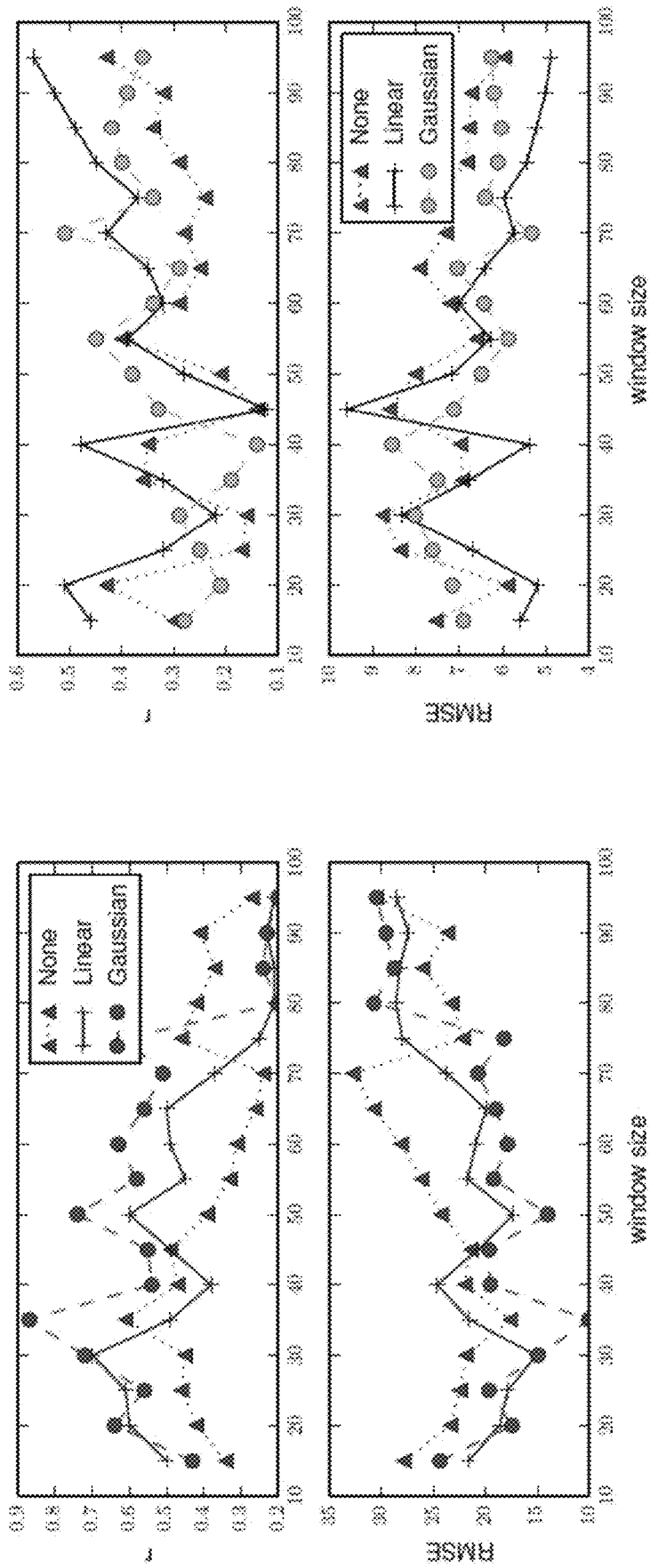
FIG. 10 illustrates the correlation coefficients and RMSE (root mean square error) values between predicted and actual cognitive assessment results using different trend removal techniques.

In the first experiment, we compared performance using different window sizes and the SVR learning algorithm. The results are summarized in FIG. 10. We observe that the strength of the correlation between the actual clinical assessment scores and predicted scores using features derived from smaller and mid-sized window is stronger than the larger-sized windows. One possible explanation is that larger windows encapsulate more behavior trends and day-to-day performance variation may be lost. Therefore, we use mid-sized (30 for RBANS and 55 for TUG) windows for all of our experiments. In the second experiment, we compare three different trend removal techniques. We create three different training sets that result from removing a Gaussian trend, a linear trend, and no trend removal. The results are showed in FIG. 10. We observe that the strength of the correlation coefficients is stronger and often RMSE values are smaller when we remove a Gaussian trend from the observations. Thus, in all of our remaining experiments, we remove a Gaussian trend from the data.

CAAB Performance Using Random Activity Labels

In our final prediction experiment, we compared CAAB performance using AR-labeled activities to CAAB performance using random activity labels. There were three main objectives of this experiment. First, we wanted to determine the importance of the role that the AR algorithm plays in CAAB. Second, we wanted to verify that CAAB is not making predictions based on random chance. Third, we let prediction performance based on random activity labels serve as a baseline or lower bound performance for comparison purposes. We expected CAAB performance using AR-labeled activities to significantly outperform the baseline performance.

To perform this experiment, we created a training set in which the statistical activity features (shown in Table 3) were calculated from the sensor data that was randomly labeled with the activity instead of using our AR algorithm to automatically generate activity labels. We performed this experiment using the following three steps: 1) We labeled raw sensor events by randomly choosing the activity labels from the activity set. We chose an activity assuming a uniform probability distribution over all activity classes. 2) We extracted statistical activity features from the sensor data labeled with the random activities. 3) We trained SVR using the statistical features and used clinical assessment scores as ground truth. Performance measures were computed as described in the previous sections.

Figure 11:
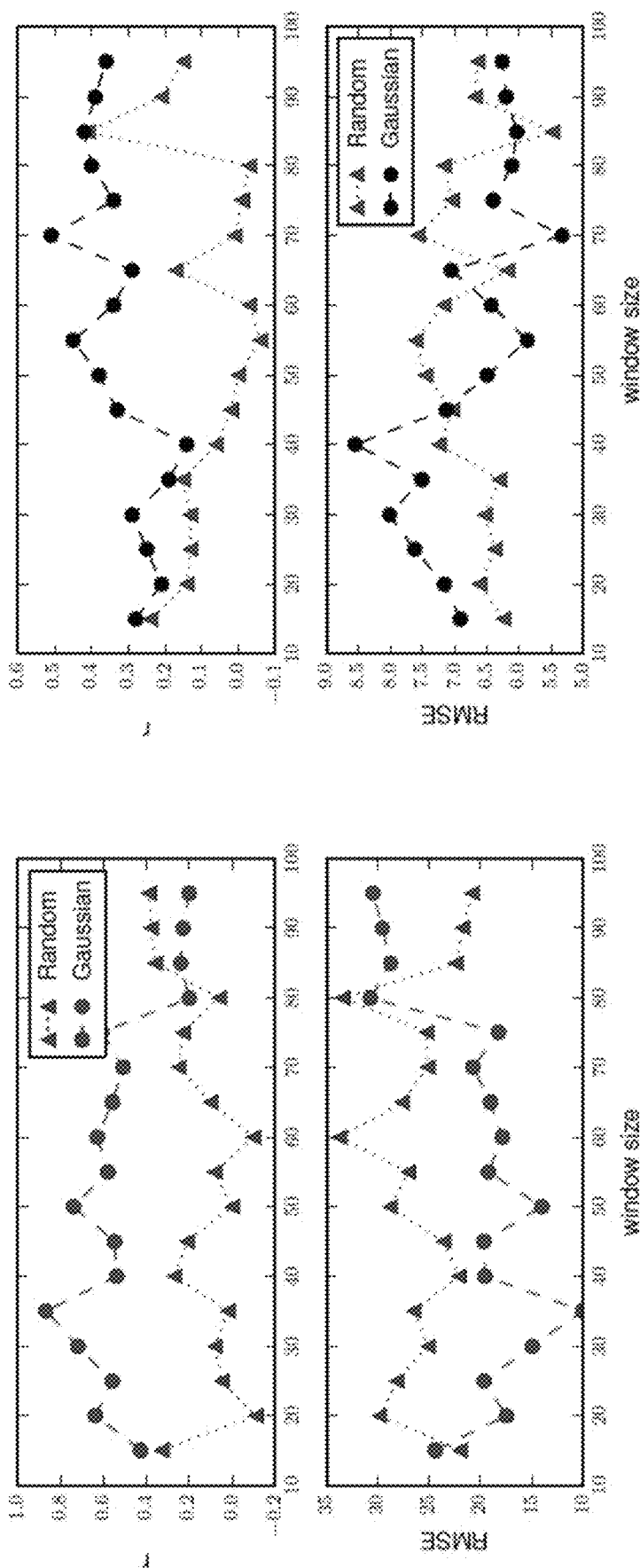
FIG. 11 illustrates the correlation coefficients and RMSE values when machine learning engine was trained using randomly labeled activities versus activity recognition algorithm labeled activities.

As shown in FIG. 11, we see that the strength of the correlation coefficients between predicted and actual clinical assessment scores were weak and that the RMSE values were high for the random approach. We also observed that the performances of the learning algorithms trained with features obtained from the AR labeled activities were significantly better than the random labels. Thus, we concluded that activity recognition plays a vital role in CAAB and that the CAAB predictions using statistical activity features extracted from AR labeled sensor data are meaningful and not obtained by chance.

Classification Experiments

To evaluate the performance of CAAB using various classification-based experiments, we first discretized the continuous clinical assessment scores into two binary classes and then used a learning algorithm to classify smart home residents into one of these two clinical groups. Performing these experiments allowed us to use traditional supervised learning-based methods and performance measures to evaluate CAAB, in contrast with the regression approaches. We trained the learning algorithms using the CAAB-extracted statistical activity features. For all of the classification-based experiments, we used a support vector machine (SVM) as the learning algorithm [35]. SVM identify class boundaries that maximize the size of the gap between the boundary and data points. We performed the following four different classification experiments: 1) We first evaluated classification performances of the SVM in classifying discretized RBANS and TUG clinical assessment scores when they are trained with different subsets of statistical activity features and activity performance features. 2) In the second experiment, we repeated the first experiment by discretizing RBANS and TUG scores into binary classes at different thresholds. 3) Next, we studied the classification performances of the learning algorithms trained using the activity features obtained from the sensor data labeled with random activities. 4) Finally, we evaluated the classification performance (error) by using a permutation-based test to ensure that the accuracy results were not obtained by a chance. We evaluated the classification performance of the learning algorithm using area under the curve, G-mean, accuracy and error and generate them using leave-one-out cross-fold validation.

ROC curves assess the predictive behavior of a learning algorithm independent of error cost and class distribution. The area under the ROC curve (AUC) provides a measure that evaluates the performance of the learning algorithm independent of error cost and class distribution.

G-Mean is the square root of the product of the true positive and true negative rate [35]. G-Mean= $\sqrt{(truepositiverate \times truenegativerate)}$ Accuracy is the percent of the correct predictions made by the learning algorithm by the total number of predictions. Accuracy=#Correct predictions/#Total predictions Error is the percent of the incorrect predictions made by the learning algorithm by the total number of predictions. Error=1−Accuracy.

1) CAAB classification performance based on feature subsets: Similar to the prediction-based experiments, we first studied the importance of different subsets of statistical activity features and subsets of activities. For the first experiment, we discretized clinical assessment scores (RBANS and TUG) into binary classes using an equal frequency binning technique. We then trained multiple SVMs to learn the relationship between CAAB-extracted activity features and these discretized clinical assessment scores. We make three observations based on the classification performances presented in Tables 7 and 8.

1) From Table 8, we observe that the performance of the learning algorithm that is trained with the AR-labeled activities including sleep and ADLs performs generally better than using other single variables.

2) From Table 7, we observe that the classification performances of the SVM when trained with variance based activity features are better for both RBANS and TUG scores. It appears that the skewness-based feature is only important for classifying RBANS clinical scores and not for the TUG classifications.

3) We note that the CAAB performance in the classification-based experiments involving smart home-based parameters of sleep and ADLs are similar to the performances in the prediction-based experiments.

TABLE 7

Classification Performance (Accuracy and AUC) of the SVM in Classifying Clinical Assessment Scores (RBANS and TUG) Discretized Using Equal Frequency Binning. SVM was Trained Using Statistical Activity Features From All Activities.

| Score Type | Measure | Change | ACF | Skewness | Kurtosis | Variance | All Features |
|---|---|---|---|---|---|---|---|
| RBANS | Accuracy | 26.92 | 57.69 | 73.07 | 57.69 | 63.46 | 71.75 |
|  | AUC | 0.27 | 0.58 | 0.73 | 0.58 | 0.63 | 0.71 |
| TUG | Accuracy | 66.00 | 42.00 | 46.00 | 62.00 | 62.00 | 76.00 |
|  | AUC | 0.65 | 0.39 | 0.44 | 0.60 | 0.62 | 0.75 |

TABLE 8

Classification Performance (Accuracy and AUC) of the SVM in Classifying Clinical Assessment Scores (RBANS and TUG) Discretized Using Equal Frequency Binning. SVM was Trained Using Features From Different Activities.

| Score Type | Measure | Sleep | Mobility | ADL | Mobility + Leave Home |
|---|---|---|---|---|---|
| RBANS | Accuracy | 76.92 | 57.69 | 46.15 | 61.53 |
|  | AUC | 0.76 | 0.57 | 0.46 | 0.62 |
| TUG | Accuracy | 78.00 | 62.00 | 66.00 | 52.00 |
|  | AUC | 0.77 | 0.61 | 0.64 | 0.52 |

Correlation Coefficient (R) and RMSE Values between SVR-predicted RBANS and TUG Scores when SVR is Trained Using Features from Different Activities

| ADL + Leave Home | Sleep + Mobility | Sleep + ADL | Sleep + ADL + Leave Home | Mobility + ADL | All Features |
|---|---|---|---|---|---|
| 61.53 | 75.00 | 73.08 | 75.00 | 48.05 | 71.15 |
| 0.62 | 0.75 | 0.73 | 0.75 | 0.49 | 0.71 |

TABLE 8-continued

| 52.94 | 62.00 | 76.00 | 80.00 | 44.00 | 76.00 |
|---|---|---|---|---|---|
| 0.50 | 0.62 | 0.75 | 0.79 | 0.43 | 0.75 |

(*p < 0.05, **p < 0.005)

Figure 12:
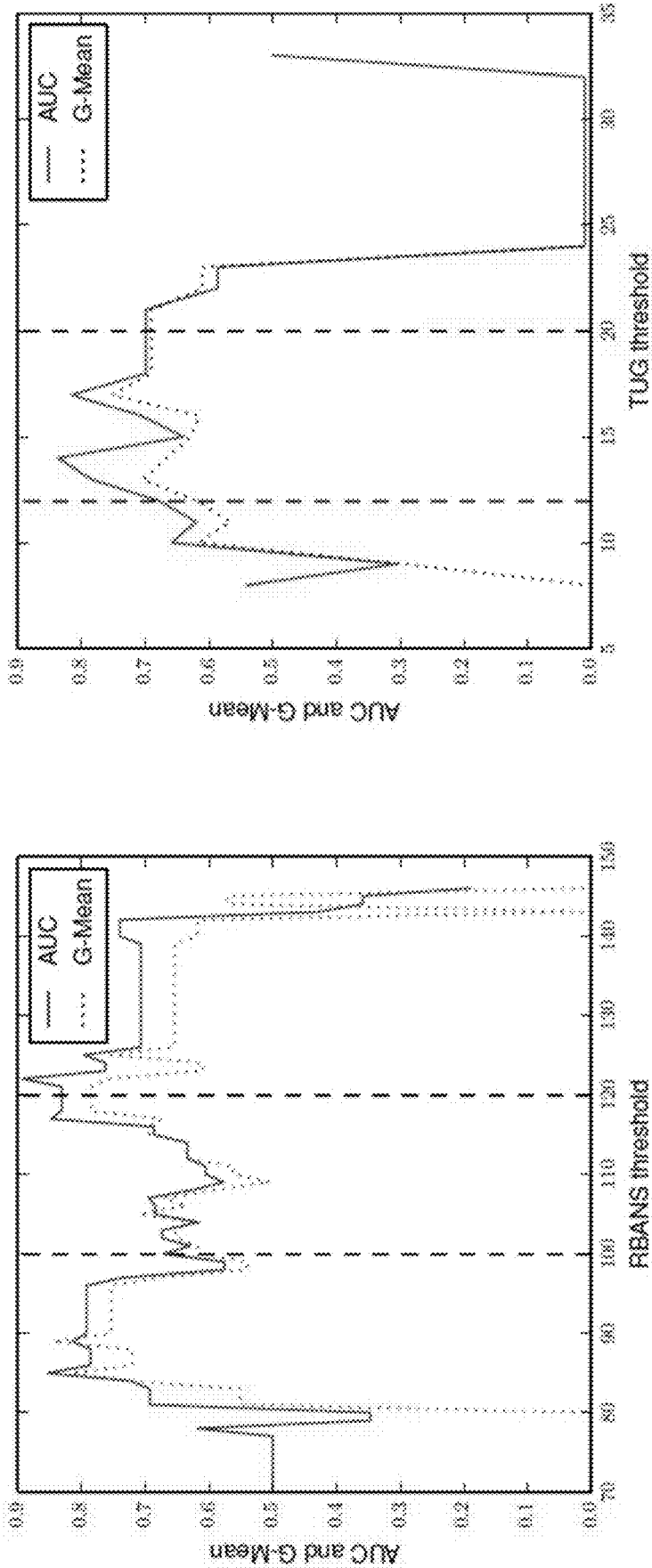
FIG. 12 illustrates variations in performance of learning algorithms when trained with class labels that were discretized at different thresholds.

In the second experiment, we evaluated the impact of CAAB performance of discretizing the continuous clinical assessment scores into binary classes at different cutoff thresholds. The objective of this experiment was to identify the range of thresholds that the learning algorithm can discriminate. For this experiment, we first discretized RBANS and TUG scores into binary classes at different thresholds. For this experiment, we used all the features to train the SVM with AdaBoost and generate performance metrics using leave one out cross validation. We used SVM/AdaBoost to handle the class imbalance in the dataset if there existed one [35]. The AdaBoost algorithm improves the accuracy of the "weak" learner by assigning greater weight to the examples that the learning algorithm initially fails to correctly classify [35]. The advantages of boosting the classifier to learn an imbalanced class is that since boosting weights the samples, it implicitly performs both up-sampling and down-sampling with little information loss and is also known to prevent overfitting [35]. As shown in FIG. 12 we observed some variations in the performance of the learning algorithms when they were trained with class labels that were discretized at different thresholds; however, the majority of the classification performances were better than random classification performances (i.e., 50% accuracy for binary classes).

Additionally, based on FIG. 12, we made four more observations:

- CAAB performance is generally better when the RBANS clinical score is discretized at thresholds within the lower range of RBANS (85-100) performances and within the higher range of RBANS (125-130) performances. It appears that the learning algorithm does successfully distinguish between the two extreme groups.
- CAAB classification performance is best when the continuous TUG clinical score is discretized at scores 12 and 17. We note that a score of 12 and above on the TUG puts individuals into the falls risk category [38]. Given that the TUG test measures the time that is required to comfortably complete the Timed Up and Go task, it appears that the learning algorithm can discriminate between the "slow performers" and the "fast performers."
- However, we note that similar to the prediction-based experiment, performance of the classifier in classifying TUG based scores is weaker than the performance while classifying RBANS scores. As we mentioned previously, this weaker performance is likely due to the fact that there are only two activity performance features (mobility and leave home) that represent the mobility of an individual.

Additionally, we note that CAAB performance in classifying both TUG and RBANS clinical labels are moderate to poor when the clinical scores are discretized into binary classes at the intermediate thresholds. We obtained moderate classification performances because the two classes are more likely to have "similar" activity performance and are therefore harder to distinguish from each other.

In the fourth experiment, we compared classification performance using AR-labeled activities and random activity labels. Similar to the prediction-based experiment, we expect the classification performance based on AR labeled activities to outperform the random method. As illustrated in FIG. 13, we observe that AR-based classification outperforms classification with random activity labels and that the results are similar to the earlier regression-based experiments (t-test on g-mean, p<0.05).

2) Permutation-based test: In the final experiment, we determined whether the aforementioned performance results were obtained because of chance, rather than because of the effectiveness of CAAB. With the permutation-based evaluation method, we calculated a p-value to test a null hypothesis about the relationship between the class labels and features. This p-value is calculated as a fraction of times that the performance of CAAB on the dataset that is obtained by shuffling (permuting) the class labels exceeded the performance of CAAB on the original dataset. Similar to the first classification-based experiment, we first discretized RBANS at a threshold of 105.5 and TUG at a threshold of 12.5 using an equal frequency binning technique. We performed a test proposed in Ojala and Garriga [38]. We randomly permuted the class labels to study the relationship between class labels and the features. (H): The null hypothesis is that there exists no relationship between the data and the class labels.

Table 9 presents the results from the AR annotated data. Based on the null hypotheses H, we made the following observation: the statistically significant (p<0.05) result for the null hypothesis (H) indicates that there exists a relationship between the sensor-based activity performance and discretized RBANS and TUG labels.

TABLE 9

Average Error and P-Value for Test Using SVMs and Activity Features Extracted from the Dataset Derived from AR-Annotated Activities

| Class Label | Original | Test 1 | |
| --- | --- | --- | --- |
| | Error | Err (std) | p |
| RBANS | 0.27 | 0.52 (0.11) | 0.009** |
| TUG | 0.24 | 0.42 (0.05) | 0.019* |

(*p < 0.05, **p < 0.005)

This experiment was repeated using activity features derived from randomly-labeled activities. Table 10 lists the results. Based on the p-values, we failed to reject the null hypothesis (H) that there exists no relationship between the class labels and features. Thus, we conclude that there exists a relationship between the smart home sensors-based activity features and standard clinical assessment scores (RBANS and TUG) and that the performance results are not obtained by chance.

TABLE 10

Average Error and P-Value for Test Using SVMs and Activity Features Extracted from the Dataset Derived from Randomly Labeled Activities

| Class Label | Original | Test 1 | |
| --- | --- | --- | --- |
| | Error | Err (std) | p |
| RBANS | 0.57 | 0.53 (0.07) | 0.65 |
| TUG | 0.38 | 0.37 (0.11) | 0.48 |

CONCLUSION

We described our CAAB approach to modeling a person's activity behavior based on smart home sensor data. CAAB collects sensor data, models activity performance, extracts relevant statistical features, and utilizes supervised machine learning to predict standard clinical assessment scores. This represents a longitudinal approach in which a person's own routine behavior and changes in behavior are used to evaluate their functional and mobility-based health. We validated our approach by performing several classification and prediction-based experiments. We found statistically significant correlations between CAAB-predicted and clinician provided RBANS and TUG scores. Our experiments were conducted using smart home data from 18 smart home residents and the majority of residents are cognitively healthy. We note that CAAB is not intended to replace existing clinical measurements with the smart home-based predictions but may provide a tool for clinicians to use. We also note that an advantage of CAAB is that sparsely-measured clinical scores can be enhanced using the continuously-collected smart home data and predictions.

APPENDIX B—EXPERIMENTAL USE OF ACTIVITY CURVES

An activity curve model provides a big data-based tool for representing a longer-term behavioral model. Such a tool is valuable for a variety of applications including human automation, health monitoring, and automated health assessment. In this section, we explain how the activity curve model and the PCAR algorithm can be instrumental in performing automated functional assessment. Activities of daily living such as sleeping, grooming, and eating are essential everyday functions that are required to maintain independence and quality of life. Decline in the ability to independently perform these ADLs has been associated with a host of negative outcomes, including placement in long-term care facilities, shortened time to conversion to dementia, and poor quality of life for both the functionally impaired individuals and their caregivers [66],[67],[68]. We use smart home sensor data to derive activity curves that model the activity routines of a smart home resident. Our PCAR algorithm detects changes in those activity routines. We note that changes in ADL patterns are one of the many forms of behavioral changes that are frequently associated with changes in cognitive and physical health. We hypothesize that activity curve will allow us to detect changes in ADL patterns which possibly can provide valuable information about a change in the health condition. To validate our automated assessment technique, we utilize smart home sensor data that was collected from real world smart home test beds with older adult residents. We apply robust activity recognition algorithms [69], [70] to label these sensor-monitored data with the corresponding activity labels.

Synthetic Dataset

First, we validate the performance of the proposed PCAR algorithm by running it on a synthetic activity curve. We create a synthetic activity curve by compiling synthetic activity distributions. The synthetic activity distribution models the patterns of two activities, an arbitrary activity A and an "other" activity. We generate synthetic activity distributions for each time interval t for N days by applying the following three steps. Here I represents the length of each time interval.

Generate a random value p ($0 \leq p \leq 1$), which represents the average time that is spent in performing activity A during time interval t.

Generate two vectors, S and S', each of length N. Generate the vector S from a normal distribution i.e. S~Normal (p, 1). Each element of vector S' is generated by subtracting the corresponding value in S from 1, i.e., $1-s \in S'$.

Create an activity distribution that models patterns of two activities at a time interval t. The elements of the activity distribution is [s,1−s]. We combine these individual synthetic activity distributions at different time intervals into activity curves. When we introduce an activity change, we multiply the average time spent performing an activity A by a constant factor in each time interval.

Using the aforementioned method, we create two different sets of activity curves. The first set Y does not contain any changes and another different set of daily activity curves Z contains changes in all activity distributions every 90 days. We run the PCAR algorithm on an aggregated activity curve of size 90 days using the time interval index alignment. PCAR successfully detects all changes in the dataset where activity changes were made and does not produce any false positives in the synthetic dataset that does not contain changes.

Next we demonstrate how PCAR can be used to detect changes in real smart home data. For this study, we recruited 18 single-resident senior volunteers from a retirement community and installed smart home sensors in their homes [71]. (See FIG. 1.) The smart home sensors unobtrusively and continuously monitor resident activities. We continuously collected raw sensor events for an extended period (~2 years) from all of the residents. At the same time, standardized clinical, cognitive, and motor tests were administered biannually to the residents.

Participants

Participants included 18 senior residents (5 females, 13 males) from a senior living community. All participants were 73 years of age or older, and had a mean level of education of 17.52 years. At baseline, participants were classified as cognitively healthy (N=7), at risk for cognitive difficulties (N=7) or experiencing cognitive difficulties (N=4). One participant in the cognitively compromised group met the criteria for dementia[72], while the other three individuals met the criteria for mild cognitive impairment (MCI)[73].

Smart Home Test Environment

The 18 smart home test beds are single-resident apartments, each with at least one bedroom, a kitchen, a dining area, and one bathroom. The sizes and layouts of these apartments vary from one apartment to another. The apartments are equipped with combination motion/light sensors on the ceilings and combination door/temperature sensors on cabinets and doors (as shown in FIG. 1).

The activities were annotated with an activity recognition algorithm as described above. Clinical tests were administered every six months including TUG and RBANS measures of cognitive status.

Experimental Results

Preprocessing

We used two different preprocessing techniques to preprocess activity curves.

Mean smoothing: We ran a mean smoothing filter of size 3 on activity distributions comprising the activity curve to smooth out noise and minor variations. In this step, we replace the estimate at time interval t with the average estimate of activity distributions at times t−2, t−1, and t.

Add-One smoothing: Activity distributions for certain activities can be zero. For example, we rarely eat and cook at midnight so activity distributions of these activities at midnight are often zero. We perform add-one smoothing on all of the elements of activity distributions. In add-one smoothing, we add a constant $\alpha=1$ in every elements of the activity distributions. Add-one smoothing technique is often used in natural language processing to smooth unigram estimates and has an effect of removing zero entries.

Studying Aggregated Activity Curves

Figure 14:
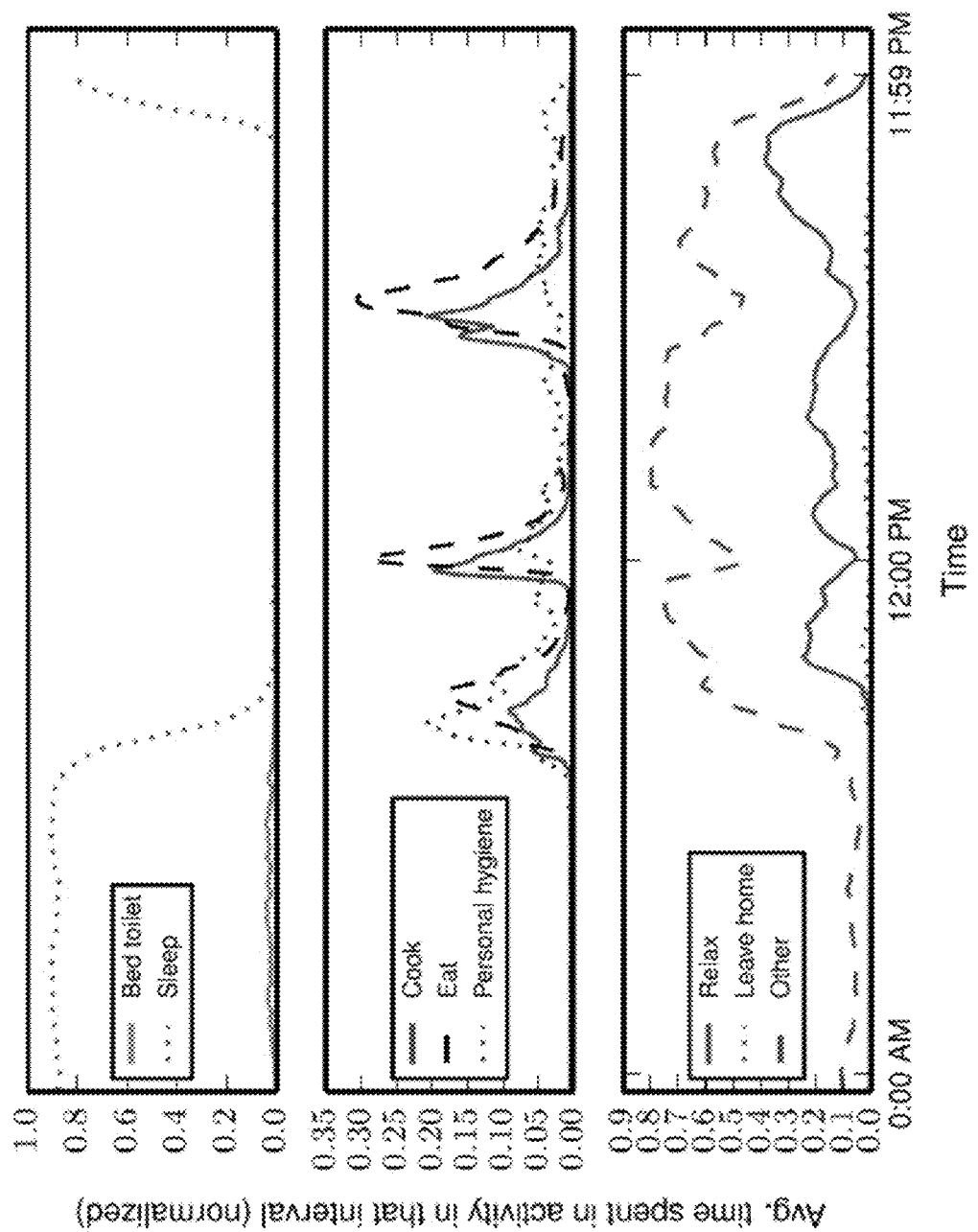
FIG. 14 is an example aggregated activity curve that model eight different activities of daily living.

FIG. 14 is an example aggregated activity curve that models eight different activities, including seven recognized activities (i.e., sleep, bed toilet transition, eat, cook, relax, personal hygiene) and an "other" activity. This sample aggregated activity curve was derived using an aggregation window of size x=three months based on actual single resident smart home sensor data and 5 min time intervals. We observe that this smart home resident usually goes to sleep at around 9:00 PM and wakes up at around 7:00 AM. We also observe that the resident exhibits a fairly fixed schedule for eating breakfast, lunch, and dinner.

Comparing Activity Distributions

Figure 15:
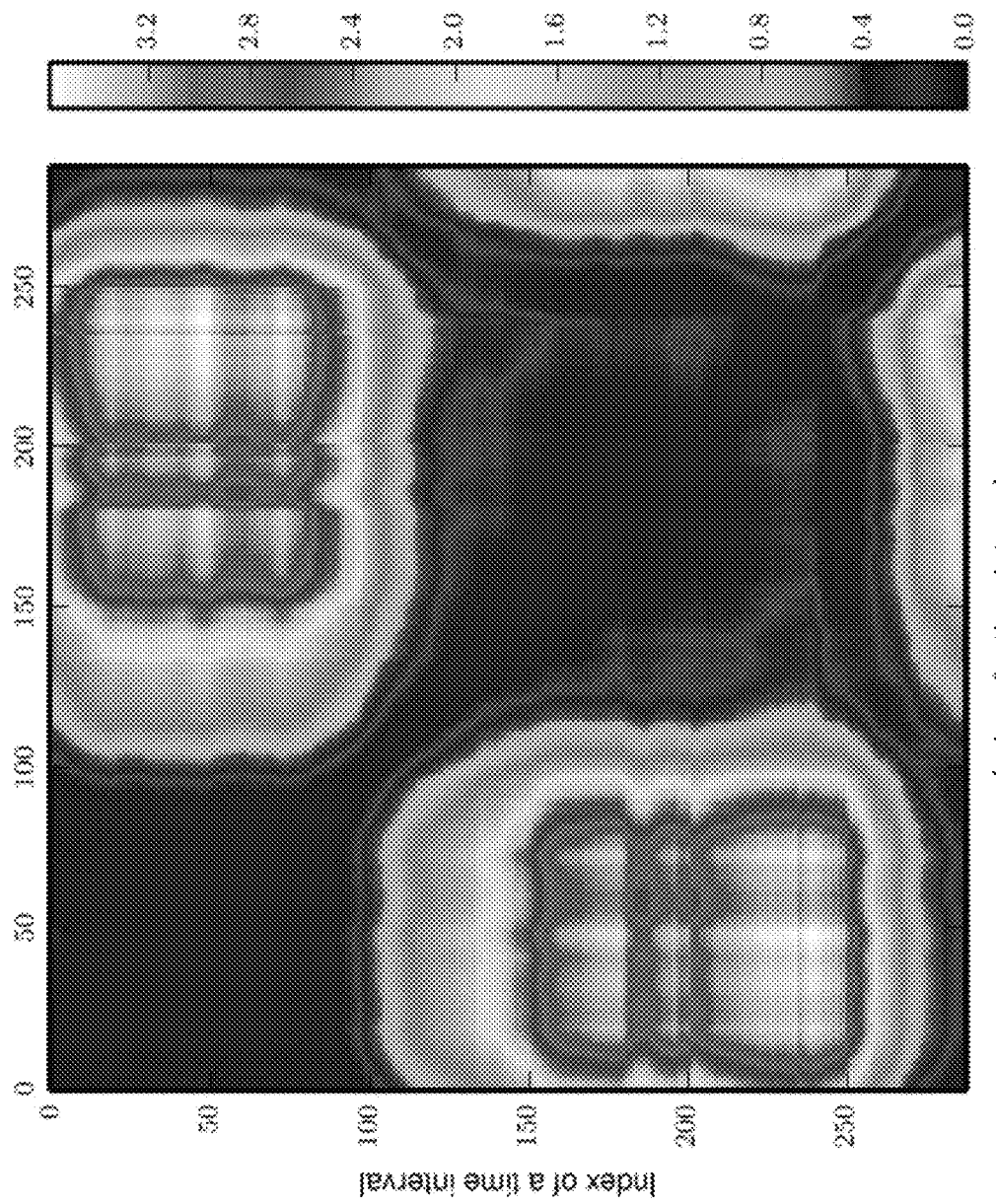
FIG. 15 is a heat map representation of the pairwise distance matrix between activity distributions computed from the aggregated activity curve of FIG. 14.

For most individuals, our activities follow a common pattern based on factors such as time of day. Thus, the activity distributions that model activities at different time intervals belonging to different times of a day will be different. In our first experiment, we assess whether our proposed activity curve can capture such differences in activity distributions. We calculate an aggregated activity curve for five-minute time intervals using the first three months of activity-annotated sensor data from one of our smart homes. We calculate a pairwise distance (symmetric KL divergence) matrix between activity distributions from this aggregated activity curve. We plot this pairwise distance matrix in a heat map shown in FIG. 15. From the heat map, we observe that the distance between activity distributions varies according to the time of day. We observe that the darkest colors appear along the diagonal when we compare activity distributions for the same time of day. In contrast, we observe that the hottest colors (greatest distance) occurs when comparing activities at midnight (when the resident typically sleeps) to activities in mid-afternoon when the resident is quite active. Additionally, we also see different clusters emerge (for instance, between times 0 and 100) corresponding to times of day. These observations provide intuitive visual evidence that the activity curve is capturing generalizable differences in activity routine at various times of the day.

Figure 16:
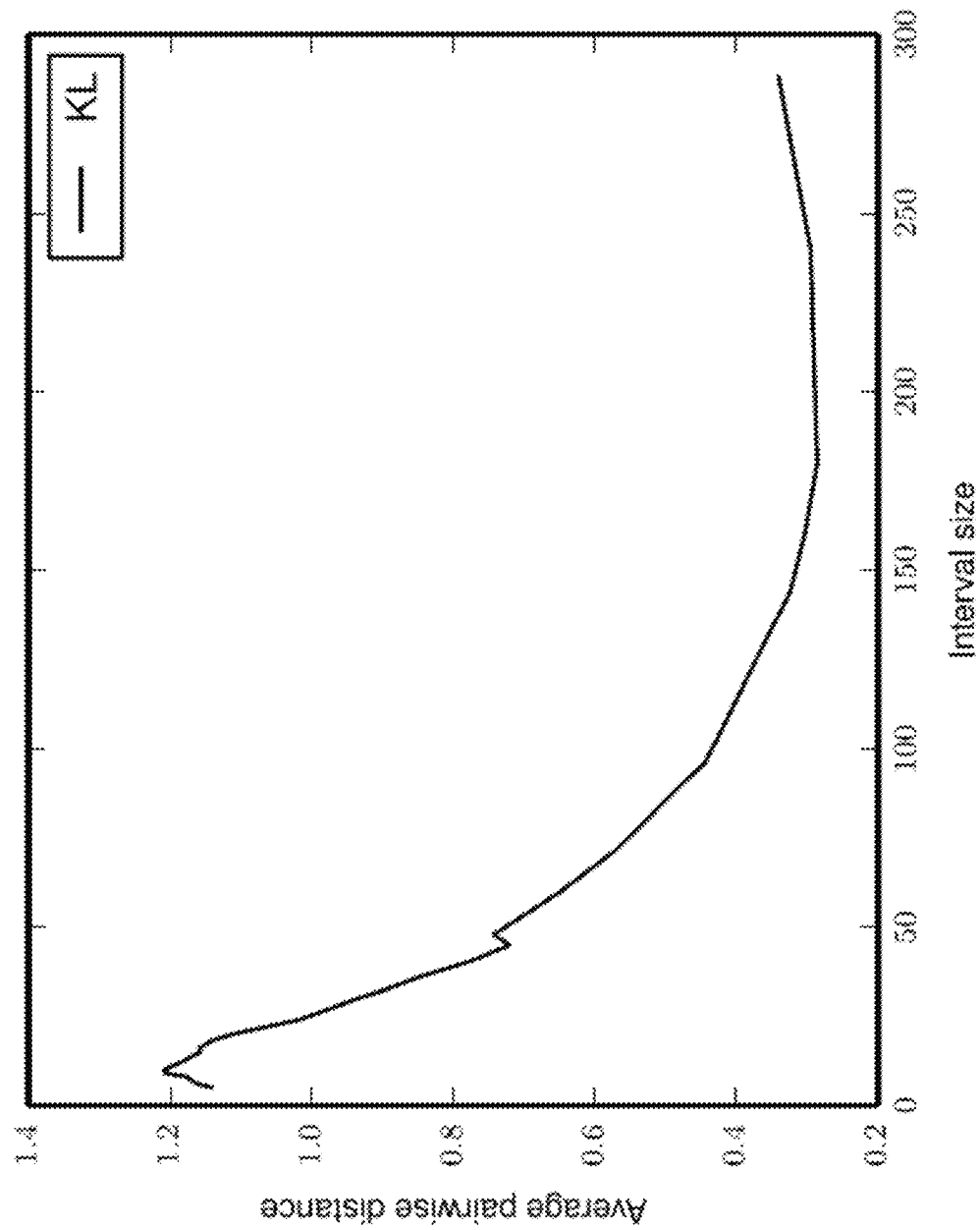
FIG. 16 illustrates how activity distribution distances within an activity curve change as a function of time interval.

In the next experiment, we study how the activity distribution distances within an activity curve (the y axis in FIG. 16) change as a function of the time interval size (the x axis).

For this experiment, we calculated an average pairwise distance between activity distributions within aggregated activity curve for each time interval size. We observe that as the time interval increases, the average pairwise distance between daily activity distributions decreases. Such a decrease in distances is observed because activity distributions at larger sized time intervals are overwhelmed by activities that take larger duration (such as sleep). As a result, smaller differences between such activity distributions are harder to detect.

Aggregation Window Size

Figure 17:
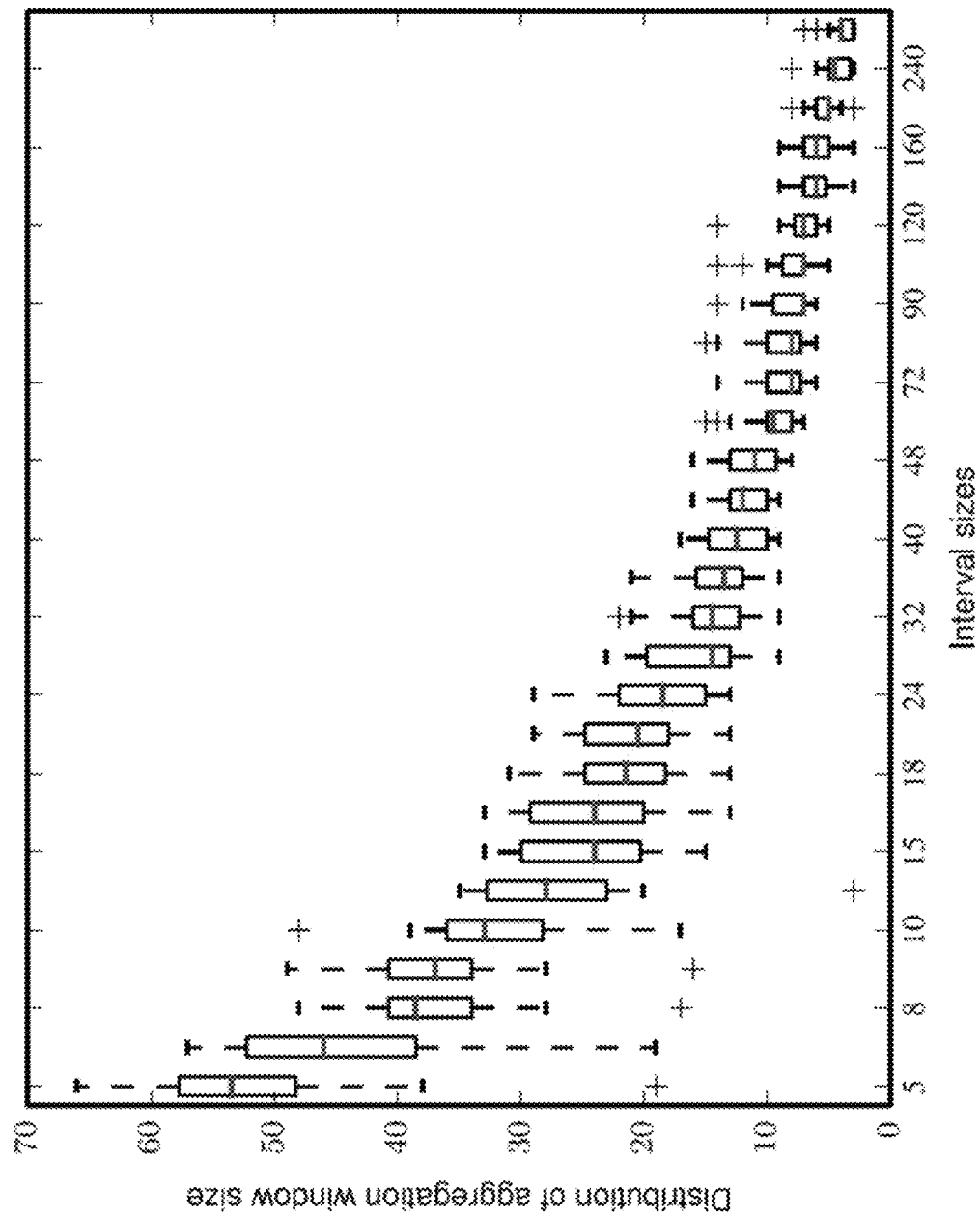
FIG. 17 illustrates the variations in the length of an aggregate window at different interval sizes calculated using available sensor data.

In the next experiment, we determine the minimum length of an aggregation window that is required to calculate a stable aggregated activity curve for our smart home data. FIG. 17 shows the variations in the length of an aggregate window at different interval sizes calculated using all the available sensor data. We observe that the length of the aggregation window is larger for the smaller interval sizes and smaller for the larger interval sizes. We can explain such differences in length of the aggregation window based on the observations we made between average pairwise distances and interval sizes in FIG. 17. At larger interval sizes, activity distributions are dominated by activities that take a long time to complete (such as sleep). Thus, the distance between two activity distributions for such activity curves are significantly lower than the distance between two activity distributions for activity curves at smaller time intervals. Hence, we obtain a stable activity curve using a smaller aggregation window size for larger interval sizes.

Change Scores and Correlations

In this section, we study the strength of the correlations between the changes detected in activity routines by the PCAR algorithm and the corresponding standard clinical scores (RBANS and TUG) for a smart home resident. Specifically, we calculate correlations between change scores calculated by applying PCAR on activity curves derived using activity labeled smart home sensor data and corresponding clinical scores ensuring that each pair of the smart home change score and clinical score was observed at around the same time.

To obtain such correlations, we first calculate aggregated activity curves for two three-month aggregation windows, $W_1$ and $W_2$. Next, we apply PCAR to these activity curves to obtain a smart home-based change score. We also obtain clinical scores measured at time points, $t_1$ and $t_2$. We repeat this step for all available pairs of consecutive testing time points for all 18 residents. Finally, we calculate Pearson correlation and Spearman rank correlation between the activity change scores and the corresponding clinical scores to evaluate the strength of the relationship. The process is summarized in Algorithm for BehaviorAndHealthCorrelation(t) below. To evaluate our automated health correlation based on smart home data, we derived correlation coefficients between change scores obtained from the smart home-based activity curve model with the standard health clinical scores (TUG and RBANS scores). To conduct this experiment, we ran 1500 permutation iterations and derived change scores for both alignment techniques. We repeated the experiments for different time interval sizes. As a baseline for comparison, we generated random change scores by randomly predicting a change between activity distributions instead of using the PCAR algorithm. Tables 1 and 2 shown in FIGS. 18A-18B list the correlations between these two scores for different time interval sizes.

```
ALGORITHM for BehaviorAndHealthCorrelation(t)

1:    // t - testing time points
 2:    // Return correlation coefficient.
 3:    BehaviorChangeScores = [ ]
 4:    ClinicalChangeScores = [ ]
 5:    i = 0
 6:    repeat
 7:       Σ₁ = AggregateActivityCurvesAtTime (tᵢ + 3 months)
 8:       Σᵢ₊₁ = AggregateActivityCurvesAtTime (tᵢ + 1 + 3 months)
 9:       Dist = EmpiricalDistribution (Σᵢ, Σᵢ₊₁, Nₚ)
10:       S₁ = PCAR (Σᵢ, Σᵢ₊₁, Dist)
11:       S₂ = ClinicalScores (tᵢ, tᵢ + 1)
12:       Append (S₁, BehaviorChangeScores)
13:       Append (S₂, ClinicalChangeScores)
14:       i = i + 1
15:    until
12:    return Correlation (S₁, S₂);
```

We make the following observations:

We obtain statistically significant correlations between activity change scores and TUG scores (FIG. 18B).

No correlations exist between activity change scores obtained from random predictions and TUG scores.

No correlations exist between smart home based activity change scores and RBANS scores.

Often, the strength of correlations at larger time interval sizes is weak because at larger time intervals activities are either dominated by sleep activity or other activity. Hence, changes in activity distributions at large time intervals are comparatively harder to detect.

Continuous Change Scores

In the previous section, we predicted change scores at six month intervals to correlate the smart home-based behavior change scores with changes in standard clinical scores. We can also calculate these change scores more frequently by running the PCAR algorithm on the activity curves that lies within a sliding window of size six months and shifting this sliding window by one month (30 days). We will refer to such frequent change scores as continuous change scores. We can use continuous change scores to monitor the "performance" of a smart home resident's everyday behavior.

FIG. 19 shows how the continuous change scores of two smart home residents have varied with time. Each point in a plot represents a total change score obtained by using the PCAR algorithm to compare behavior six months prior with current behavior. First, we plot continuous change scores of a resident whose health status has declined (FIG. 19). We observe that after a year, the total change score of this resident started to fluctuate. Such fluctuations indicate changes in the average daily routines of this resident. Similarly, we plot continuous change scores of another resident whose health has been in excellent condition for the entire data collection period (FIG. 19). We observe that the PCAR algorithm detects very few changes in the average daily routines of this resident.

Individual Activity Change

The change scores calculated in the previous sections quantify overall changes in average daily routines for the entire collection of known activities. In this experiment, we can quantify total changes in the average daily routines of some specific activities by running PCAR algorithm on a reduced activity set. The elements in this reduced activity set are activities that we want to monitor and the "other activities" class is used to represent all of the remaining activities. For example, if we want to monitor sleep and bed to toilet activities, we put three elements (sleep, bed to toilet and other) in the reduced activity set. Using this reduced set of activity, we can use PCAR to obtain continuous change scores. FIG. 20 shows the continuous sleep change scores of the same two smart home residents for whom we studied the continuous change scores in FIG. 19. We see that PCAR detected changes in the overall sleep routine of the first resident while it does not detect any sleep routine changes for the other resident.

CONCLUSIONS

We developed an activity curve model to represent daily activity-based behavior routines. The activity curve models the activity distributions of the activities at different times of a day. Using the activity curve model, we developed and tested the PCAR algorithm to identify and quantify changes in the activity routines. We validated our model by performing experiments using synthetic data and longitudinal smart home sensor data. PCAR is able to represent behavior patterns through big data analysis.

The current activity model considers activity distributions using different interval sizes. Further, while performing experiments with an activity curve model, we chose a subset of activities that are considered important in daily life. We also note that the activities that did not fit into these seven predefined categories were termed "other". We note that the "other" data is very large, complex, and represents important activities that could be added to our activity vocabulary in future embodiments.

We developed the PCAR algorithm to quantify changes in an activity routine. PCAR makes use of a smart home sensor data of an individual collected over a period to quantify changes in the activity routine and outputs change scores. This algorithmic approach is important because activity routines vary among individuals.

In this experiment, we studied the relationship between the output from the PCAR algorithm and the standard clinical and physical health scores. We found moderate correlations between the change scores and standard TUG scores. However, we found that the correlations between smart home-based change scores and standard cognitive scores (RBANS) were not as strong as we expected because the majority of the older adults for whom we analyzed the data are healthy older adults. We note that clinicians have frequently argued for the existence of a relationship between changes in ADL patterns and changes in the health. We want to use our idea of an activity curve to detect changes in ADL patterns which possibly can be associated with a change in cognitive and physical health conditions. Similarly, we also demonstrated methods to evaluate the "average performance" of a smart home resident by continuously monitoring changes in the overall daily routine as well as a set of specified activities.

The work described here confirms that pervasive computing methods can be used to correlate an individual's behavior patterns and clinical assessment scores. Visualization tools for the activity curve model could be incorporated.

The invention claimed is:

1. A method in a computing system for facilitating a cognitive assessment of an individual, comprising;
   receiving from a plurality of smart sensors installed in a residence, a continuous stream of raw output data of sensor events, the sensor events corresponding to a plurality of activities engaged in by the individual in the residence, the raw output data of each sensor event including at least a date, time, sensor identifier, and sensor value;
   using automated activity recognition logic, automatically labeling the raw output data of each sensor event in the continuous stream with an activity label that corresponds to a detected activity of the individual, the automatic labeling transforming the data into measurements of activities of daily living;
   automatically extracting activity performance features from the activity labeled sensor data, wherein each activity performance feature includes a time-based feature and a sensor-based feature;
   automatically extracting statistical features from the extracted activity performance features, the extracted statistical features further measuring attributes over time of each extracted activity performance feature between at least two clinical cognitive testing point times; and
   submitting indications of the extracted statistical features to a machine learning engine configured to predict and output a cognitive assessment score using the sensor event data and the extracted statistical features, the machine learning engine modeling relationships between clinical cognitive assessment scores and activity performance features to correlate the predicted cognitive assessment score to a clinical cognitive assessment.

2. The method of claim 1, the outputting the cognitive assessment score further comprising forwarding the predicted clinical cognitive assessment to a clinician for further diagnosis of cognitive state.

3. The method of claim 1 wherein the plurality of smart sensors comprise one or more motion sensors, light sensors, door sensors, or temperature sensors, wherein each sensor is associated with an identifier that identifies a location in the residence.

4. The method of claim 1 wherein the automatically labeling of the raw output data of each sensor event with an activity label includes labeling the data with activities indicating two or more of mobility, sleep, or activities of daily living.

5. The method of claim 4 wherein the activities of daily living comprise cooking, eating, relaxing, personal hygiene, or leaving home.

6. The method of claim 4 wherein the sleep label includes sleeping and a bed to toilet transition.

7. The method of claim 1 wherein the time-based feature includes an indication of duration of the activity and the sensor-based feature includes an indication of number of corresponding sensor events.

8. The method of claim 1 wherein extracting activity performance features further comprises extracting statistical activity features from the extracted activity performance features and the extracted statistical activity features include one or more of measures of variance, autocorrelation, skewness, kurtosis, or change.

9. The method of claim 1 wherein the sensor data is received continuously and wherein the activity recognition logic annotates and transforms the data by viewing the data in continuously moving evaluation windows over the data such that each evaluation window provides context for evaluating a newly received input of sensor data.

10. The method of claim 9 wherein the sensor data is received in near real time.

11. The method of claim 1 wherein indications of the extracted activity performance features are compared with actual clinical assessments to train the machine learning engine such that clinical data of the resident is used as a baseline for predictive assessment.

12. The method of claim 1 wherein the machine learning engine is a support vector machine.

13. A cognitive facilitator assessment computing system comprising;
- a memory;
- a computing processor;
- a machine learning engine; and
- clinical assessment activity behavior tool stored in the memory and further comprising:
  - sensor input logic configured, when executed, to provide one or more streams of continuous live smart-home based sensor data corresponding to activities of a resident in a residence, with the residence having a plurality of smart-home based sensors installed therein;
  - an activity recognizer configured, when executed, to receive the continuous sensor data real time and to label the sensor data with activity labels to transform the data into measurements of activities of daily living;
  - an activity performance features extractor configured, when executed, to automatically extract activity performance features from the activity labeled sensor data, the activities corresponding to activities of daily living and/or mobility, wherein each extracted activity performance feature includes a time-based feature and a sensor-based feature;
  - a statistical feature extractor configured, when executed, to automatically extract statistical features from the extracted activity performance features, the extracted statistical features further measuring attributes over time of each extracted activity performance feature between at least two clinical cognitive testing point times; and
  - a cognitive assessment predictor configured, when executed, to receive the extracted performance features and to submit them to the machine learning engine to automatically predict a cognitive assessment score using the sensor event data and the extracted statistical features, the machine learning engine modeling relationships between clinical cognitive assessment scores and activity performance features to correlate the predicted cognitive assessment score to a clinical cognitive assessment.

14. The cognitive facilitator assessment computing system of claim 13 wherein the cognitive assessment predictor is further configured, when executed, to train the machine learning engine by initially submitting extracted statistical features of the extracted activity performance features with actual clinical assessments.

15. The cognitive facilitator assessment computing system of claim 13 wherein the extracted statistical features of the extracted activity performance features comprises at least one of variance, autocorrelation, skewness, kurtosis, or change.

16. The cognitive facilitator assessment computing system of claim 13 wherein the time-based feature includes an indication of duration of the activity and the sensor-based feature includes an indication of number of corresponding sensor events.

17. A non-transitory computer-readable memory medium containing contents for instructing a computer process to facilitate a cognitive assessment of a resident of a residence using a plurality of smart sensors installed in the residence, by performing a method comprising:
- receiving from the plurality of smart sensors, a continuous stream of raw output data of sensor events, the sensor events corresponding to a plurality of activities engaged in by the individual in the residence, the raw output data of each sensor event including at least a date, time, sensor identifier, and sensor value;
- automatically labeling the raw output data of each sensor event in the continuous stream with an activity label that corresponds to a detected activity of the resident, the automatic labeling transforming the raw output data into measurements of activities of daily living;
- automatically extracting activity performance features from the activity labeled sensor data, wherein each extracted activity performance feature includes a time-based feature and a sensor-based feature;
- automatically extracting statistical features from the extracted activity performance features, the extracted statistical features further measuring attributes over time of each extracted activity performance feature between at least two clinical cognitive testing point times; and
- submitting indications of the extracted statistical features to a machine learning engine to predict a cognitive assessment score using the continuous sensor event data and the extracted statistical features, the machine learning engine modeling relationships between clinical cognitive assessment scores and activity performance features to correlate the predicted cognitive assessment score to a clinical cognitive assessment.

18. The memory medium of claim 17 wherein the automatically labeling of the raw output data of each sensor event in the continuous stream with an activity label includes labeling the data with activities indicating mobility, sleep, and activities of daily living.

19. The memory medium of claim 18 wherein the activities of daily living comprise cooking, eating, relaxing, personal hygiene, or leaving home.

* * * * *